US007253194B2

(12) United States Patent
Reid et al.

(10) Patent No.: US 7,253,194 B2
(45) Date of Patent: Aug. 7, 2007

(54) COMPOUNDS AND INHIBITORS OF PHOSPHOLIPASES

(75) Inventors: Robert C Reid, Chelmer (AU); Christopher I Clark, Taringa (AU); Karl Hansford, Delveen (AU); Martin J Stoermer, Brookfield (AU); Ross P McGeary, St. Lucia (AU); David P Fairlie, Daisy Hill (AU); Karl Schafer, Carindale (AU)

(73) Assignee: The University of Queensland, Queensland (AU)

( * ) Notice: Subject to any disclaimer, the term of this patent is extended or adjusted under 35 U.S.C. 154(b) by 262 days.

(21) Appl. No.: 10/333,871

(22) PCT Filed: Jul. 24, 2001

(86) PCT No.: PCT/AU01/00898

§ 371 (c)(1),
(2), (4) Date: Aug. 25, 2003

(87) PCT Pub. No.: WO02/08189

PCT Pub. Date: Jan. 31, 2002

(65) Prior Publication Data
US 2004/0033995 A1 Feb. 19, 2004

(30) Foreign Application Priority Data
Jul. 24, 2000 (AU) .................... PQ8965
Nov. 24, 2000 (AU) .................... PR1669

(51) Int. Cl.
*A61K 31/44* (2006.01)
*A61K 31/165* (2006.01)
*A61K 31/351* (2006.01)
*C07C 233/08* (2006.01)
*C07C 213/46* (2006.01)
(52) U.S. Cl. ............... 514/357; 514/459; 514/617; 546/339; 549/427; 564/161
(58) Field of Classification Search ........... 514/357, 514/459, 617; 546/339; 549/427; 564/161
See application file for complete search history.

(56) References Cited
U.S. PATENT DOCUMENTS

| 5,455,271 | A | * | 10/1995 | Yuan et al. ........... 514/538 |
| 5,481,011 | A | * | 1/1996 | Chen et al. ........... 549/514 |
| 5,916,878 | A | | 6/1999 | Kolobov et al. .......... 514/19 |
| 2002/0128255 | A1 | * | 9/2002 | Beck et al. ........... 514/211.15 |
| 2004/0247639 | A1 | | 12/2004 | Shiels et al. |

FOREIGN PATENT DOCUMENTS

| EP | 691345 | * | 1/1996 |
| WO | 91/08737 | | 6/1991 |
| WO | 9400420 | * | 1/1994 |
| WO | 94/28004 | | 12/1994 |
| WO | 95/19959 | | 7/1995 |
| WO | 97/03951 | | 2/1997 |
| WO | 9838167 | * | 9/1998 |
| WO | 2002002512 | * | 1/2002 |

OTHER PUBLICATIONS

Teno et al., Chem. Pharm. Bull. (1993), vol. 41(6), pp. 1079-1080.*
Bae, J. et al., "Stimulation of pregnant rat uterine contraction by the polychlorinated biphenyl (PCB) mixture aroclor 1242 may be mediated by arachidonic acid release through activation of phospholipase $A_2$ enzymes," J. Pharmacol. and Exper. Therap. 289(2):1112-1120, 1999.
Balboa, M. A. et al., "Novel group V phospholipase $A_2$ involved in arachidonic acid mobilization in murine P388D, macrophages," J. Biol. Chem. 271(50):32381-32384, 1996.
Benedetto, C., "Eicosanoids in primary dysmenorrheal, endometriosis and menstrual migraine," Gynecol. Endocrinol. 3:71-94, 1989.
Bernal, A. L. et al., "Are leukotrienes involved in human uterine contractility?" Br. J. Obstet. Gynaecol. 96:568-573, 1989.
Bieglmayer, C. et al., "Concentrations of various arachidonic acid metabolites in menstrual fluid are associated with menstrual pain and are influenced by hormonal contraceptives," Gynecol. Endocrinol. 9:307-312, 1995.
Hanasaki, K. et al., "Purified group X secretory phospholipase $A_2$ induced prominent release of arachidonic acid from human myeloid leukemia cells," J. Biol. Chem. 274(48):34203-34211, Nov. 26, 1999.
Nattero, G. et al., "Relevance of prostaglandins in true menstrual migraine," Headache 29:233-238, 1989.
Nigam, S. et al., "Increased concentrations of eicosanoids and platelet-activating factor in menstrual blood from women with primary dysmenorrheal," Eicosanoids 4:137-141, 1991.
Pisabarro, M. T. et al., "Rational modification of human synovial fluid phospholipase $A_2$ inhibitors," J. Med. Chem. 37:337-341, 1994.
Prigent, A. et al., "Prostaglandin $E_2$ production by uterine stromal cell line $U_{III}$: Regulation by estradiol and evidence of an ethanol action," Prostaglandins 47:451-466, 1994.
Rice, G. E., "Secretory type II phospholipase $A_2$ and the generation of intrauterine signals," Reprod. Fertil. Dev. 7:1471-1479, 1995.
Schevitz, R. W. et al., "Structure-based design of the first potent and selective inhibitor of human non-pancreatic secretory phospholipase $A_2$," Nat. Struct. Biol. 2(6):458-465, 1995.
Thunnissen, M. M. G. M. et al., "X-ray structure of phospholipase $A_2$ complexed with a substrate-derived inhibitor," Nature 347:689-691, 1990.

(Continued)

*Primary Examiner*—Taofiq Solola
(74) *Attorney, Agent, or Firm*—Greenlee Winner and Sullivan, P.C.

(57) ABSTRACT

The present invention relates generally to amino acid derivatives and to methods of making the same. In particular, the invention relates to compounds bearing a stereochemical identity, that is, the same stereochemistry, with the chiral α-carbon of D-α-amino acids and their use in methods of therapy, including the treatment of inflammatory diseases, and to compositions and enantiomeric mixtures containing them.

30 Claims, 2 Drawing Sheets

OTHER PUBLICATIONS

Zahradnik, H. P. et al., "Contribution to the pathogenesis of dysmenorrheal," Arch. Gynecol. 236:99-108, 1984.

J. Balsinde et al., *Regulation and Inhibition of Phospholipase $A_2$*, Annual Review of Pharmacology and Toxicology 39:175-190, Apr. 1999.

H. Beaton et al., *Discovery of New Non-Phospholipid Inhibitors of the Secretory Phospholipases $A_2$*, Chemical Abstract 120:238899, 1994.

H. Beaton et al., *Discovery of New Non-Phospholipid Inhibitors of the Secretory Phospholipases $A_2$*, J. Med. Chem. 37(5):557-559, 1994.

S.-S. Cha et al., *High-Resolution X-Ray Crystallography Reveals Precise Binding Interactions Between Human Nonpancreatic Secreted Phospholipase $A_2$ and a Highly Potent Inhibitor*, Chemical Abstract 125:241668, 1996.

S.-S. Cha et al., *High-Resolution X-Ray Crystallography Reveals Precise Binding Interactions Between Human Nonpancreatic Secreted Phospholipase $A_2$ and a Highly Potent Inhibitor (FPL67047XX)*, J. Med. Chem. 39(20):3878-3881, 1996.

E. Dennis, *The Growing Phospholipase $A_2$ Superfamily of Signal Transduction Enzymes*, TIBS 22:1-2, Jan. 1997.

A. Deveer et al., *Competitive Inhibition of Lipolytic Enzymes. VII. The Interaction of Pancreatic Phospholipase $A_2$ With Micellar Lipid/Water Interfaces of Competitive Inhibotors*, Chemical Abstract 117:65348, 1992.

A. Deveer et al., *Competitive Inhibition of Lipolytic Enzymes. VII. The Interaction of Pancreatic Phospholipase $A_2$ with Micellar Lipid/Water Interfaces of Competitive Inhibitors*, Biochimica Biophysica Acta 1125(1):73-81, 1992.

M. Garcia et al., *A Convenient Synthesis of 1-ether-2-acylamido-2-deoxy-sn-glycerophospholipids*, Chemical Abstract 120:245643, 1993.

M. Garcia et al., *A Convenient Synthesis of 1-ether-2-acylamido-2-deoxy-sn-glycerophospholipids*, Synthetic Communications 23(22):3165-3177, 1993.

H. Meyer et al., *Comparative Studies of Tyrosine Modification in Pancreatic Phospholipases. 2. Properties of the Nitrotyrosyl, Aminotyrosyl, and Dansylaminotyrosyl Derivatives of Pig, Horse, and Ox Phospholipases $A_2$ and Their Zymogens*, Chemical Abstract 91:104450, 1979.

H. Meyer et al., *Comparative Studies of Tyrosine Modification in Pancreatic Phospholipases. 2. Properties of the Nitrotyrosyl, Aminotyrosyl, and Dansylaminotyrosyl Derivatives of Pig, Horse, and Ox Phospholipases $A_2$ and Their Zymogens*, Biochemistry 18(16):3589-3597, 1979.

M. Murakami et al., *Different Functional Aspects of the Group II Subfamily (Types IIA and V) and Type X Secretory Phospholipase $A_2$s in Regulating Arachidonic Acid Release and Prostaglandin Generation*, J. Biol. Chem. 274(44):31435-31444, Oct. 29, 1999.

A. Ortiz et al., *Reliability of CoMFA Models: Effects of Data Scaling and Variable Selection Using a Set of Human Synovial Fluid Phospholipase $A_2$ Inhibitors*, Chemical Abstract 128:97306, 1997.

A. Ortiz et al., *Reliability of Comparative Molecular Field Analysis Models: Effects of Data Sealing and Variable Selection Using a Set of Human Synovial Fluid Phospholipase A2 INhibitors*, J. Med. Chem. 40:1138-1148, 1997.

A. Ortiz et al., *Reliability of CoMFA Models: Effects of Data Scaling and Variable Selection Using a Set of Human Synovial Fluid Phospholipase $A_2$ Inhibitors*, Additions and Corrections, J. Med. Chem. 40(25):4168, 1997.

W. Pruzanski et al., *Phospholipase $A_2$—A Mediator Between Proximal and Distal Effectors of Inflammation*, Immunology Today 12(5):143-146, 1991.

W. Yuan et al., *Synthesis of Sulfur-Substituted Phospholipid Analogs as Mechanistic Probes of Phospholipase A2 Catalysis*, Chemical Abstract 110:95663, 1989.

W. Yuan et al., *Synthesis of Sulfur-Substituted Phospholipid Analogues as Mechanistic Probes of Phospholipase $A_2$ Catalysis*, J. Org. Chem. 54(4):906-910, 1989.

R. C. Reid, "Inhibitors of secretory phospholipase A2 Group IIA," Current Medicinal Chemistry 12:3011-3026, 2005.

H. Bundgaard, "Design of prodrugs: Bioreversible derivatives for various functional groups and chemical entitles," In: Design of Prodrugs, H. Bundgaard (ed.), Elsevier Science Publishers, 1985, pp. 1-91.

K. A. Hansford et al., "D-Tyrosine as a chiral precursor to potent inhibitors of human nonpancreatic secretory phospholipase A2 (lla) with antiinflammatory activity," ChemBioChem 4:181-185, 2003.

* cited by examiner

Figure 1: Dixon plots for compounds (62),
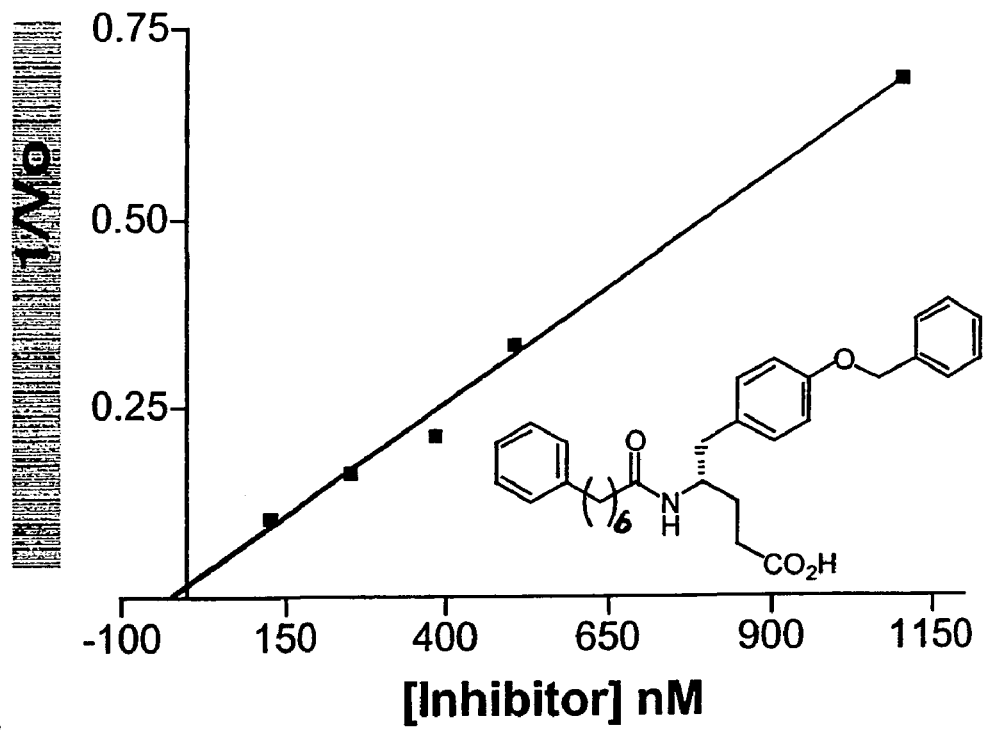
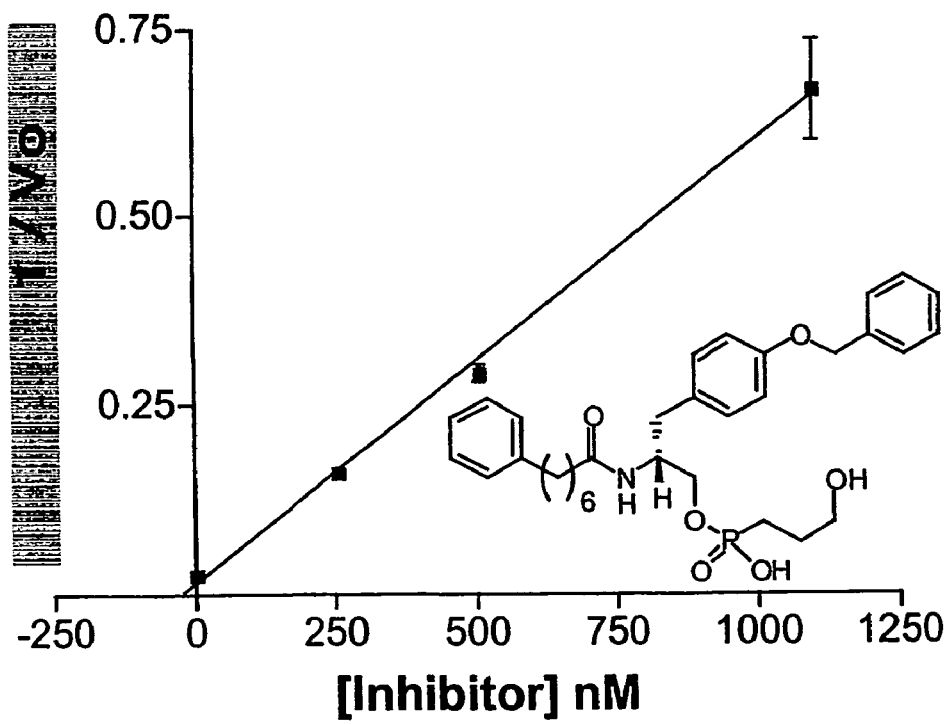

COMPOUNDS AND INHIBITORS OF PHOSPHOLIPASES

CROSS-REFERENCE TO RELATED APPLICATIONS

This application takes priority from PCT Application PCT/AU01/00898, filed 24 Jul. 2001, which takes priority from Australian Patent Application PQ8965/00, filed 24 Jul. 2000 and Australian Patent Application PR1669/00, filed 24 Nov. 2000.

FIELD OF THE INVENTION

The present invention relates generally to new inhibitors of secretory phospholipases A2 and to methods of making them. The invention discloses compounds that all bear a common chiral carbon atom attached to three different substititents that, in combination, provide (a) a calcium-binding chelating domain and (b) a hydrogen-bonding donor for the catalytic histidine of the enzyme (e.g. His48 in type IIa secretory phospholipase A2), and (c) from one to three hydrophobic moieties that occupy the substrate-biniding active site of the enzyme. In particular compounds of this invention have the same absolute configuration at their common chiral carbon atom. Many, though not all, of the compounds described can be derived simply from chiral precursors such as L- and/or D-amino acids, including uncommon and lipidic amino acids. Alternative synthetic methods can employ precursors that are not amino acids. Compounds of this invention can be used in the treatment of inflammatory diseases.

BACKGROUND

Human non-pancreatic secretory phospholipases A2 (sPLA2) are enzymes of 14 kD in size that effect ester hydrolysis of phospholipids at the sn-2 (or 2-acyl) position of 3-sn-phosphoglycerides to release a lysophospholipid and a fatty acid (ruzanski, W., et al, *Immunology Today,* 1991, 12, 143-146; Dennis, E. A., *Trends Biochem., Sci.,* 1997, 22, 1-2; Murakami, M., et al, *J. Biol. Chem.,* 274, 44, 31435-31444 Predominantly, the fatty acid released is arachidonic acid. When arachidonic acid is produced, it may be acted upon by other enzymes, including cyclooxygenases and lipoxygenases and transformed into inflammatory mediators such as platelet activating factor, prostalgandins, thromboxanes, lipoxins, lysophosphatides and leukotrienes (see Pnizanski supra). The presence of elevated levels of sPLA2 enzymes at sites of injury or inflammation has been demonstrated in a wide range of diseases and inflammatory conditions and the levels of enzyme activity have been correlated with the severity of the pathology (see Pruzanski supra). Compounds that inhibit the activity of sPLA$_2$ might therefore prevent the formation of inflammatory mediators and could potentially alleviate symptoms associated with inflammatory conditions.

There are at least nine published mammalian sPLA$_2$ enzymes including the human enzymes:—

| Type IB | pancreas |
|---|---|
| Type IIa | synoviocytes, platelets |
| Type IId | spleen |
| Type V | mast cell, macrophage, heart, lung |
| Type X | thymocytes, spleen, leukocytes |

Recently, abnormally high concentrations of human non-pancreatic secretory PLA$_2$-type IIa (hnpsPLA$_2$) were detected in synovial fluid of humans with rheumatoid arthritis and osteoarthritis, and in the blood of humans suffering from burns, sepsis, psoriasis, Crohn's disease, adult respiratory distress syndrome (ARDS), acute pancreatitis, bacterial peritonitis, asthma, malaria, atherosclerosis, cancer, pregnancy complications and post-operative states. In all cases, the severity of the disease strongly correlated with elevated sPLA$_2$ levels, suggesting a role for sPLA$_2$ in immune defence. Prolonged excessive sPLA$_2$ levels can, however, be deleterious, due to continuous eicosanoid formation and proteolytic activity. Intravenous administration of hnpsPLA$_2$ to rabbits, for example, produces symptoms of arthritis and sepsis.

It has also been shown that types IIa and V produce arachidonic acid from several sources and that endogenous substances, membrane disturbances and disease processes promote such cleavage. There is a growing body of work which suggests that a key finction of hnpsPLA$_2$ (type IIa) is an acute-phase protein, and a major bactericidal component of human tears, that helps eliminate infectious organisms and damaged host cells during the inflammatory response. Interestingly, it is also reported that this enzyme, which has quite a charged hydrophilic surface, normally has little activity in vitro on uncharged phosphatidylcholine vesicles and cell membranes. Mutation of residue 3 to the more hydrophobic residue Trp (Trp3) appears to increase binding by the PLA$_2$ to, and hydrolysis of, such lipid surfaces by 2-3 orders of magnitude, consistent with the notion that the indole side chain of Trp3 helps penetrate the lipid interface of membrane substrates. The interfacial characteristics and membrane processing rates of the Trp3 mutant of hnpsPLA$_2$ resemble those of mammalian pancreatic enzymes that also have a Trp at position 3. In addition to these surface effects on enzymatic function, very recently it has been proposed that some of the physiological functions that are regulated by sPLA$_2$ are mediated by specific interactions between PLA$_2$ surface residues and cellular receptors and, although there is evidence for this, the surface roles for PLA$_2$ are not at all clear. Thus, while enzymatic activity of hnpsPLA$_2$ is believed to stimulate neutrophils to produce superoxide, its surface properties are thought to be responsible for release of elastase and other degradative agents. To summarize, there is mounting evidence, therefore, that sPLA$_2$ enzymes participate extensively in regulating not just phospholipid digestion, but also both transcellular and intracellular conunications involved in diverse physiological functions as well as in disease development.

Purported inhibitors of various phospholipases A2, particularly non-humanPLA2 enzymes have been described. However, it is now recognised that difficulties associated with the assay methods previously used have led to many of these compounds incorrectly being attributed with the desired activity. Many of these compounds are now recognised as not being potent inhibitors and generally do not inhibit human non-pancreatic secretary PLA2 enzymes at submicromolar concentrations (Balsinde, *J., Ann, Rev. Pharmacol. Toxiol.,* 1999, 39, 175-89).

Thus, there exists a continued need for new inhibitors of sPLA2 which may be useful in the treatment of inflammatory diseases and conditions.

SUMMARY OF THE INVENTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

Surprisingly all of the compounds of the invention, which may act as inhibitors of sPLA2 (including types II, V and X), have the same absolute configuration at a common chiral carbon atom as defined in Formula (I) below.

Accordingly, in a first aspect, the present invention provides a compound of Formula (I):

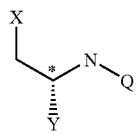

wherein

X is selected from the group consisting of:
CRR'CO₂H, CRR'-tetrazolyl, CRR'SO₃H, CRR'P(O)(OH)₂, CRR'P(O)(OH)(OR"), CHRCH₂CO₂H, CHRCH₂-tetrazolyl, CHRCH₂SO₃H, CHRCH₂P(O)(OH)₂, CHRCH₂P(O)(OH)(OR"), OP(O)(OH)R', NRSO₃H, NRP(O)(OH)₂, NRP(O)(OH)(OR")

wherein R, R' and R" are independently selected from hydrogen, optionally substituted alkyl, optionally substituted alkenyl, optionally substituted alkynyl, optionally substituted acyl, optionally substituted arylalkyl, optionally substituted cycloalk-ylalk-yl and optionally substituted heterocyclylalkyl, except that R" is not hydrogen;

Q is a group selected from formulae (a)-(g)

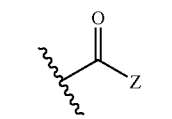
(a)

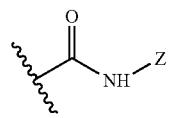
(b)

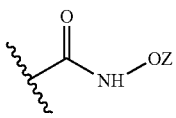
(c)

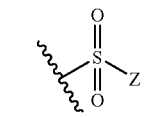
(d)

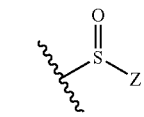
(e)

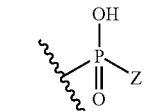
(f)

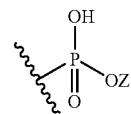
(g)

Y and Z are independently a group selected from formulae (i)-(iv):
(i) —(CH₂)$_m$-aa-(CH₂)$_n$—B; or
(ii) —(CH₂)$_m$-aa-(CH₂)$_n$-A-(CH₂)$_o$—B; or
(iii) —(CH₂)$_p$-A-(CH₂)$_q$-A'-(CH₂)$_r$—B
(iv) —(CH₂)$_s$—B wherein
m is 0 or 1, n, o, p, q and r are independently selected from 0 to 15 and s is from 5 to 15,
aa is an amino acid side chain residue;
A and A' are independently selected from O, S, NH, NR, NHC(O), NRC(O), CH₂, CHR, CHNH₂, C(O), C(O)O, C(O)NH, OC(O), and CH=CH, wherein R is selected from optionally substituted alkyl, optionally substituted alkenyl, optionally substituted alkynyl, optionally substituted aryl, optionally substituted cycloalkyl, optionally substituted heterocyclyl, optionally substituted arylalkyl, optionally substituted cycloalkylalkyl and optionally substituted heterocyclylalkyl; and
B is selected from, hydrogen, halogen, optionally substituted alkyl, optionally substituted alkenyl, optionally substituted alkynyl, optionally substituted aryl, optionally substituted heterocyclyl, optionally substituted cycloalk-yl, optionally substituted aryloxy, and optionally substituted heterocyclyloxy; optionally substituted cycloalk-yloxy, CO₂H;

wherein m, n, o, p, q, r, s, aa, A, A' and B are such that the longest continuous chain of atoms in a group of formula (i)-(iv) is from 5 to 15 atoms long; and wherein the compound of formula (I) has an IC₅₀ activity for inhibition of human non-pancreatic sPLA₂ at a concentration of 50 μM or less.

or salt, derivative or prodrug thereof.

Preferably the compound of formula (I) has an IC₅₀ activity for inhibition of human non-pancreatic sPLA2 at a concentration of 10 μM or less, more preferably 1 μM or less.

In a further aspect, the invention relates to a composition comprising a compound of Formula (I) or a salt, derivative or prodrug thereof together with a pharmaceutically acceptable diluent, excipient or carrier.

In yet another aspect, the invention relates to the use of a compound of formula (I) or a salt, derivative or prodrug thereof in the manufacture of a medicament for the treatment or prophylaxis of an inflammatory disease or condition.

The invention also relates to a method for the treatment or prophylaxis of an inflammatory disease or condition comprising the administration of a treatment or prophylactic effective amount of a compound of formula (I) or a salt, derivative or prodrug thereof to a subject in need thereof.

In another aspect, the present invention relates to the use of a D-α-amino acid in the preparation of a compound according to Formula (I). A further aspect of the invention relates to the use of L- or (DL)-α-amino acids in the preparation of a compound of Formula (I) and to the use of L- and (DL)-α-amino acids in the preparation of mixtures containing a compound of Formula (I).

The invention also relates to the use of non-amino acid precursors in the preparation of compounds of Formula (I).

Compounds of the invention may be substantially enantiomerically pure at the carbon centre bearing the Y substituent (*) or may be present in a enantiomeric mixture.

Thus further aspects of the invention relate to a enantiomeric mixture or racemate containing a compound of Formula (I), and the use of said mixture or racemate in methods of treatment or prophylaxis.

The invention also relates to the use of non-amino acid precursors in the preparation of D-, L- and (DL)-γ-amino acids subsequently used in the preparation of mixtures containing a compound of Formnula (I).

BRIEF DESCRIPTION OF THE FIGURES

FIG. 1 graphically depicts the extrapolated Dixon plot to give an $IC_{50}$ value for compounds (62) and (68)

DETAILED DESCRIPTION OF THE INVENTION

Figure 2:
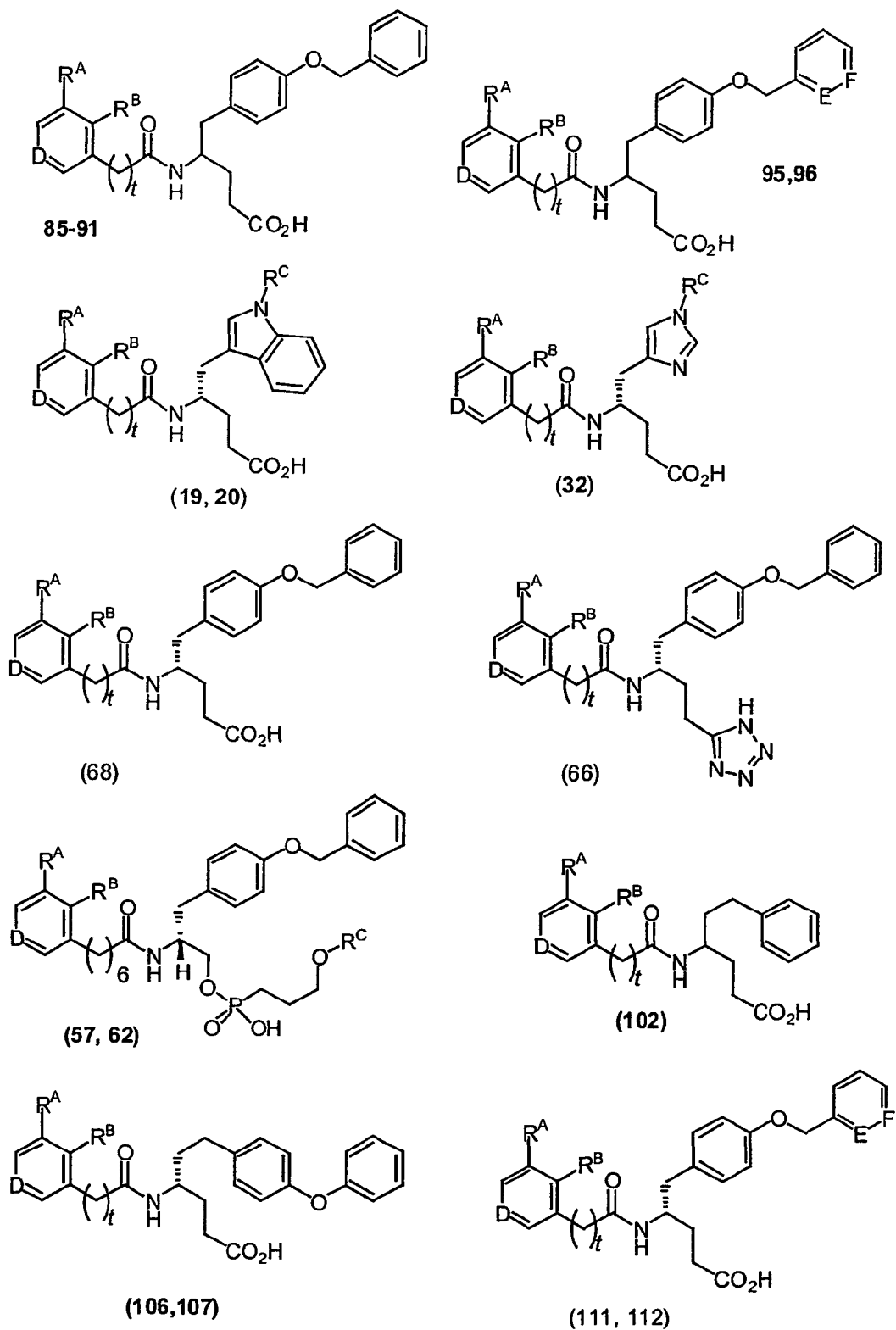
FIG. 2 depicts structural representations of a number of compounds of the invention.

The terms "salts", "derivatives" and "prodrugs" includes any pharmaceutically acceptable salt, ester, hydrate, or any other compound which, upon administration to the recipient, is capable of providing (directly or indirectly) a compound of the invention, or an active metabolite or residue thereof. Suitable pharmaceutically acceptable salts include salts of pharmaceutically acceptable inorganic acids such as hydrochloric, sulphuric, phosphoric, nitric, carbonic, boric, sulfamic and hydrobromic acids, or salts of pharmaceutically acceptable organic acids such as acetic, propionic, butyric, tartaric, maleic, hydroxymaleic, funaric, citric, lactic, mucic, gluconic, benzoic, succinic, oxalic, phenylacetic, methanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylanmonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

However, it will be appreciated that non-pharmaceutically acceptable salts also fall within the scope of the invention since these may be useful in the preparation of pharmaceutically acceptable salts. The preparation of salts and prodrugs and derivatives can be carried out by methods known in the art. For example, metal salts can be prepared by reaction of a compound of the invention with a metal hydroxide. An acid salt can be prepared by reacting an appropriate acid with a compound of the invention.

The compounds of the invention may be in crystalline form either as the free compounds or as solvates (e.g. hydrates) and it is intended that both forms are within the scope of the present invention. Methods of solvation are generally known within the art.

Any compound that is a prodrug of a compound of formula (I) is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

As used herein, the term "alkyl", when used alone or in words such as "arylalkyl", "heterocyclylalkyl" and "cycloalkylalkyl", denotes straight chain or branched hydrocarbon residues, preferably $C_{1-20}$ alkyl, eg $C_{1-10}$ or $C_{1-6}$. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. An alkyl group may be optionally substituted by one or more optional substitutents as herein defined. Accordingly, "alkyl" as used herein is taken to refer to optionally substituted alkyl.

"Cycloalkyl" when used alone or in compound words such as "cycloalkoxy", refers to cyclic hydrocarbon residues, including mono- or polycyclic alkyl groups. Preferred cycloalkyl are $C_{4-7}$ alkyl. A "cycloalkyl" group may contain one or more double or triple bonds to form a cycloalkenyl or cycloalkynyl group and accordingly, "cycloalkyl" also refers to non-aromatic unsaturated as well as saturated cyclic hydrocarbon residues. Examples of "cycloalkyl" include cyclopropyl, cyclobutyl, cyclopentyl, cyclohexyl, cyclolheptyl, cyclooctyl, cyclononyl, cyclodecyl, 1,3-cyclohexadienyl, 1,4-cyclohexadienyl, 1,3-cycloheptadienyl, 1,3,5-cycloheptatrienyl and 1,3,5,7-cyclooctatetraenyl. A cycloalkyl group may be optionally substituted by one or more optional substitutents as herein defined. Accordingly, "cycloalkyl" as used herein is taken to refer to optionally substituted cycloalkyl.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{1-20}$ alkenyl (eg $C_{1-10}$ or $C_{1-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, and 1,4-hexadienyl. An alkenyl group may be optionally substituted by one or more optional substitutents as herein defined. Accordingly, "alkenyl" as used herein is taken to refer to optionally substituted alkenyl.

The term "alkynyl" denotes groups formned from straight chain or branched hydrocarbon residues containing at least one carbon to carbon triple bond including ethynyically mono-, di- or poly-unsaturated alkyl or cycloalkyl groups as previously defined, preferably $C_{1-20}$ alkynyl (for example $C_{1-10}$ or $C_{1-6}$). Examples, include ethynyl, propynyl, butynyl, pentynyl. An alkynyl group may be optionally substituted by one or more optional substitutents as herein defined. Accordingly, "alkynyl" as used herein is taken to refer to optionally substituted alkynyl.

The term "aryl" used either alone or in compounds words such as "arylalkyl" and "aryloxy", denotes single, polynuclear, conjugated or fused residues of aromatic hydrocarbons. Examples of aryl include phenyl, biphenyl and naphthyl. Preferred aryl groups include phenyl and naphthyl. An aryl group may be optionally substituted by one or more optional substitutents as herein defined. Accordingly, "aryl" as used herein is taken to refer to aryl that may be optionally substituted, such as optionally substituted phenyl and optionally substituted naphthyl.

The term "heterocyclic" or "heterocyclyl" or "heterocycle", used either alone or in compound words such as "heterocyclylalkyl" or "heterocyclyloxy" denotes single, polynuclear, conjugated or fused carbocyclic groups wherein at least one carbon atom is replaced by a heteroatom, preferably selected from the group of nitrogen, sulphur and oxygen. Where two or more carbon atoms are replaced, this may be by two or more of the same heteroatom or by different heteroatoms. The heterocyclic group may be aromatic or non-aromatic. An aromatic heterocyclyl group may also be referred to as "heteroaryl". A heterocyclic group may be optionally substituted by one or more optional substitutents as herein defined. Accordingly, "heterocyclic" or "heterocyclyl" or "heterocycle" as used herein is taken to refer to heterocyclyl or heterocyclyl or heterocycle that may be optionally substituted. Preferred "heterocyclic", "heterocyclyl" or "heterocycle" include 5-6-membered groups, particularly nitrogen containing groups.

Examples of heterocyclic groups include N-containing heterocyclic groups, such as, unsaturated 3 to 6 membered heteromonocyclic groups containing 1 to 4 nitrogen atoms, for example, pyrrolyl, pyrrolinyl, imidazolyl, imidazolinyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidyl, pyrazolidinyl or piperazinyl;

condensed saturated or unsaturated heterocyclic groups containing 1 to 5 nitrogen atoms, such as, indolyl, isoindolyl, indolinyl, isoindolinyl, indolizinyl, isoindolizinyl, benzimidazolyl, quinolyl, isoquinolyl, indazolyl, benzotriazolyl, purinyl, quinazolinyl, quinoxalinyl, phenanthradinyl, phenatbrolinyl, phthalazinyl, naphthyridinyl, cinnolinyl, pteridinyl, perimidinyl or tetrazolopyridazinyl;

saturated 3 to 6-membered heteromonocyclic groups containing 1 to 3 oxygen atoms, such as tetrahydrofuranyl, tetrahydropyranyl, tetrahydrodioxinyl, unsaturated 3 to 6-menibered hetermonocyclic group containing an oxygen atom, such as, pyranyl, dioxinyl or furyl;

condensed saturated or unsaturated heterocyclic groups containing 1 to 3 oxygen atoms, such as benzofuranyl, chromenyl or xanthenyl;

unsaturated 3 to 6-membered heteromonocyclic group containing 1 to 2 sulphur atoms, such as, thienyl or dithiolyl;

unsaturated 3 to 6-membered heteromonocyclic group containing 1 to 2 oxygen atoms and 1 to 3 nitrogen atoms, such as, oxazolyl, oxazolinyl, isoxazolyl, furazanyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl, thiazolinyl saturated 3 to 6-membered heteromonocyclic group containing 1 to 2 sulphur atoms and 1 to 3 nitrogen atoms, such as, thiazolidinyl, thiomorphinyl; and unsaturated condensed heterocyclic group containing 1 to 2 sulphur atoms and 1 to 3 nitrogen atoms, such as, benzothiazolyl or benzothiadiazolyl.

The terms "aryloxy", "cycloalkyloxy" and "heterocyclyloxy" denote aryl, cycloalkyl and heterocyclyl groups respectively, when linked by an oxygen atom.

The terms "arylalkyl", "cycloalkylalkyl" and "heterocyclylalkyl" refer to an alkyl group substituted (preferably terminally) by an aryl, cycloalkyl or heterocyclyl group respectively The term "acyl" denotes a group containing the moiety C═O (and not being a carboxylic acid, ester or amide or thioester). Preferred acyl includes C(O)—R, wherein R is hydrogen or an alkyl, alkenyl, alkynyl, aryl, cycloalkyl, heterocyclyl, arylalkyl, cycloalkylalkyl or heterocyclylalkyl residue, preferably a $C_{1-20}$ residue. Examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; phenylcarbonyl; cycloalkylcarbonyl such as cyclopropylmethyl(or ethyl)carbonyl cyclobutylmethyl(or ethyl)carbonyl, cyclopentylmethyl(or ethyl)carbonyl and cyclohexylmethyl (or ethyl)carbonyl; aralkanoyl such as phenylalkanoyl (for example phenylacetyl, ie benzoyl, phenylpropanoyl, phenylbutanoyl, phenylpentanoyl and phenylhexanoyl) and naphthylalkanoyl (for example naphthylacetyl, naphthylpropanoyl and naphthylbutanoyl).

The term "halogen" refers to fluorine, chlorine, bromine or iodine.

Groups such as alkyl, alkenyl, alkynyl, aryl, and heterocyclyl, whether used alone or in a compound word or in the definition of a group may be optionally substituted by one or more substitutents. In this specification "optionally substituted" means that a group may or may not be further substituted with one or more groups selected from alkyl, alkenyl, alkynyl, aryl, halo, haloalcyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalk-enyl, nitroalkynyl, nitroaryl, nitroheterocyclyl, amino, alkylamino, dialkylamino, alkenylarnino, alkynylamino, arylamino, diarylamino, phenylamino, diphenylamino, benzylamino, dibenzylamino, hydrazino, acyl, acylamino, diacylamino, acyloxy, heterocyclyl, heterocycloxy, heterocyclamino, haloheterocyclyl, carboxy ester, carboxy, carboxy anmide, mercapto, alk-ylthio, benzylthio, acylthio and phosphorus-containing groups. As used herein, the term "optionally substituted" may also refer to the replacement of a $CH_2$ group with a carbonyl (C═O) group Preferred optional substituents include alkyl, preferably $C_{1-8}$ aLkyl (for example $C_{1-6}$alkyl such as methyl, ethyl, propyl, butyl, cyclopropyl, cyclobutyl, cyclopentyl or cyclohexyl), hydroxy $C_{1-8}$ alkyl (for example hydroxymethyl, hydroxyethyl, hydroxypropyl), alkoxyalkyl (for example methoxymethyl, methoxyethyl, methoxypropyl, ethoxymethyl, ethoxyethyl, ethoxypropyl etc) $C_{1-8}$ alkoxy, (for example $C_{1-6}$ alkoxy such as methoxy, ethoxy, propoxy, butoxy, cyclopropoxy, cyclobutoxy), halo (fluoro, chlioro, bromo, iodo), trifluoromethyl, trichloromethyl, tribromomethyl, hydroxy, phenyl (which itself may be further substituted, by an optional substitutent as described herein, for example, hydroxy, halo, methyl, ethyl, propyl, butyl, methoxy, ethoxy, acetoxy, amino), benzyl (wherein the $CH_2$ and/or phenyl group may be further substituted as described above), phenoxy (wherein the $CH_2$ and/or phenyl group may be further substituted as described above), benzyloxy (wherein the $CH_2$ and/or phenyl group may be further substituted as described above), amino, $C_{1-8}$ alkylamino (eg $C_{1-6}$alkyl, such as methylamino, ethylamino, propylamino), di $C_{1-8}$ alkylamino (for example $C_{1-6}$alkyl, such as dimethylamnno, diethylamino, dipropylamino), acylamino (for example $NHC(O)CH_3$), phenylamino (wherein phenyl itself may be further substituted as described above), nitro, formyl, —C(O)—$C_{1-8}$ alkyl (eg $C_{1-6}$ alkyl, such as acetyl), O—C(O)-alkyl (for example $C_{1-6}$alkyl, such as acetyloxy), benzoyl (wherein the $CH_2$ and/or phenyl group itself may be further substituted of $CH_2$ with C=O, $CO_2H$, $CO_2$ $C_{1-8}$ alkyl (for example $C_{1-6}$ alkyl such as methyl ester, ethyl ester, propyl ester, butyl ester), $CO_2$phenyl (wherein phenyl itself may be further substituted), $CONH_2$, CONHphenyl (wherein phenyl itself may be further substituted as described above), CONHbenzyl (wherein the $CH_2$ and/or phenyl group may be further substituted as described above), CONH $C_{1-8}$ alkyl (for example $C_{1-6}$ alkyl such as methyl amuide, ethyl amide, propyl amide, butyl amide), CONHdi $C_{1-8}$ alkyl (for example $C_{1-6}$alkyl).

In one preferred embodiment of the invention, Q is a group of formula (a).

In another preferred form of the invention where X contains the moiety CRR'—, R' is hydrogen with R as hereinbefore defined, ie both R and R' can be hydrogen or just R' can be hydrogen. Particularly preferred X are selected from the group consisting of: $CH_2CO_2H$, $CHRCO_2H$, $CH_2$-tetrazolyl, CHR-tetrazolyl, $CH_2SO_3H$, $CHRSO_3H$, $CH_2P(O)(OH)_2$, $CH_2P(O)(OH)(OR")$, $CHRP(O)(OH)_2$, $CHRP(O)(OH)(OR")$, $CH_2CH_2CO_2H$, $CHRCH_2CO_2H$, $CH_2CH_2$-tetrazolyl, $CHRCH_2$-tetrazolyl, $CHCH_2SO_3H$, $CHRCH_2SO_3H$, $CH_2CH_2P(O)(OH)_2$, $CH_2CH_2P(O)(OH)_2$ $CHRCH_2P(O)(OH)_2$, $CH_2CH_2P(O)(OH)(OR")$, $CHRCH_2P(O)(OH)(OR")$ and $OP(O)(OH)R'$.

In a more preferred form of X, R and R' are independently selected from alkyl, arylalkyl, cycloalkylalkyl and heterocyclylaLkyl (where alkyl is a $C_{1-15}$alkyl or a $C_{1-15}$alkylene chain as appropriate) each of which may be substituted or unsubstituted. Examples include $C_{1-15}$alkyl, $C_{4-7}$cycloalkylalkyl, benzyl, phenylethyl, phenylpropyl, phenylbutyl, phenylpentyl, phenylhexyl, pyridylmethyl, pyridylethyl, hydroxyalkyl, alkoxyalkyl and arylalkyloxyalkyl.

In another embodiment of the invention, Y is a group of formula (i) or (ii). Preferred aa include the side chain residues from amino acids such as Histidine, Tryptophan, Senine, Tyrosine, Cysteine, Threonine, Glutamic acid, Aspartic acid, Lysine, Arginine, β-Alanine, Ornithine, Phenylalanine, Glutamine, and their homo derivatives. In this embodiment, m is 0 or 1 and n can be independently 0 or 1 or 2 or 3 or 4 or 5. In one preferred form, m+n is at least 5. A particularly preferred Y group is derived from homotyrosine or tyrosine or tryptophan or histidine.

Exemplary aa groups and, where appropriate, possible alternative points of attachment, are illustrated below. Group 1 illustrates aa groups and their theoretical starting amino acids where m=0. Group 2 illustrates a number of corresponding homo-D-amino acids.

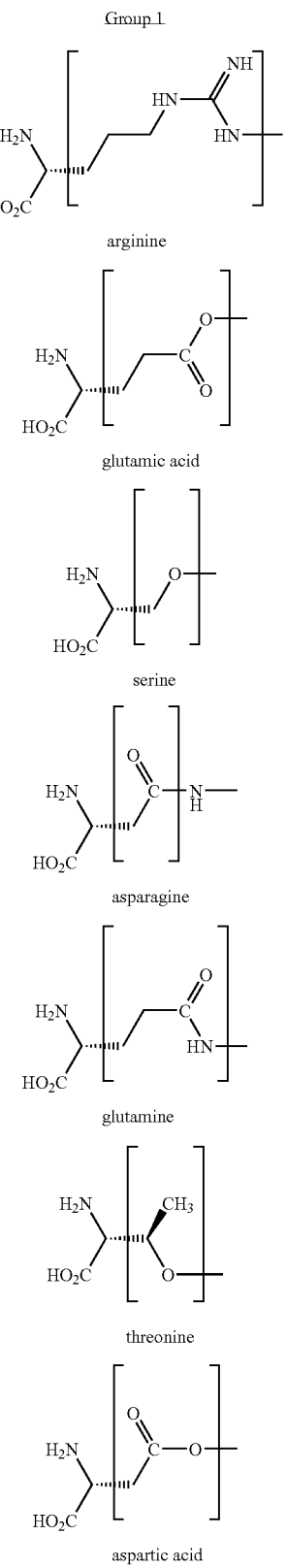

-continued
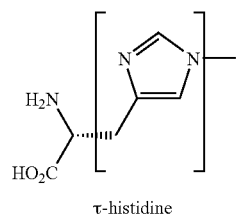
τ-histidine
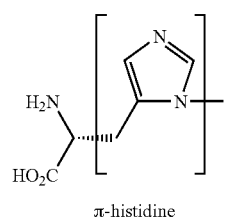
π-histidine
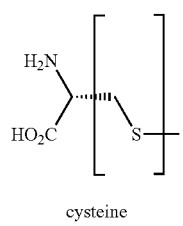
cysteine
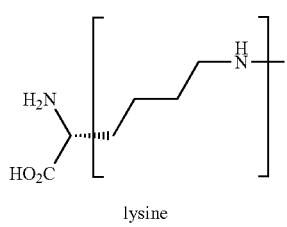
lysine
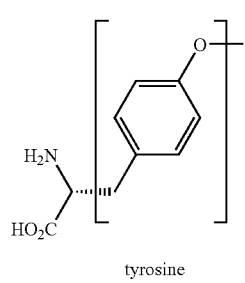
tyrosine
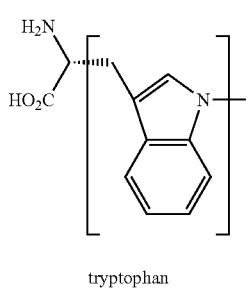
tryptophan
[ ] = "aa"
Group 2
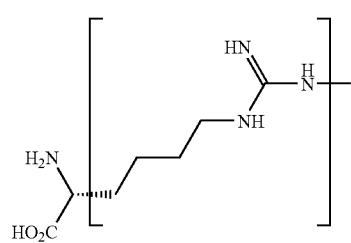
homoarginine
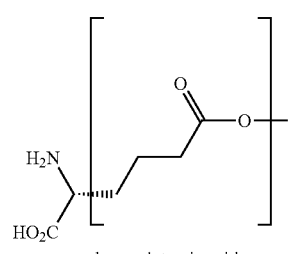
homoglutamic acid
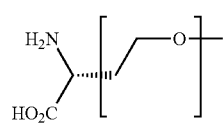
homoserine
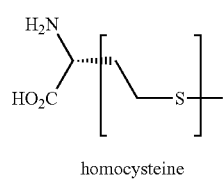
homocysteine
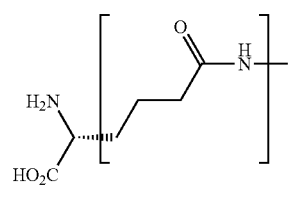
homoglutamine
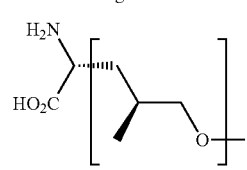
homothreonine
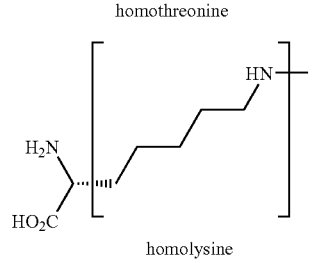
homolysine

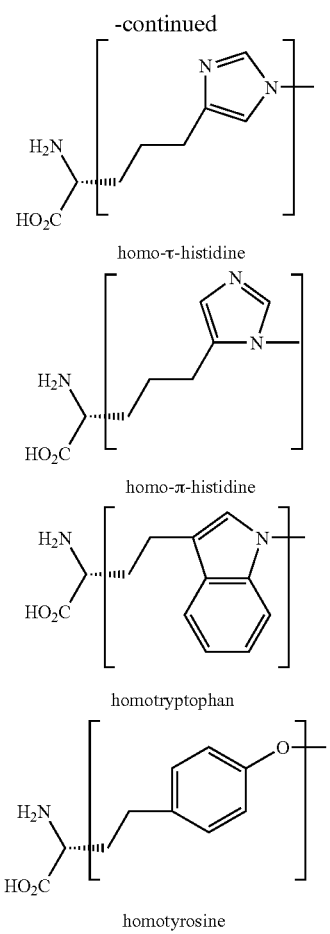

homo-τ-histidine homo-π-histidine homotryptophan homotyrosine

[ ] = "aa"

In another preferred embodiment, B is selected from optionally substituted $C_{4-7}$ cycloalkyl (cyclobutyl, cyclopentyl, cyclohexyl and cycloheptyl) optionally substituted phenyl or an optionally substituted 5- or 6-membered heterocyclyl group, such as pyridyl, pyridazinyl, pyrimidinyl, pyrazinyl etc.

Preferred Y include:
a) $(CH_2)_m$-aa-$(CH_2)_n$—B
  wherein m is 0 or 1
  n is 0, 1, 2, or 3
  aa is an amino acid side chain residue from an amino acid selected from the group consisting of arginine, glutamic acid, serine, asparagine, glutamine, threonine, aspartic acid, histidine, cysieine, lysine, tyrosine, tryptophan, β-alanine, ornithine and phenylalanine B is a phenyl group, a 5-6-membered heterocyclyl group or a $C_5$-$C_6$ cycloalkyl group each of which may be substituted or unsubstituted; and
b) $(CH_2)_v$—B
  wherein v is 2-7 and B is as above.

Preferably Z is a chain of formula (iii) or (iv).

In another preferred form of the invention Z a group of formula (iii) wherein A and A' are independently CH=CH or $CH_2$. Preferably, Z is a chain of from 6 to 11 atoms in length. Thus, in a preferred from of the invention, Z is a alkyl chain of 6 to 11 carbon atoms or an alkenyl chain or from 6 to 11 carbon atoms, having one or two double bonds. In another form of the invention, one, of A or A' is O or S while the other is $CH_2$ or CH=CH. In a particularly preferred form of this embodiment, B is an optionally substituted phenyl or 5- or 6-membered heteroaryl ring. In a more preferred form of the invention, Z is a group of formula (iii) wherein A and A' are independently $CH_2$ or CH=CH, so as to form a $C_5$-$C_7$, preferably $C_6$, alkyl or alkenyl (having one or two double bonds) chain terminated by an optionally substituted phenyl or optionally substituted 5- or 6-membered heterocyclyl ring or optionally substituted 5- or 6-membered cycloalkyl ring.

A preferred group of compounds have formula (1A)

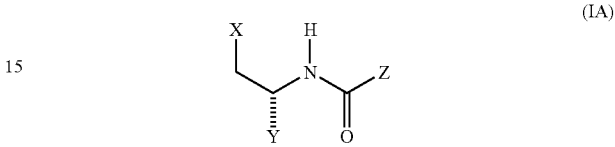

(IA)

wherein X is $CRR'CO_2H$ or $CHRCH_2CO_2H$, Y is a group of any one of Formula (i)-(iv) and Z is a group of Formula (iii) or (iv).

In one embodiment of the present invention there is provided small molecule inhibitors of phospholipase which are generally characterized by the following chemical properties; comprise a carbonyl oxygen and a carboxylate oxygen for the chelation to calcium; comprise an amide NH for hydrogen bonding to the active site of any phospholipase; comprise a chiral carbon alpha to the amide nitrogen; comprise two aliphatic/aromatic segments each of 8-15 carbon atoms attached to the calcium binding domain of the inhibitor; and have a hydrophobic nature with Log $P_{o/w}$ ratios from about 1 to 7.

When calculating the length of the Y and Z groups, the number of carbon and heteroatoms atoms linked in a continuous chain are counted. Counting of the chain length for Y starts inclusively at the first atom of Y directly attached to the chiral (*) carbon. Counting of the chain length for Z starts inclusively at the first atom of Z attached directly to, where appropriate: the carbonyl carbon of (a), the nitrogen atom of (b), the oxygen atom attached to the nitrogen atom of (c), the sulfur atom of (d) or (e), the phospohorus atom of (f) or the singly bonded oxygen atom attached to phosphorous atom of (g). For example:

—$CH_2$—, —O—, —S—, —NH— and —C(O)— groups are taken to equal 1 atom where a cyclic group, whether monocyclic or fused polycyclic, is in the middle of a chain Y or Z, ie it is linked in the chain at two positions, the number of atoms is counted as being the least number of carbon atoms or heteroatoms between the two bonds which link the cyclic group within the chain ortho- (1,2-) or meta- (1,3-) linked 6-membered aryl or heteroaryl groups (whether monocyclic or fused to another ring) are taken to equal 2 or 3 atoms respectively; para- (1,4-) linked 6-membered aryl or heteroaryl groups (whether monocyclic or fused to another ring) are taken to equal 4 atoms 1,3-linkages through a 5-membered ring, for example, the indole group of a tryptophan side chain or a 1,2 linkage through a imidazole group of a histidine side chain are taken to equal 3 and 2 atoms respectively.

where Y and Z are terminated by a cyclic group, the chain is counted as being terminated at the carbon atom or heteroatom the firrtherst number of atoms from the point of linkage of the cyclic group to the remainder of the chain, eg an unsubstituted 6-membered ring (such as phenyl or pyridyl) at the terminus of the chain is counted as 4 atoms; or a para-methyl substituted phenyl group at the terminus of the chain is counted as 5 atoms.

The compounds of the invention possess the stereochemistry of the carbon designated * in Formula (I), such that the Y group is of the same stereochemistry is of the same stereochemistry as the carbon designated * as an R side chain of a D-amino acid as depicted below.

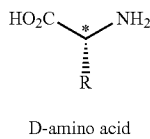

D-amino acid

Some of the compounds of the invention can therefore be synthesised from a suitable D-α-amino acid by a process comprising 3 steps; (a) derivatising the amino acid side chain to form the group Y; (b) extension of the C-terminus of the amino acid to from the group X; and (c) appropriate derivatisation of the amino terminus to form the group Q. It will be recognised that these steps may be carried out in any appropriate order. This forms a further aspect of the invention. The invention also relates to compounds of formula (I) prepared from a suitable D-α-amino acid by any one of steps a), b) or c) as described above.

While some of the compounds of the invention can be prepared from a suitable starting D-α-amino acid, it will be recognised that other methods known in the art for preparing amino acids may also be suitable, for example coupling of an amine and a carboxylic acid under suitable conditions such as by the use of a coupling agent. Compounds of the invention may also be obtained from L-α-amino acids (and reversing the optical rotation) and mixtures of D/L-α-amino acids.

Enantiomeric mixtures (that is, D/L mixtures, for example those obtained by coupling an amine and an acid) may be resolved by conventional methods, for example, chromatography or the use of a resolving agent to provide compounds of formula (I). The invention thus also relates to compounds of formula (I) in pure or substantially pure isomeric (enantiomeric) form at the carbon centre bearing the Y substituent, (*) for example, greater than about 90% enantiomeric excess (ee), such as 95 or 97% ee, preferably greater than 99% ee, as well as mixtures (including racemic nixtures) thereof. The invention therefore also provides mixtures isomeric at C* of formula (I).

In order to carry out the steps and processes described above, it will be recognised that it may be necessary to temporarily protect reactive groups such as the carboxylic acid and amino tenninii. Suitable protecting groups for these are knowvn in the art and are described in, for example, *Protective Groups in Organic Synthesis*, T. W. Greene and P. Wutz, John Wiley and Son, 3$^{rd}$ Edition, (1999). Exemplary protecting groups include Boc (t-butoxycarbonyl) for amino, and conversion of the carboxylic group to a suitable ester, eg benzyl esters. The protecting groups may be removed at an appropriate stage using standard procedures also described in Green and Wutz supra.

The preparation of compounds where X=CH$_2$CO$_2$H can generally be prepared by reducing a suitably amino protected or amino substituted D-amino acid via it's Weinreb amide [Nahm, S., and Weinreb, S. M., *Tetrahedroni Lett.*, 1981, 22, 3815] to the corresponding aldehyde (I) (Scheme A).

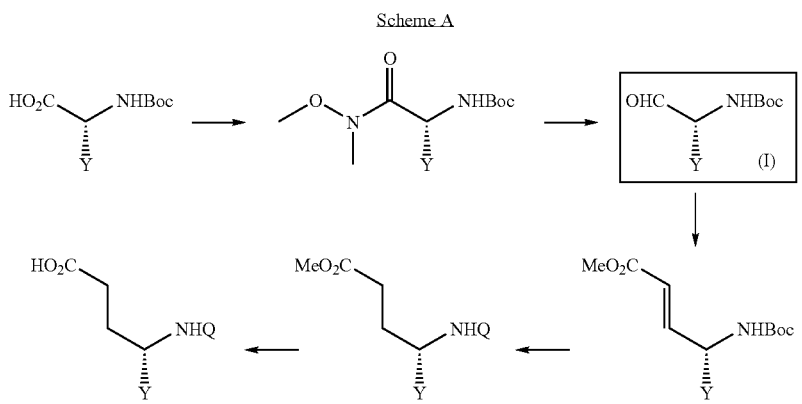

Wittig homologation of (I) with a stabilized phosphorane yields the α,β-unsaturated ester which after substitution with Q, can be transformed via hydrogenation and ester hydrolysis to the target acid.

Compounds where X=CHRCO$_2$H can be approached via the same aldehyde (I), using an appropriately substituted phosphorane eg (Ph$_3$P=C(R)CO$_2$Me), and hydrogenation as before (Scheme B). Where one enantiomer from the hydrogenation is required, the process can be conducted in a selective manner by employing one of several selective procedures described in the general literature (Hudlicky, M., *Reductions in Organic Chemistry*, 2$^{nd}$ Edition, ACS Monograph, Washington, 1996, pp 15-17). Alternatively, enantiomers may be separated using suitable chromatographic techniques.

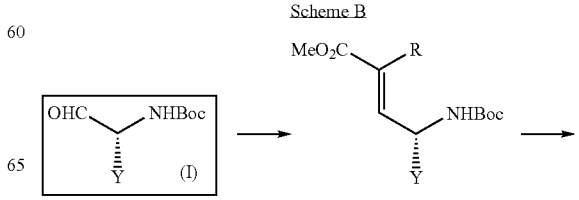

-continued

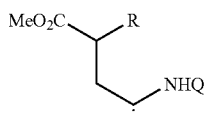

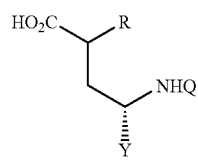

Phosphonic acid analogues (X=P(O)(OH)$_2$ and P(O)(OH)(OR)) of the above compounds may be readily prepared by Hunsdiecker reaction [Wilson, *Org. Reactions*, 9, 332-388 (1957); Malachowski, W. P., and Coward, J. K., *J. Org. Chem.*, 1994, 59, 7625] of the above acids, to the corresponding alkyl bromide, followed by Arbuzov conversion to the desired phosphonate ester. [Arbuzov, *Pure Appl Chem.*, 9, 307-355 (1964); Malachowski, W. P., and Coward, J. K., *J. Org. Chem.*, 1994, 59, 7625 and Bhattacharya, A. K., and Thyagarajan, G., *Chem. Rev.*, 1981, 81, 415] (Scheme C, wherein R can be H or R" as hereinbefore defined).

Scheme C

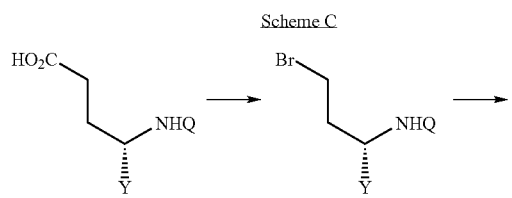

-continued

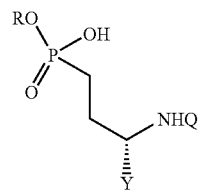

Sulfonic acid analogues of the above compounds (X=CH$_2$SO$_3$H) may also be prepared from the Hunsdiecker product alkyl bromide, followed by sulfonation with sulfite ion [Gilbert, *"Sulfonation and Related Reactions" pp* 136-148, 161-163 Interscience Publishers, New Yorl (1965), Trice, W. E., and Hoerger, F. D., *J. Am. Chem. Soc.*, 1955, 77, 2496] (see for example Scheme D).

Scheme D

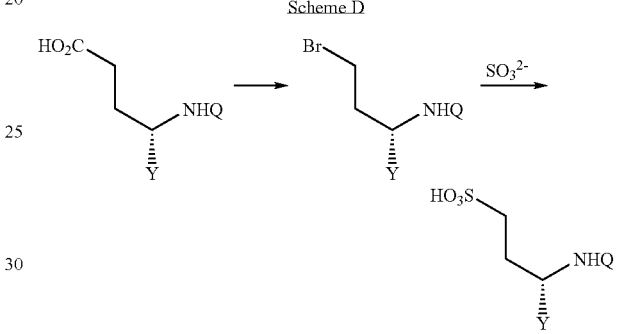

Phosphonate analogues of the above compounds (eg X=OP(O)(OH)R") which bear an additional R group that can act as a binding arm in the enzyme pocket may be prepared by reduction of the intermediate aldehyde (I) to the corresponding alcohol, followed by coupling with an appropriately substituted phosphonochloridate (eg MeOP(O)ClR),. [Lin, H-K and Gelb, M. H., *J. Am. Chem. Soc.*, 1993, 115, 3932] (Scheme E). Hydrolysis of corresponding phosphonate methyl ester (for example with tert-butylamine) [Ikeda, S., Weinhouse, M. I., Janda, K. D., and Lerner, R. A., *J. Am. Chem. Soc.*, 1991, 113, 7763] can afford access to the compounds of formula (I) (Scheme E).

Scheme E

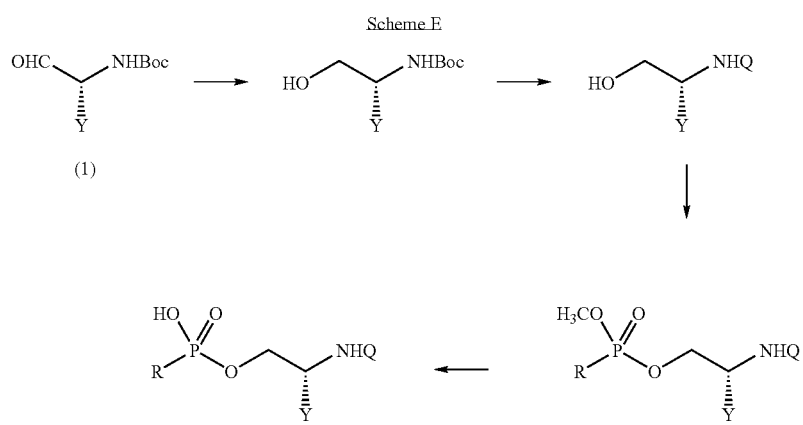

5-Substituted tetrazole derivatives of the above compounds are readily available by further elaboration of the target acid described in Scheme A. Conversion of the acid into the amide followed by dehydration yields the corresponding nitrile, (Scheme F). The tetrazole is then formed by reaction of the nitrile with NaN₃/Et₂NH.HCl. [Lee, D., Marshall, L. A., Bolognese, B., and Adams, J. L., *Bioorg. Med. Chem. Lett.*, 1997, 7, 1427].

Scheme F

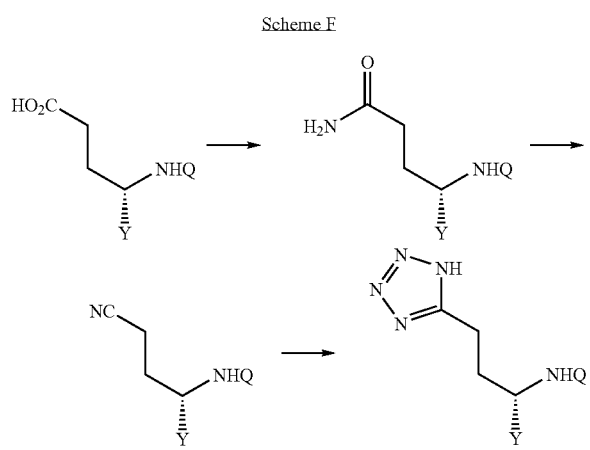

Incorporation of a further methylene chain to provide access to X groups such as $CH_2CH_2CO_2H$, $CHRCH_2CO_2H$, $CH_2CH_2SO_3H$, $CHRCH_2SO_3H$, $CH_2CH_2P(O)(OH)_2$, $CHRCH_2P(O)(OH)_2$ etc can be achieved by art known methods such as Arndt-Eistert synthesis. By this means an acid chloride can be converted to a carboxylic acid with the insertion of $CH_2$. Thus a suitably protected D-amino acid can be converted to an acid chloride by treatment with thionyl chloride. The acid chloride derivative can be reacted with diazomethane to form the diazoketone which can then be treated with $Ag_2O/H_2O$ or silver benzoate and triethylamine to form —$CH_2CO_2H$. The resulting acid can be treated as described above to provide access to phosphonic acids, sulfonic acids etc.

Sulfamic ($X=NRSO_3H$) acid compounds may be prepared from the parent amine (Scheme G), which is accessible via either direct amidation-reduction of an amino acid, or reductive amination of the key aldehyde (1). The amine is treated with either chlorosulfonic acid [Audrieth, L. F., and Sveda, M., *J. Org. Chem.*, 1944, 9, 89] or pyridine-sulfur trioxide complex [Warner, D. J., and Coleman, L. C., *J. Org. Chem.*, 1958, 23, 1133] to yield the target compound.

Scheme G

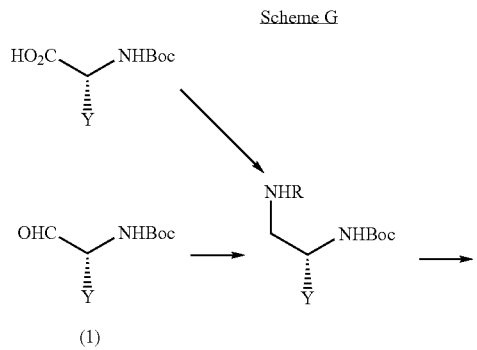

-continued

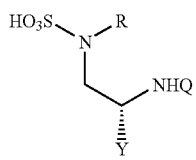

Phosphoramic acids ($X=NRP(O)(OH)_2$) and phosphoramidates ($X=NRP(O)(OH)(OR'')$) may be prepared via the amine described above plus a dialkylphosphoryl chloride (Scheme H) [Wang, M., Liu, S., Liu, J., and Hu, B,. *J. Org Chem.*, 1995, 60, 7364; Mungall, W. S. et al, *J. Org. Chem.*, 1975, 40, 1659], or an amine+H-phosphonate [Tomoskozi, I., Gacs-Baitz, E., and Otvos, L, *Tetrahedron*, 1995, 51, 6797] reaction.

Scheme H

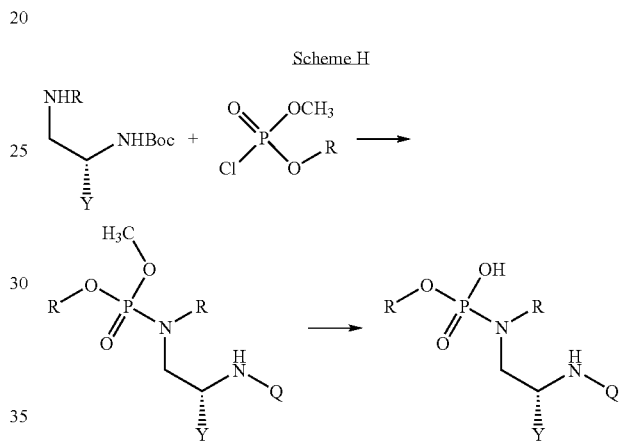

The coupling of the component Q to the amino group of the γ-amino acid component is illustrated in Scheme I. In the illustrated example the N-terminus is protected by a N-tert-butoxycarbonyl (Boc) group, however other nitrogen protecting groups compatible with the earlier chemistry may be included [Green, T. W. and Wuts, P. G. M, *Protective Groups in Orgainic Chemistry*, (1999)]. The protecting group is removed by standard methodology, and the coupling procedure is perfonned as described in the following section.

Scheme I

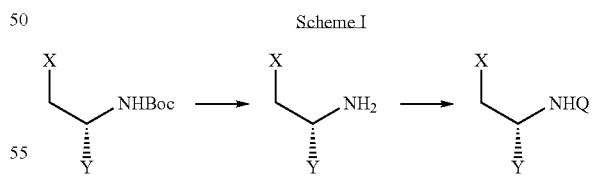

Where Q is of the formula (a), the coupling reaction is typically an amine+acid reaction giving a carboxamide product (Scheme J). The illustrated example is the reaction with 7-phenylheptanoic acid activated as the HOBT ester which may be obtained using BOP, PyBOP, HBTU or TBTU reagents [Bodansky, M.; Bodansky, A. *The Practice of Peptide Synthesis*; Springer-Verlag: Berlin, 1994], Alternatively, where appropriate, acyl chlorides or carbodiimide coupling reagents may be employed.

Scheme J

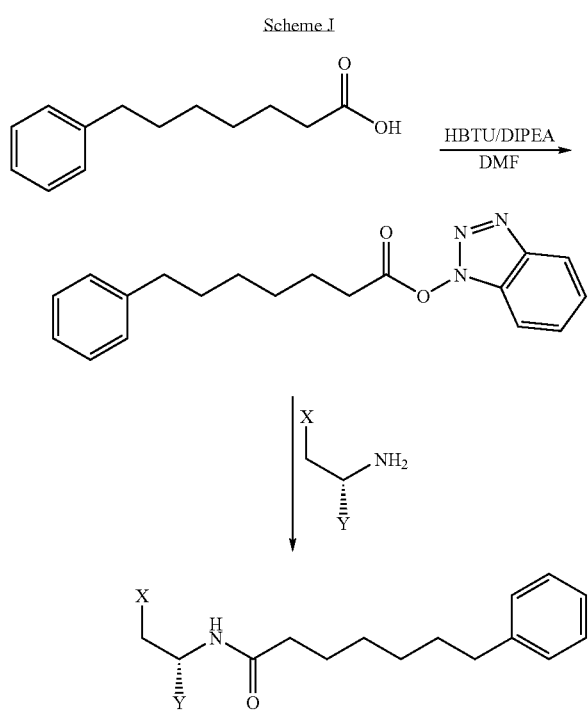

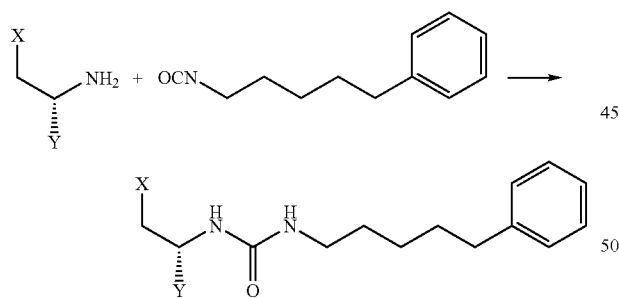

Where Q is of the formula (b), the coupling reaction is typically an amine+isocyanate reaction giving a urea product (Scheme K) [Larock, R. C. *Comprehensive Organic Transformations*; VCH Publisher: New York, 1989]. The illustrated example is the reaction with 5-phenylpentyl isocyanate.

Scheme K

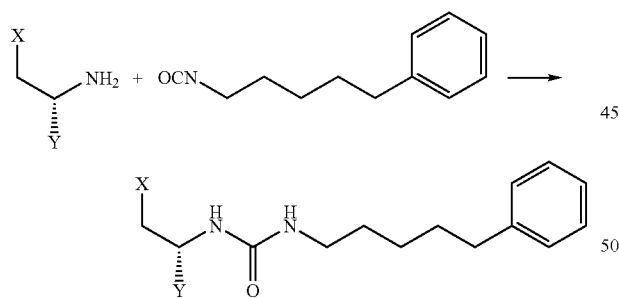

Where Q is of the formula (c), the reaction is typically an amine+carbonyl diimidazole+suitably substituted hydroxylamine ternary coupling giving an N-alkoxy urea product (Scheme L) [Romine, J. L. et al, *Synthesis*, 1994, 8, 846].

Scheme L

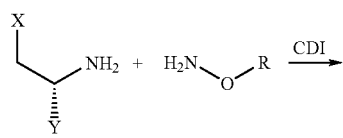

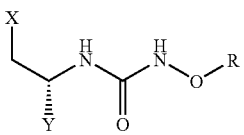

Where Q is of the formula (d), the coupling reaction is typically an amine+sulfonyl chloride reaction giving a sulfonamide product (Scheme M) [Larock, R. C. *Comprehensive Organic Transformations*; VCH Publisher: New York, 1989]. The illustrated example is the reaction with 6-phenylhexanesulfonic acid.

Scheme M

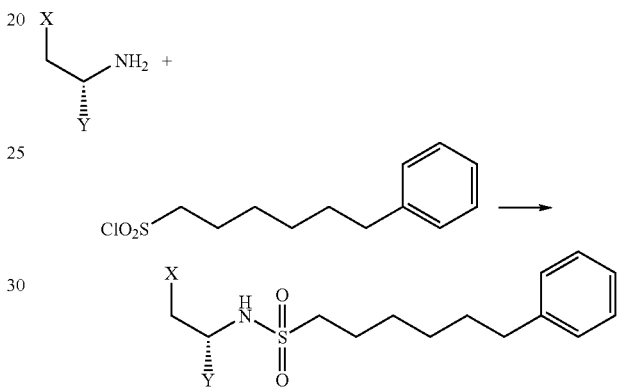

Where Q is of the formula (e), the coupling reaction is typically an amine+sulfinyl chloride reaction giving a sulfinamide product (Scheme N) [Moree, W. J., van der Marel, G. A., and Liskamp, R. J. *J. Org. Chem.* 1995, 60, 5157]. The illustrated example is the reaction with 6-phenylhexanesulfinic acid.

Scheme N

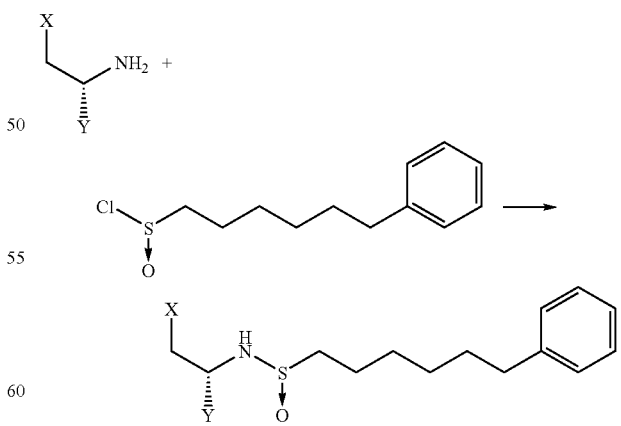

Where Q is of the formula (f), the coupling reaction is typically an amine+phosphonochloridate reaction giving a phosphonamide product (Scheme O) [Hirschmann, R. et al, *J. Am. Chem. Soc.,* 1995, 117, 6370].

Scheme O

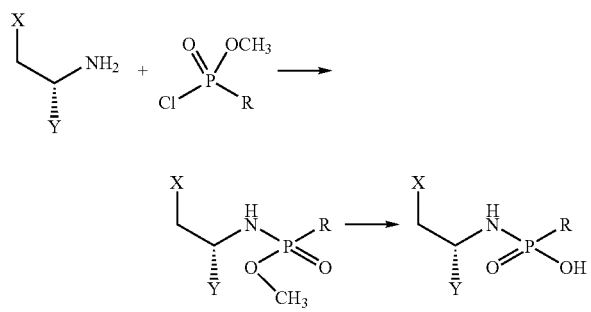

Where Q is of the formula (g), the coupling reaction is typically an amine+dialkylphosphoryl chloride (Scheme P) [Wang, M., Liu, S., Liu, J., and Hu, B,. *J. Org. Chem.*, 1995, 60, 7364]., or an amine+H-phosphonate [Tomoskozi, I., Gacs-Baitz, E., and Otvos, L, *Tetrahedron*, 1995, 51, 6797] reaction giving a phosphoramidate product.

Scheme P

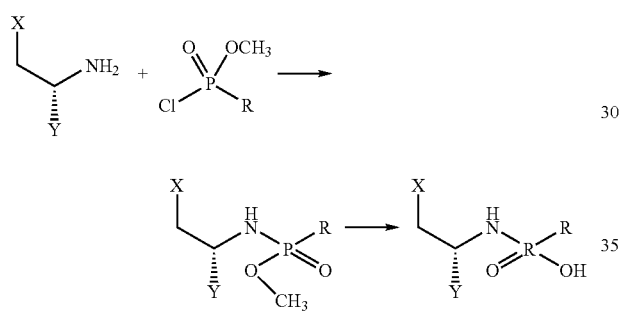

Incorporation of the Y group by derivatisation of an amino acid side chain can be achieved by known methods (Larock, R. C., *Comprehensive Organic Transformations*, VCH Publisher, 1989). For example alkylation an acylation of N, O or S atoms can be carried out using suitable alkylating and acylating agents, eg alkyl halides, cycloalkyl halides, aryl halides, acyl halides etc.

Some of the compounds of the invention can also be prepared as a mixture of enantiomeric forms from a suitable (DL)-α-amino acid by the processes outlined previously in Schemes A-P above. This forms a further aspect of the invention.

Many compounds of this invention can instead be prepared from non-anino acid precursors either enantiomerically pure or as a mixture of enantiomeric forms as indicated in Scheme Q. Aldol condensation of substituted benzaldehydes with ethyl levulinate yields an α,β-unsaturated ketone which may be hydrogenated and converted to an γ-amino acid derivative via the oxime. Coupling of the amine with an appropriate group Q as described in schemes J-P above.

Alternatively, where one enantiomer from the hydrogenation is required, the process can be conducted in a selective manner by employing one of several selective procedures described in the general literature (Hudlicky, M., *Reductions in Organic Chemistry*, 2$^{nd}$ Edition, ACS Monograph, Washington, 1996, pp 15-17). This forms a further aspect of the invention.

Scheme Q

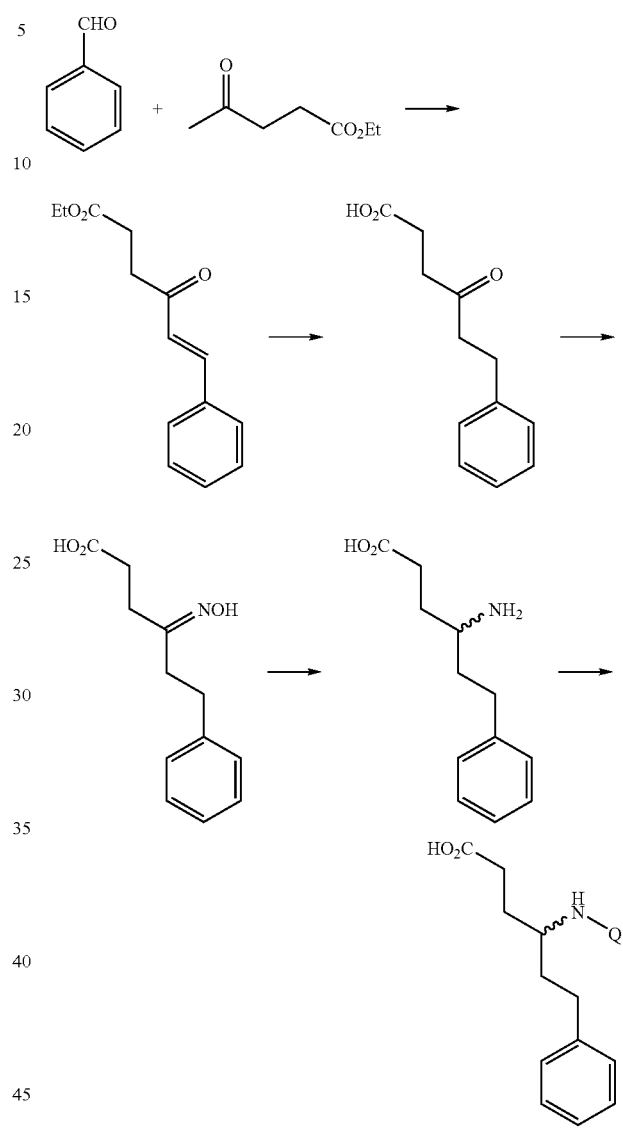

Certain compounds of the invention can also be prepared as single enantiomers from a suitable (L)-α-amino acid by the processes outlined in Scheme R. The α-acid group is converted to the aldehyde, which is elaborated via Wittig methodology to form the substitutent Y of the general formula (I). Elaboration of the α-amino group with groups Q as described in schemes J-P above forms a further aspect of the invention.

Scheme R

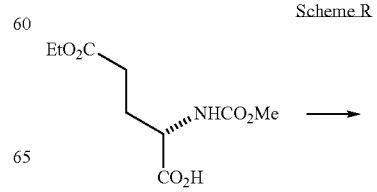

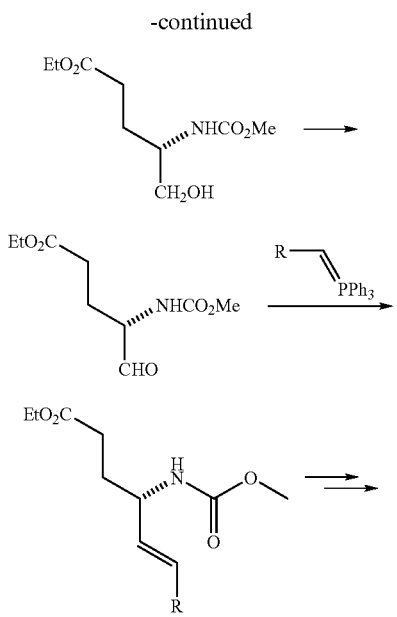

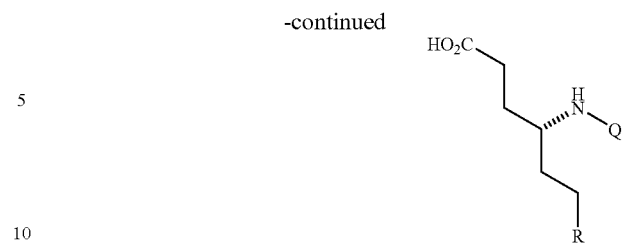

An illustrative example is the synthesis (Scheme 1) of an exemplary compound of formula (I) based on D-tryptophan. Commercially available Boc-D-tryptophan (1) can be converted to its benzyl ester. The ester can be N-alkylated in DMF with NaH and benzyl or cinnamyl bromide. Hydrolysis of the esters yields the acids (5) and (6) which are converted to the corresponding Weinreb amides using standard conditions. The amides are treated with LiAlH$_4$ in THF at low temperature yielding the aldehydes which were treated with Ph$_3$P=CHCO$_2$Me giving the unsaturated esters. Removal of the Boc group with TFA yielded the sn-1 synthons (13) and (14). Acylation with 7-phenylheptanoic acid yields the amides (15) and (16), which after hydrogenation under standard conditions followed by alkaline hydrolysis give the target compounds (19) and (20).

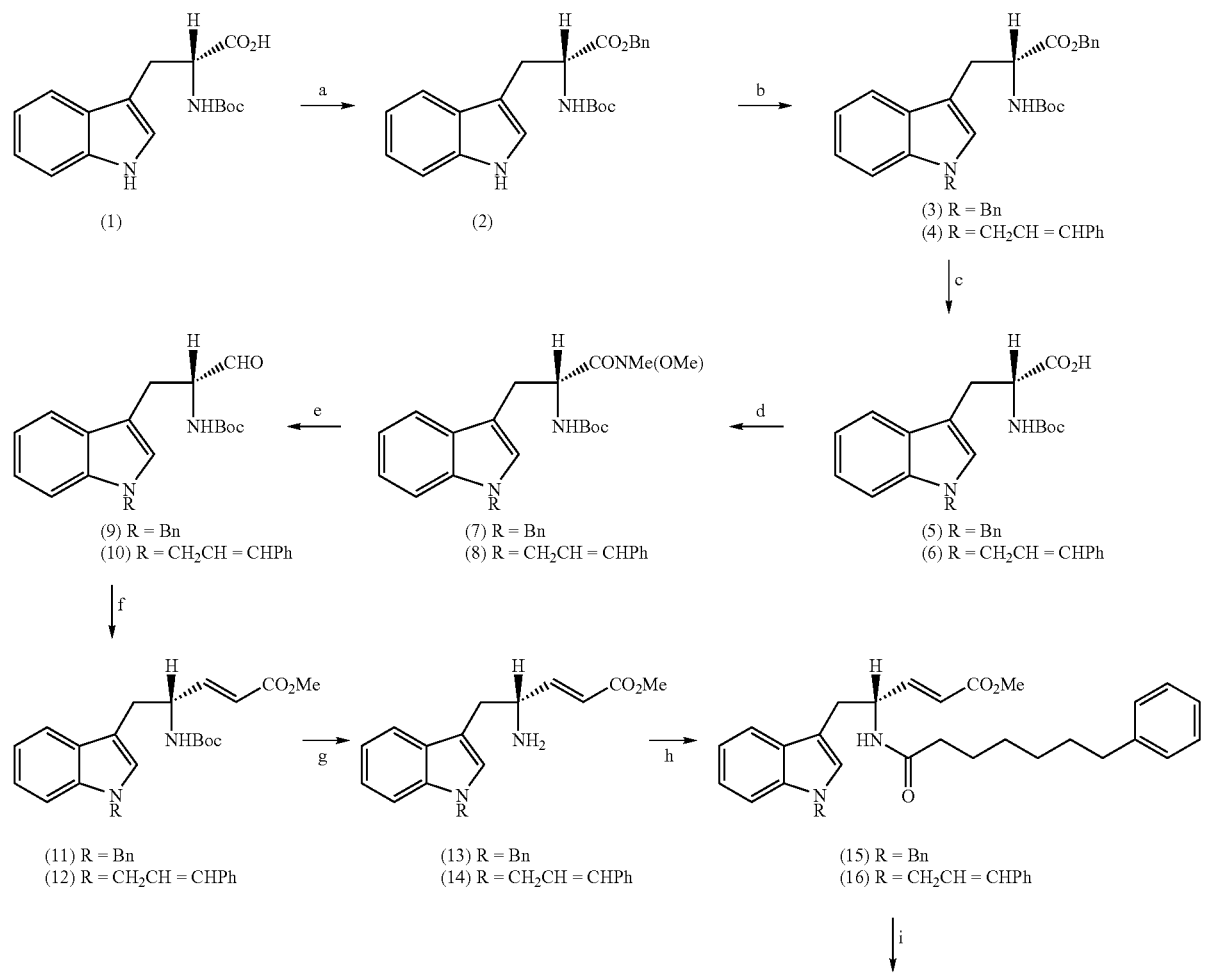

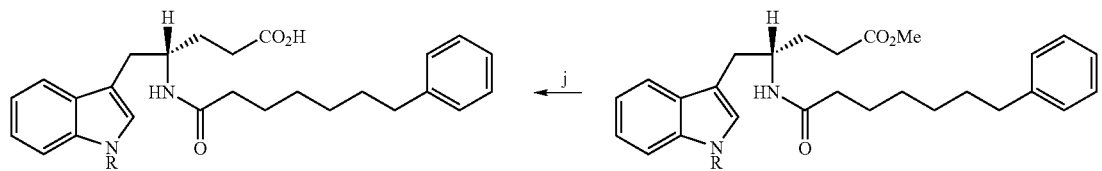

(19) R = Bn
(20) R = (CH$_2$)$_3$Ph

(17) R = Bn
(18) R = (CH$_2$)$_3$Ph (a) K$_2$CO$_3$, BnBr, DMF; (b) NaH, BnBr or BrCH$_2$CHCHPh, DMF; (c) NaOH, THF, MeOH, H$_2$O; (d) DIPEA, BOP, DMF, MeONHMe·HCl; (e) LiAlH$_4$, THF; (f) Ph$_3$P=CHCO$_2$Me, THF; (g) TFA, CH$_2$Cl$_2$; (h) DIPEA, BOP, DMF, Ph(CH$_2$)$_6$CO$_2$H; (i) 10% Pd/C, EtOAc; (j) NaOH, THF, MeOH, H$_2$O.

Scheme 2 is illustrative of a synthesis of a compound of formula (I) based on D-histidine. Thus, Boc-D-histidine (21) is converted to its benzyl ester (22) and treated with trityl chloride to afford the N$^\pi$-trityl protected ester. Hydrolysis of the ester (23) affords the acid (24) which can be elaborated as described in Example 1 to the unsaturated ester (27). The Boc and trityl groups may be removed with TFA in CH$_2$Cl$_2$ and the amine (28) coupled with 7-phenylheptanoic acid, BOP and DIPEA in DMF. The Histidine N-alkylation with cinnamyl bromide and sodium hydride yielded (30) which after hydrogenation and alkaline hydrolysis yielded the target compound (32).

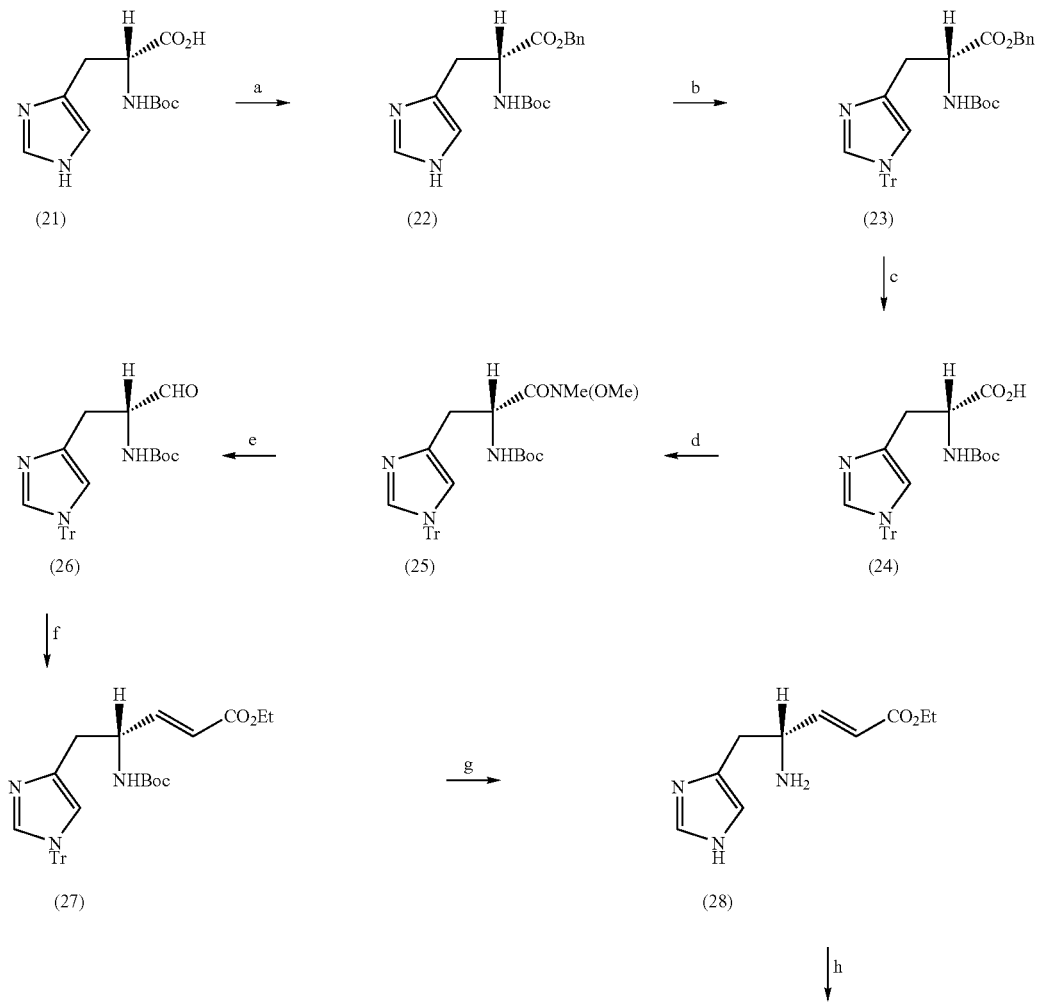

Scheme 2

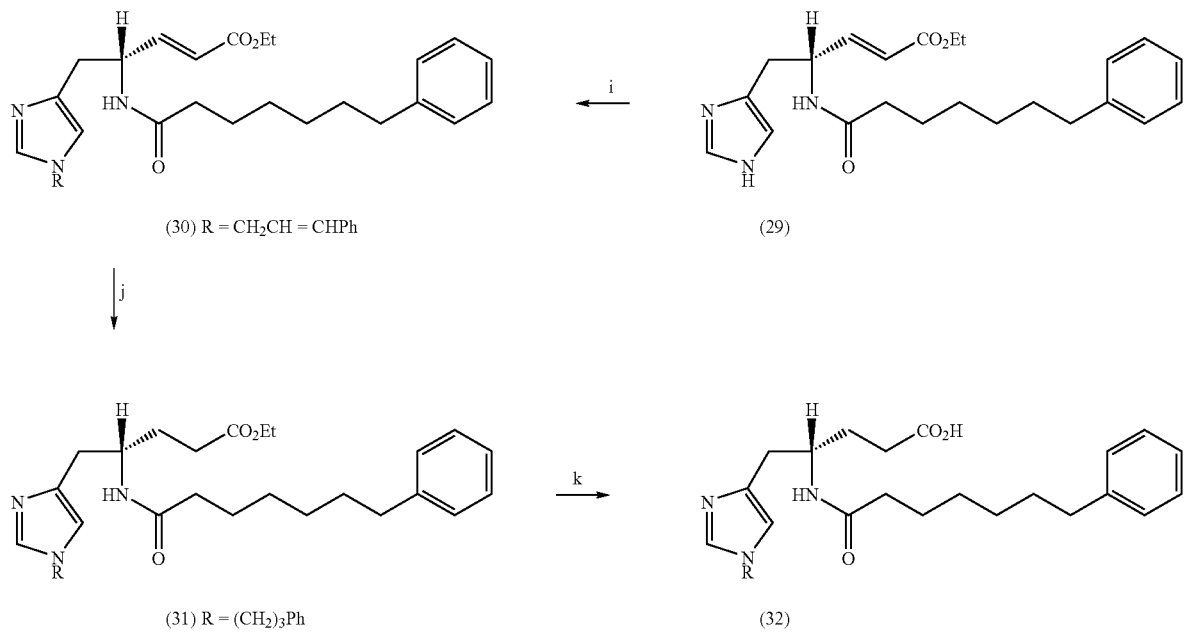

(30) R = CH$_2$CH = CHPh (29)

(31) R = (CH$_2$)$_3$Ph (32)

(a) K$_2$CO$_3$, BnBr, DMF; (b) TrCl, Et$_3$N, CHCl$_3$; (c) KOH, THF, MeOH, H$_2$O; (d) DIPEA, BOP, DMF, MeONHMe·HCl; (e) LiAlH$_4$, THF; (f) Ph$_3$P=CHCO$_2$Et, THF; (g) TFA, CH$_2$Cl$_2$; (h) DIPEA, BOP, DMF, Ph(CH$_2$)$_6$CO$_2$H; (i) NaH, DMF, cinnamyl bromide; (j) 10% Pd/C, EtOAc; (k) NaOH, THF, MeOH, H$_2$O.

Scheme 3 illustrates a method which can be generalised for the incorporation of a Z group derived from a L-amino acid onto an appropriate D-amino acid. Thus, treatment of Boc-L-Serine (33) with sodium hydride in DMF, followed by cinnamyl bromide yields the bis-alkylated compound (34) (Scheme 3). Alkaline hydrolysis followed by hydrogenation yields (36) in 56% overall yield from Boc-serine.

Scheme 3

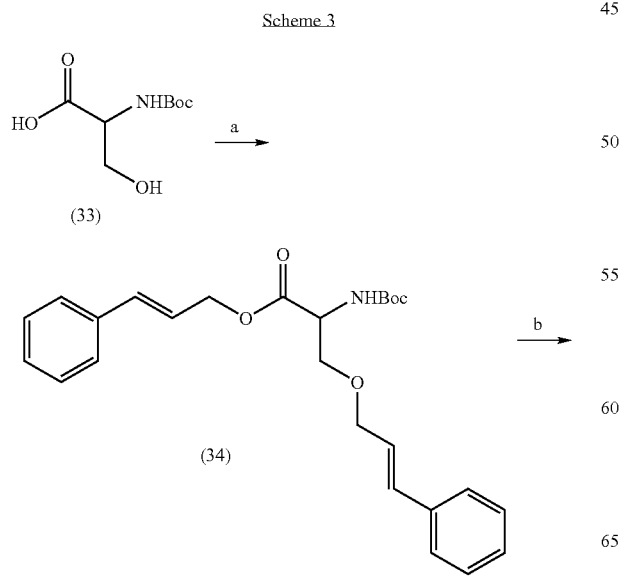

(33)

(34)

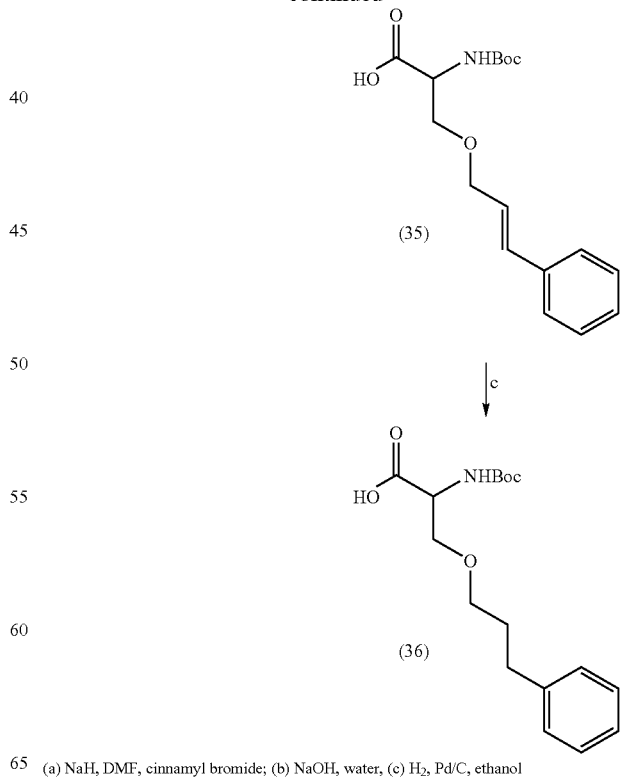

(35)

(36)

(a) NaH, DMF, cinnamyl bromide; (b) NaOH, water, (c) H$_2$, Pd/C, ethanol

Utilising the methodology outlined above, Boc-D-Tyrosine (37) bearing a sidechain benzyl group can be converted in three steps as illustrated in Scheme 4 to generate (40). Deprotection and acylation with the lipidic serine derived amino acid (36) yields (42), which can be converted to the target inhibitor (43) by hydrogenation, alakaline hydrolysis and finally, removal of the Boc protecting group (Scheme4).

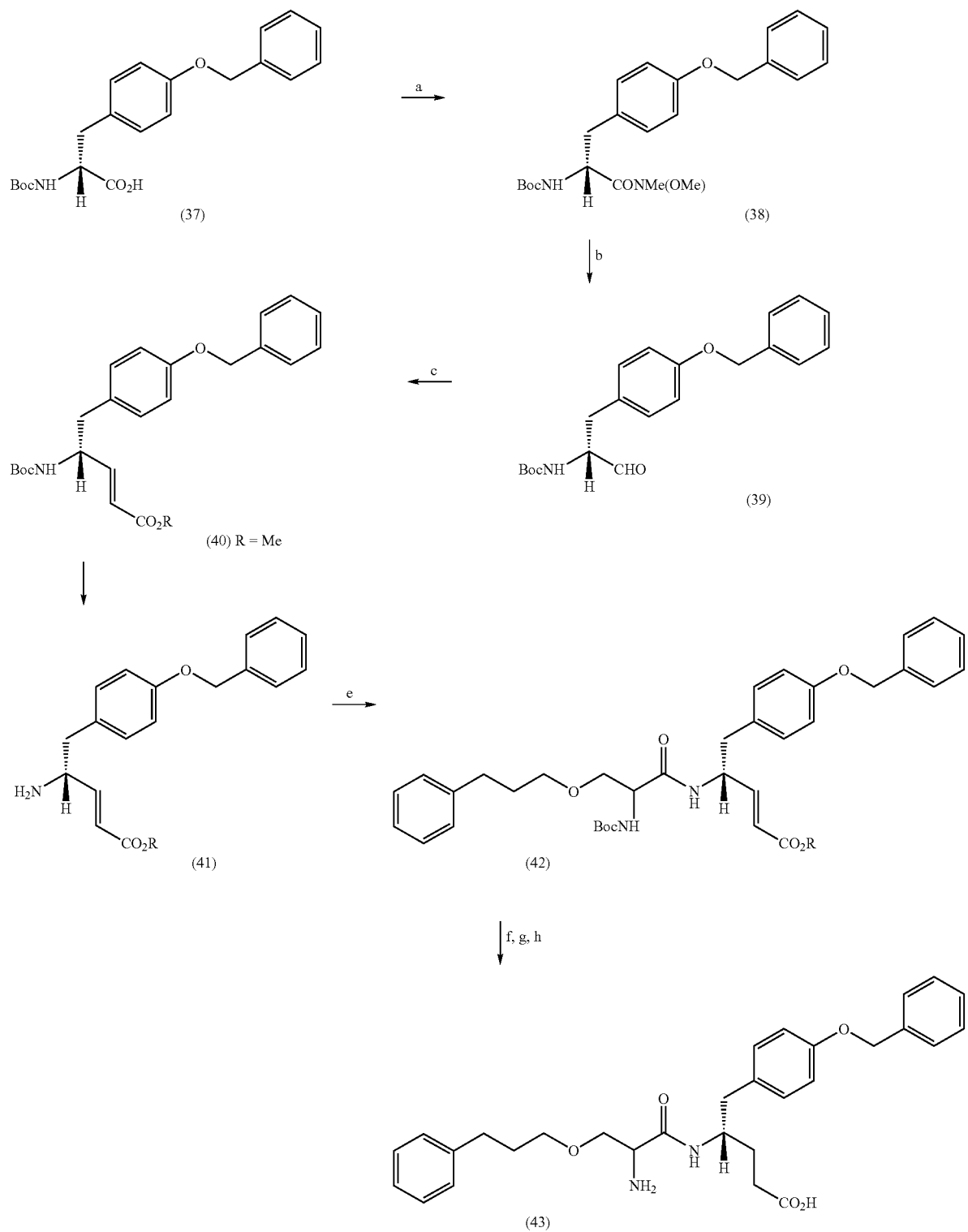

Scheme 4

(a) DIPEA, BOP, DMF, MeONHMe·HCl; (b) LiAlH$_4$, THF; (c) Ph$_3$P=CHCO$_2$Me; (d) TFA, CH$_2$Cl$_2$;
(e) DIPEA, BOP, DMF, (36); (f) 10% Pd/C, EtOAc; (g) NaOH, THF, MeOH, H$_2$O; (h) TFA, DCM

As shown in Scheme 5,3-(3-phenyl-propoxy)-propionic acid (45) can be assembled in a 3 step, one pot reaction from 3-phenyl-propanol (44). Coupling with the synthon (41) prepared in accordance with Example 3 yields the amide-ester (46). Hydrogenation, followed by ester hydrolysis yields (47).

Scheme 6 illustrates the synthesis of 7-phenylheptanoic acid as used in step (h) in Schemes 1 and 2. (5-Carboxy-hexyl)-triphenylphosphonium bromide (48) was converted to the ylid (49) using sodium hydride in THF, and Wittig reaction with benzaldehyde yielded the mixture of E- and Z-alkenes (50) as a 1:1 mixture. Hydrogenation yields the target synthon (51) in 85% yield.

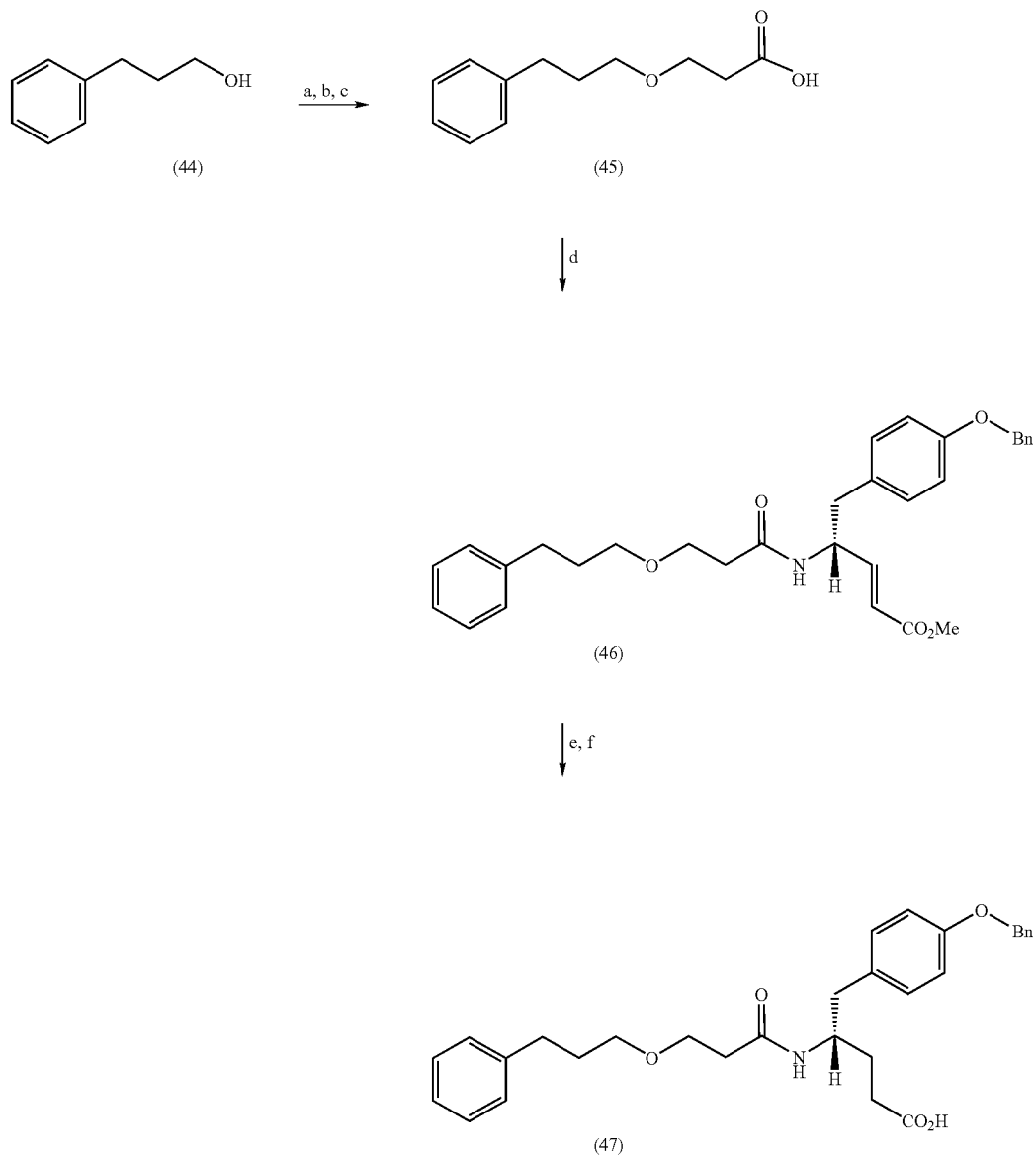

(a) NaH, THF;
(b) methyl acrylate, THF;
(c) H$_2$O, THF:
(d) DIPEA, BOP, DMF, (41);
(e) 10% Pd/C, EtOAc;
(f) NaOH, THF, MeOH, H$_2$O

Scheme 6

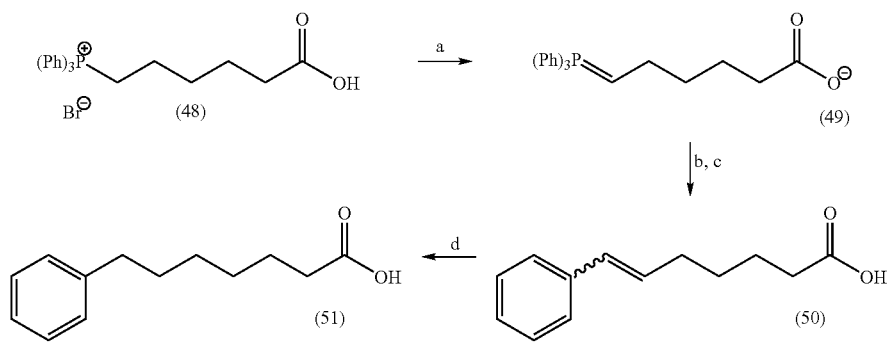

(a) NaH (2 equivalents), THF; (b) benzaldehyde THF; (c) H⁺/H₂O; (d) H₂, Pd/C

Scheme 7 illustrates the synthesis of a phosphonate compound of formula (I) (X=OPO₂HR').

[a]Reagents: (a) (1) NaH, DMF (2) PhO(CH₂)₃Br; (b) (1) LiOH, THF, H₂O (2) HCl (3) 2 eq. oxalyl chloride, cat. DMF, CH₂Cl₂; (c) LiAlH₄, THF, 0°; (d) (1) TFA, 0° (2) DIPEA, BOP, DMF, Ph(CH₂)₆CO₂H; (e) Et₃N, THF; (f) (1) tert-Butylamine, 50°, 5 days (2) Amberlyst 15 resin, MeOH.

Scheme 7.
Synthesis of phosphonate analogue[a]

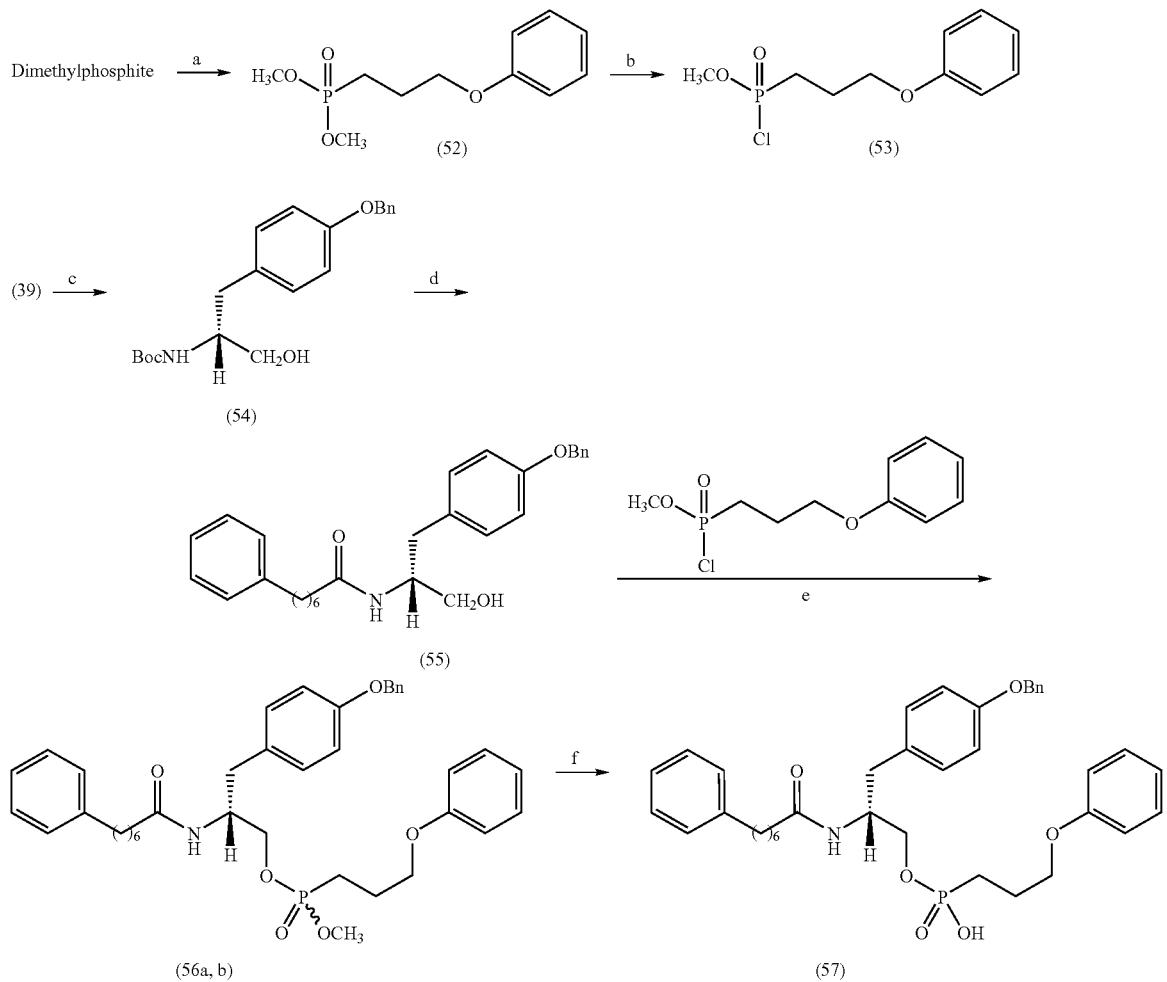

Scheme 8
Synthesis of a second phosphonate analogue[a]
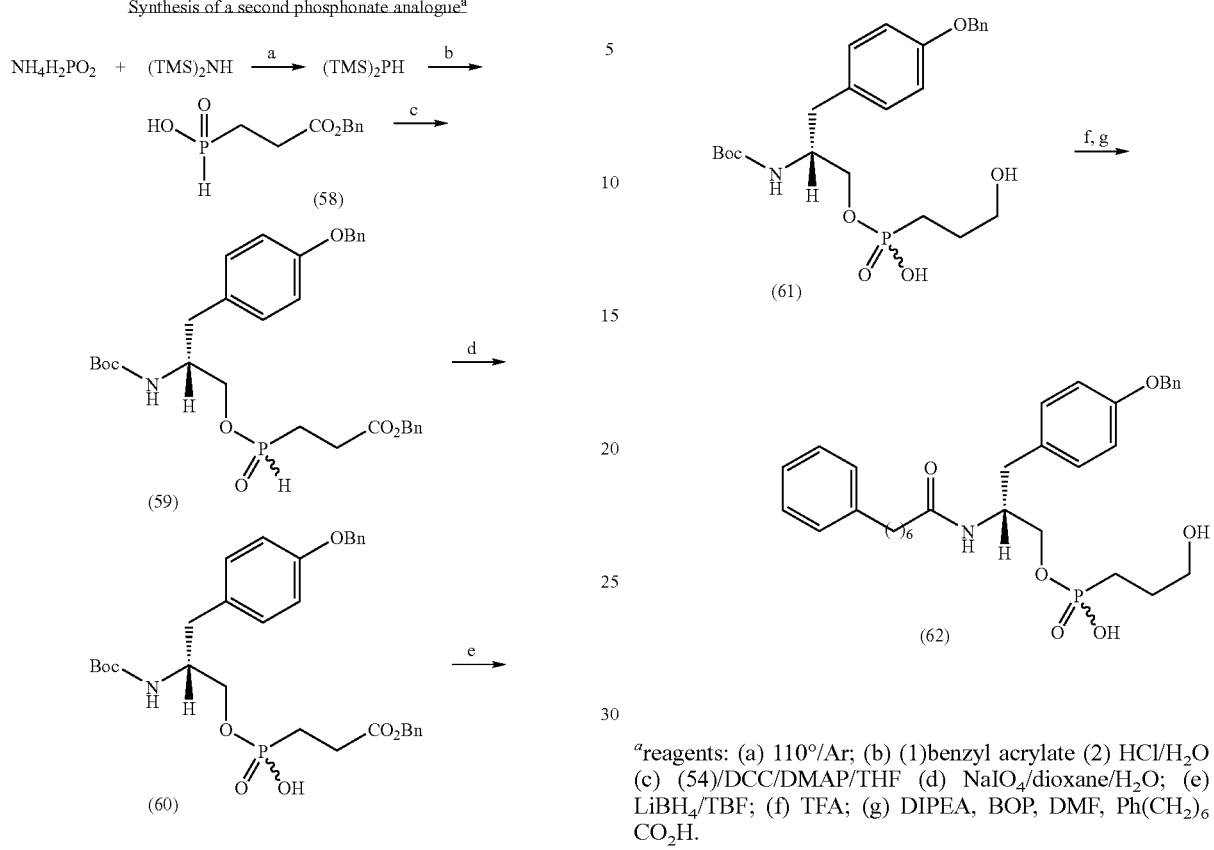
[a]reagents: (a) 110°/Ar; (b) (1)benzyl acrylate (2) HCl/H$_2$O (c) (54)/DCC/DMAP/THF (d) NaIO$_4$/dioxane/H$_2$O; (e) LiBH$_4$/TBF; (f) TFA; (g) DIPEA, BOP, DMF, Ph(CH$_2$)$_6$CO$_2$H.
Scheme 9 is illustrative of a synthesis of a compound bearing a tetrazole in place of the carboxylic acid moiety
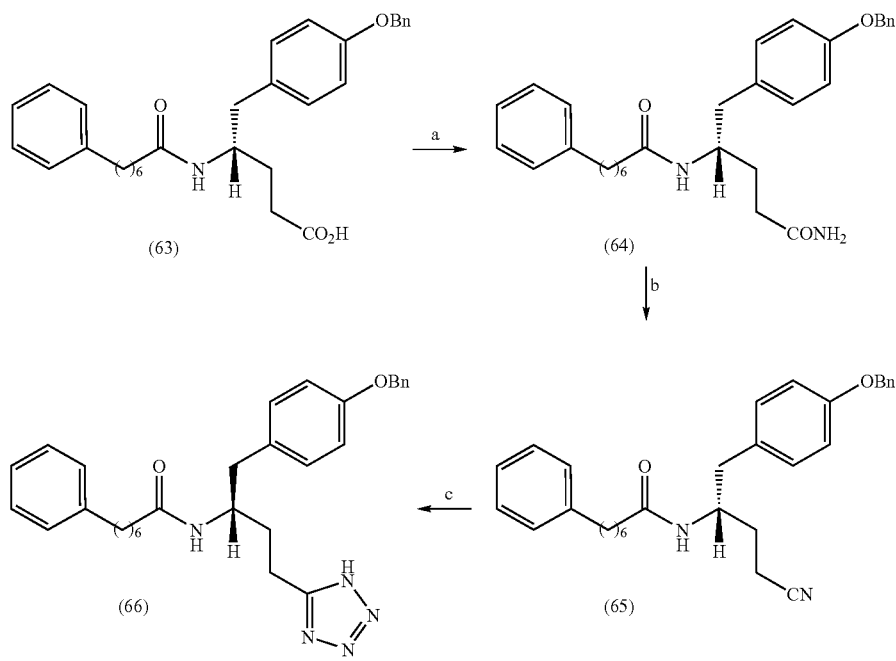

*Reagents: (a) DIPEA, BOP, DMF, NH$_4$OH; (b) POCl$_3$, pyridine, 0°; (c) 10 eq. NaN$_3$, 10 eq. Et$_2$NH.HCl, toluene, reflux Scheme 10 is illustrative of a synthesis of a second tyrosine-derived compound.

Scheme 10

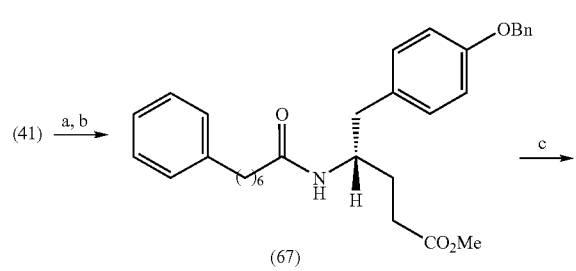

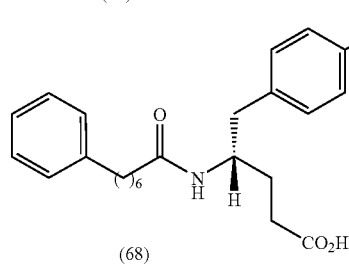

(a) DIPEA, BOP, DMF (51); (b) 10% Pd/C, EtOAc; (c) NaOH, THF, MeOH, H$_2$O

Schemes 11 and 12 are illustrative of the synthesis of other arylalkanoic acids

Scheme 11$^a$

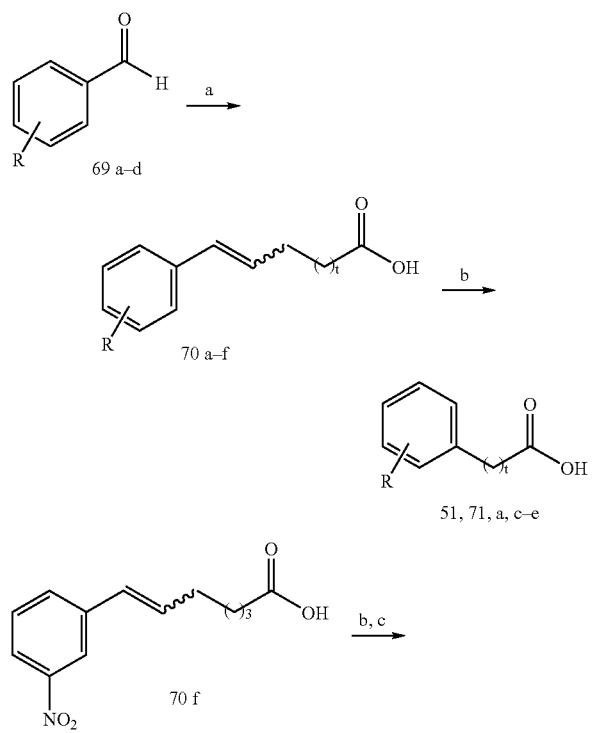

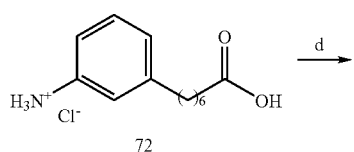

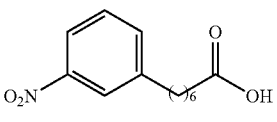

$^a$Reagents: (a) (1) NaH, THF, synthon 30 or 31 or 32; (b) 10% Pd-C, EtOAc (c) HCl, Et$_2$O; (d) oxone, aq. acetone, NaHCO$_3$

TABLE 1

Arylalkanoic acids and Precursors

| Compound | R | t |
|---|---|---|
| 69a | H | — |
| 69b | 2-MeO | — |
| 69c | 3-NHCOMe | — |
| 69d | 3-NO$_2$ | — |
| 70a | H | 2 |
| 70b | H | 3 |
| 70c | H | 4 |
| 70d | 2-MeO | 3 |
| 70e | 3-NHCOMe | 3 |
| 70f | 3-NO$_2$ | 3 |
| 71a | H | 5 |
| 51 | H | 6 |
| 71c | H | 7 |
| 71d | 2-MeO | 6 |
| 71e | 3-NHCOMe | 6 |

Scheme 12$^a$

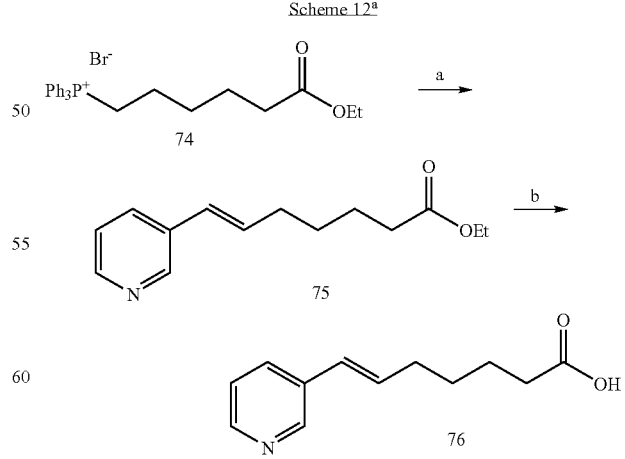

$^a$Reagents: (a) (1) NaH, THF (2) 3-pyridinecarboxaldehyde (b) (1) NaOH, THF, MeOH (2) HCl Scheme 13 illustrates a synthetic scheme starting from non-amino acid sources Scheme 13[a]
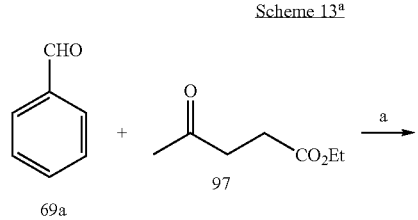
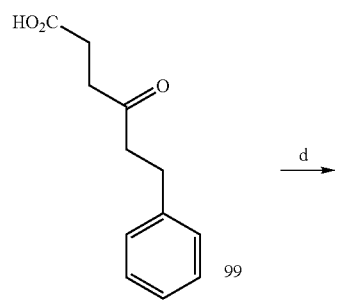
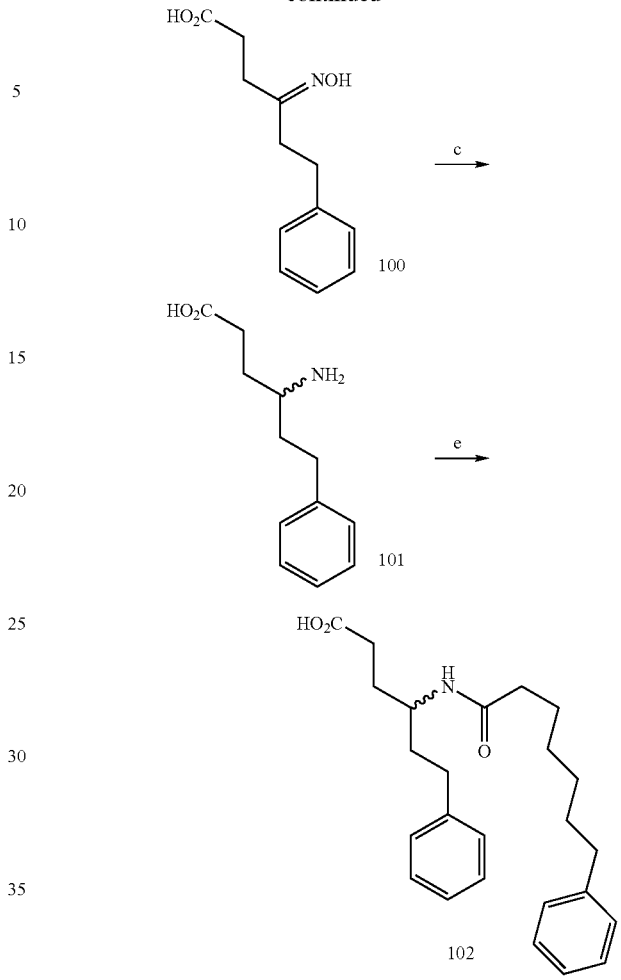
[a]Reagents: (a) piperidine/AcOH/benzene, Δ; (b) H$_2$, Pd-C; (c) NaOH; (d) HONH$_2$; (e) BOP, DIPEA, DMF, 7-phenylheptanoic acid (27b)
Scheme 14[a]
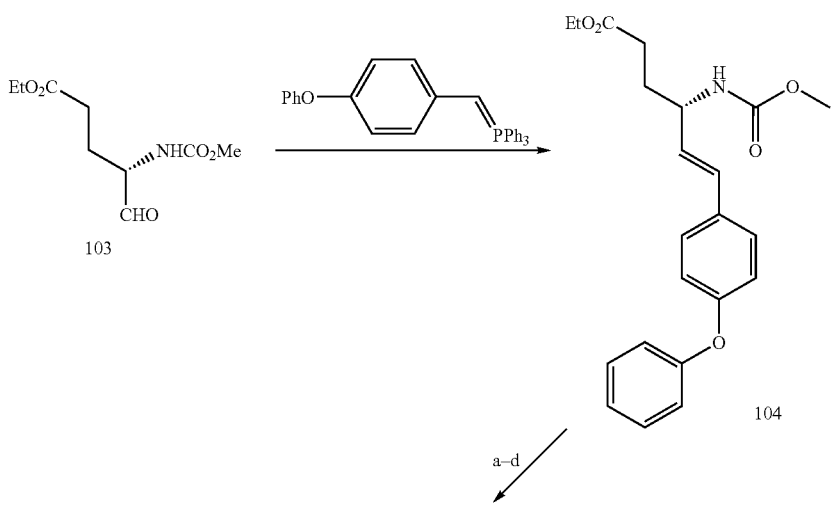

-continued

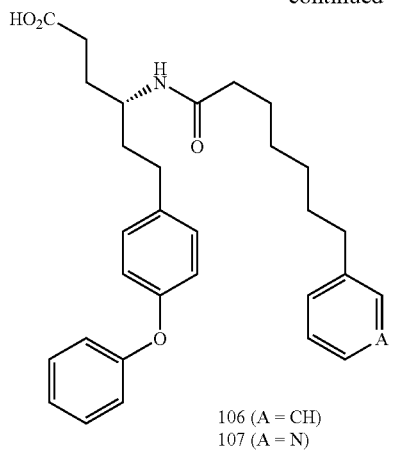

106 (A = CH)
107 (A = N)

<sup>a</sup>Reagents: (a) NaOH; (b) H₂, Pd-C (c) Me₃SiI; (d) BOP/DIPEA/DMF, 7-phenylheptanoic acid or 7-pyridylheptanoic acid The compounds of the invention may be useful in the therapeutic treatment of inflammatory diseases and conditions. Examples of inflammatory diseases or conditions which may be treated by the compounds of the present invention include but are not restricted to rheumatoid arthritis, multiple sclerosis, osteoarthritis, psoriasis, surgical adhesions, Crohn's disease, dermatitis, ulcers, lupus, immune complex disease, cystic fibrosis, atherosclerosis, fibrosis, bowel disease, hypotension, asthma, allergy, reperfusion injury, myocardial infarct, ischemic disease, Alzheimer's disease, dysmenorrhoea, diabetes (type I), pancreatitis, pulmonary condititons, malaria, dermatitis, adult respiratory distress syndrome (ARDS), sepsis, uveitis, lung injuries, vascular diseases, synovitis, peritonitis, cancer, allergies, chronic lung diseases, myocardial infarct, meningitis, retinitis, transplantation, graft rejection.

The compounds of the invention may be used to treat humans or other manmaliaan subjects. The compounds of the invention are considered to be particularly suitable for the treatment of hunian subjects. Non-human subjects may include primates, livestock animals (eg. sheep, cows, horses, goats, pigs) domestic companion animals (eg cats, dogs) laboratory test animals (eg mice, rats, guinea pigs, rabbits) or captive wild animals.

The compounds of the invention are administered to the subject in a prophylactic or treatment effective amount. As used herein, a treatment effective amount is intended to include at least partially attaining the desired effect, or delaying the onset of, or inhibiting the progression of, or halting or reversing altogether the onset or progression of the particular disease or condition being treated. A prophylactic effective amount includes an amount effective to prevent or delay the onset or reduce the severity of a disease or condition.

As used herein, the term "prophylactic effective amount" or "treatment effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages may lie within the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage Suitably, the dosage is in the range of 1 μg to 500 μg per kg of body weight per dosage, such as 1 μg to 200 mg per kg of body weight per dosage, or 1 μg to 100 mg per kg of body weight per dosage. Other suitable dosages may be in the range of 1 mg to 250 mg per kg of body weight, including 1mg to 10, 20, 50 or 100 mg per kg of body weight per dosage or 10 μg to 100 mg per kg of body weight per dosage.

The invention also contemplates a method of inhibiting the activity of phospholipase in an animal or mammal, said method comprising administering to said animal or mammal a modulatory or inhibiting effective amount of a compound of Formula (I), or a salt, derivative or prodrug thereof.

Suitable dosage amounts and dosing regimens can be determined by the attending physician and may depend on the particular condition being treated, the severity of the condition, as well as the general health, age and weight of the subject.

The active ingredient may be administered in a single dose or a series of doses. While it is possible for the active ingredient to be administered alone, it is preferable to present it to a subject as a composition, preferably as a pharmaceutical composition. The formulation of such compositions are well know to those skilled in the field. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include supplementary anti-inflammatory or other physiologically active agents where appropriate.

The carrier, diluent or excipient must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a fiee-flowing form such as a powder or granules, optionally mixed with a binder (e.g inert diluenit, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for topical administration, for example, dermally, may be in the form of lotions, creams, pastes, gels, ointments and the like Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, anipoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compounds of the invention may also be presented for use in veterinary compositions. These may be prepared by any suitable means known in the art. Examples of such compositions include those adapted for:
(a) oral administration, external application (eg drenches including aqueous and non-aqueous solutions or suspensions), tablets, boluses, powders, granules, pellets for admixture with feedstuffs, pastes for application to the tongue;
(b) parenteral administration, eg subcutaneous, intramuscular or intravenous injection as a sterile solution or suspension
(c) topical application eg creams, ointments, gels, lotions etc.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The reference to any prior art in this specification is not, and should not be taken as, an acknowledgment or any form of suggestion that that prior art forms part of the common general knowledge in Australia.

The invention will now be described with reference to the following examples which are included for the purpose of illustrating certain embodiments of the invention and are not to be taken as limiting the generality as hereinbefore described.

EXAMPLES

General Methods

All materials were obtained commercially as reagent grade unless otherwise stated. Melting points were determined on a Reichert Hot stage apparatus and are uncorrected. $^1$H and $^{13}$C n.m.r spectra were measured on Bruker ARX-500 or Varian Gemini 300 n.m.r. spectrometers at 298° K. and chemical shifts are reported in ppm relative to tetramethylsilane or solvent as indicated (CD$_3$OH $\delta_H$ 3.31, $\delta_C$ 49.0; DMSO-d$_6$ $\delta_H$ 2.50, $\delta_C$ 39.7; CD$_3$CN $\delta_H$ 1.94, $\delta_C$ 1.39; CDCl$_3$ δ$_H$ 7.27, δ$_C$ 77.0 ppm). Preparative scale reverse phase HPLC separations were performed on Waters Delta-Pak PrepPak C18 40 mm×100 mm cartridges (100 Å) or on a Waters 600 system equipped with a Rheodyne preparative injector with 5 mL loop volume on a Vydac C18 90 Å 10 µM column 250×22 mm at 20 mL/min using gradient elution; analytical reverse phase HPLC was performed on Waters Delta-Pak Radial-Pak C18 8 mm×100 mm cartridges (100 Å) using gradient mixtures of water/0.1% TFA and water 10%/acetonitrile 90%/TFA 0.1%.) and UV detection at 280 nm. Routine Mass spectra were measured on a PE-SCIEX API-3 or Perceptive Biosystems Mariner API-TOF instrument equipped with an LC pump and Rheodyne injector. Reaction mixtures were sampled and diluted with 70% MeCN/30% H$_2$O and were introduced into the mass spectrometer at 30-50 µL/min. As a result of the atmospheric pressure ionisation process (electrospray), only molecular ions MH$^+$ were observed for each component in the sample. High Resolution Mass Spectra of purified products were measured on a Finnigan 2000 with resolving power in excess of 20,000.

Abbreviations

The following abbreviations are used in the specification

| BnBr | benzyl bromide |
|---|---|
| Boc | t-butoxycarbonyl |
| benzotriazolyloxytris-(dimethylamino)phosphonium hexafluorophosphate | |
| DIPEA | diisopropylethylamine |
| DMF | dimethylformamide |
| DMSO | dimethylsulfoxide |
| Et$_2$O | diethyl ether |
| EtOAc | ethyl acetate |
| TFA | trifluoroacetic acid |
| THF | tetrahydrofuran |
| HOBT | 1-Hydroxybenzotriazole |
| Benzotriazol-l-yl-oxytripyrrolidinophosphonium hexafluorophosphate | |
| O-(Benzotriazol-l-yl)-N,N,N',N'-tetramethyluronium hexafluorophosphate | |
| O-(Benzotriazol-l-yl)-N,N,N',N'-tetraethyluronium tetrafluoroborate | |

Example 1 (See Scheme 1)

(R)-2-tert-Butoxycarbonylamino-3-(1H-indol-3-yl)-propionic acid benzyl ester(2)

A solution of Boc-D-tryptophan (25 g, 82.24 mmol), BnBr (14.76 g, 10.25 ml, 86.35 mmol) and K$_2$CO$_3$ (28.37 g, 0.206 mol) in DMF (350 mL) was stirred overnight at room temperature. The solvent was removed and the residue taken up into water and CH$_2$Cl$_2$. The organic layer was washed successively with water and brine and then dried over MgSO$_4$. The solution was filtered and the solvent removed to afford crude product. Recrystallisation from EtOAc gave the title compound as a white solid (24.05 g, 74%). mp 141.4-142° C. $^1$H NMR (CDCl$_3$) δ 7.98 (1H, br s), 7.55 (1H, d, J=7.68 Hz), 7.08-7.35 (9H, m), 6.81 (1H, br s), 5.09 (2H, d), 3.29 (2H, d, J=5.37 Hz), 1.42 (9H, s). $^{13}$C NMR (CDCl$_3$) δ 172.4,155.5, 136.3, 135.4, 128.6, 128.5, 127.7, 123.1, 122.1, 119.6, 118.8, 111.4, 109.8, 80.1, 67.2, 54.5, 28.4, 28.1. ISMS: 395 (M+H), (R)-3-(1-Benzyl-1H-indol-3-yl)-2-tert-butoxycarbonylamino-propionic acid benzyl ester (3)

2-tert-Butoxycarbonylamino-3-(1H-indol-3-yl)-propionic acid benzyl ester (2 g, 5 mmol) in DMF (10 mL) was added over 10 min to a slurry of NaH (240 mg 60% dispersion in mineral oil, 6 mmol) in DMF (10 mL) at 0° C. The resultant solution was stirred at this temperature for 30 min. BnBr (1.128 g, 0.785 mL, 6.5 mmol) in DMF (5 mL) was then added slowly to the solution at 0° C. and then mixture warmed to room temperature over 1.5 h. After stirring overnight the reaction was quenched and the solvent removed. The residue was taken up into EtOAc and washed with water, brine and dried with MgSO$_4$. Filtration and removal of the solvent yielded crude material which was subject to column chromatography (silica gel, 50% EtOAc/petroleum ether, Rf 0.85) to give the ester (2.276 g, 92%). $^{13}$C NMR (CDCl$_3$) δ 172.0, 155.2, 137.4, 136.5, 135.4, 128.7, 128.5, 128.3, 127.5, 127.4,126.9, 126.9, 126.6, 121.9, 119.4, 119.1, 109.7, 109.2, 79.7, 66.9, 54.5, 49.8, 28.3, 27.9. ISMS: 485 (M+H), (R)-2-tert-Butoxyearbonylamino-3-[1-(3-phenyl-allyl)-1H-indol-3-yl]-propionic acid benzyl ester (4)

2-tert-Butoxycarbonylamino-3-(1H-indol-3-yl)-propionic acid benzyl ester (5 g, 12.69 mmol) in DMF (25 mL) was added over 10 min to a slurry of NaH (560 mg 60% dispersion in mineral oil, 13.96 mmol) in DMF (25 mL) at 0° C. The resultant solution was stirred at this temperature for 30 min. Cinnamyl bromide (2.5 g, 1.877 mL, 12.69 mmol) in DMF (12.5 mL) was then added slowly to the solution at 0° C. and then mixture warmed to room temperature over 1.5 h. After stirring overnight the reaction was quenched and the solvent removed. The residue was taken up into EtOAc and washed with water, brine and dried with MgSO$_4$. Filtration and removal of the solvent yielded crude material which was subject to column chromatography (silica gel, 50% EtOAc/petroleum ether, Rf 0.81) to give the ester (6.47 g, quantitative). $^1$H NMR (CDCl$_3$) δ 7.55 (1H, d, J=7.68 Hz), 7.41-7.07 (13H, m), 6.69 (1H, s), 6.37 (1H, d, J=15.81 Hz), 6.23 (1H, dt, J=5.4, 15.87 Hz), 5.10 (3H, m), 5.02 (1H, d, J=12.51 Hz), 4.8 (1H, m), 4.72 (2H, d, J=5.4 Hz), 3.29 (2H, d, J=5.1 Hz), 1.4 (9H, s). $^{13}$C NMR (CDCl$_3$) δ 171.9, 155.0, 136.1, 135.9, 135.2, 131.9, 128.6, 128.3, 128.2, 128.1, 127.3, 127.6, 126.7, 126.3, 124.6, 121.6, 119.1, 118.9, 109.4, 108.8, 79.6, 66.8, 54.3, 47.9, 28.1, 27.7.

(R)-3-(1-Benzyl-1H-indol-3-yl)-2-tert-butoxycarbonylamino-propionic acid (5)

To 3-(1-benzyl-1H-indol-3-yl)-2-tert-butoxycarbonylamino-propionic acid benzyl ester (2.1 g. 4.3 mmol) in MeOH (10 mL) was added KOH (0.740 g, 12.9 mmol) in water (5 mL). THF (5 mL) was added until the solution became homogenous. The solution was stirred until completion (about 2 h). Volatile solvents were removed and the residue taken up into CH$_2$Cl$_2$ and water. The aqueous layer was carefully acidified with dilute aqueous HCl and extracted with Et$_2$O. The Et$_2$O was washed with water and brine and then dried with MgSO$_4$. The solution was filtered and the solvent removed to afford the required material without further purification (1.555 g, 91%). ESMS 395 (M+H$^+$), mp 163.8-165.4° C. (EtOAc/petroleum ether). $^1$H NMR (DMSO-d$_6$) δ 7.56 (1H, d, J=7.83 Hz), 7.39-6.99 (10H, m), 6.65 (1H, d), 4.18 (1H, m), 5.36 (2H, s), 3.15 (1H, dd, J=4.67, 14.56 Hz), 2.99 (1H, dd, J=9.18, 14.56 Hz), 1.32 (9H, s). $^{13}$C NMR (DMSO-d$_6$) δ 174.0, 155.2, 137.6, 136.4, 128.7, 127.5, 127.2, 126.7, 126.6, 121.7, 119.3, 119.2, 109.7, 109.6, 79.4, 54.1, 49.9, 28.3, 27.7. ISMS: 395 (M+H),

(R)-2-tert-Butoxycarbonylamino-3-[1-(3-phenyl-allyl)-1H-indol-3-yl]-propionic acid (6)

To 2-tert-butoxycarbonylamino-3-[1-(3-phenyl-allyl)-1H-indol-3-yl]-propionic acid benzyl ester (6.483 g. 12.71 mmol) in MeOH (25 mL) was added KOH (2.4 g, 42.86 mmol) in water (10 mL). THF (30 mL) was added until the solution became homogenous. The solution was stirred until completion (overnight). Volatile solvents were removed and the residue taken up into $CH_2Cl_2$ and water. The aqueous layer was carefully acidified with dilute aqueous HCl and extracted with-$Et_2O$. The $Et_2O$ was washed with water and brine and then dried with $MgSO_4$. The solution was filtered and the solvent removed to afford the required material without further purification (5.27 g, quantitative). ESMS 421 (M+H$^+$) $^1$H NMR (DMSO-$d_6$) δ 7.56-6.88 (11H, m), 6.47 (1H, d, 15.85 Hz), 6.40 (1H, dt, J=5.4, 15.85 Hz), 4.91 (2H, d, J=5Hz), 4.14 (1H, m), 3.15 (1H, m), 2.99 (1H, m), 1.29 (9H, s). $^{13}$C NMR (DMSO-$d_6$) δ 173.8, 155.3, 136.1, 135.9, 131.4, 128.6, 127.9, 127.7, 126.8, 126.3, 125.8, 121.1, 118.6, 110.3, 109.9, 77.9, 54.6, 47.4, 28.1, 26. 8. ISMS: 421 (M+H),

(R)-[2-(1-Benzyl-H-indol-3-yl)-1-(methoxy-methyl-carbamoyl)-ethyl]-carbamic acid teit-butyl ester (7)

A solution of 3-(1-benzyl-1H-indol-3-yl)-2-tert-butoxycarbonylamino-propionic acid (3.059 g, 7.763 mmol), BOP (3.60 g, 8.152 mmol) and DIPEA (3 g, 4.05 mL, 23.29 mmol) in DMF (50 mL) was stirred at room temperature for 5 min. N,O-Dimethylhydroxylamine hydrochloride (0.8 g, 8.15 inmol) was added and the solution stirred for 2 h. The solvent was removed and the residue taken up into $CH_2Cl_2$. The $CH_2Cl_2$ was washed with dilute aqueous HCl, water and brine. The solution was dried with $MgSO_4$, filtered and the solvent removed. The crude material was recrystallised from EtOAc (3.223 g, 95%). $^1$H NMR (CDCl$_3$) δ 7.61 (1H, d, J=7.26 Hz), 7.30-7.08 (8H, m), 5.27 (3H, m), 6.98 (1H, s), 3.60 (3H, s), 5.0 (1H, m), 3.23 (1H, dd, J=5.85, 14.58 Hz), 3.10 (5H, br s), 1.39 (9H, s), $^{13}$C NMR (CDCl$_3$) δ 172.6, 155.3, 137.6, 136.5, 128.7, 128.4, 127.5, 126.8, 126.7, 121.8, 119.2, 118.9, 110.0, 109.6, 79.4, 61.4, 51.0, 49.9, 28.3, 28.2. ISMS: 438 (M+H),

(R)-{1-(Methoxy-methyl-carbamoyl)-2-[1-(3-phenyl-allyl)-1H-indol-3-yl]-ethyl}-carbamic acid tert-butyl ester(8)

A solution of 2-tert-Butoxycarbonylamino-3-[1-(3-phenyl-allyl)-1H-indol-3-yl]-propionic acid (2 g, 4.76 mmol), BOP (2.21 g, 5 mmol) and DIPEA (1.855 g, 2.5 mL, 14.38 mmol) in DMF (50 mL) was stirred at room temperature for 5 min. N,O-Dimethylhydroxylamine hydrochloride (488 mg, 5 mmol) was added and the solution stirred for 2 h. The solvent was removed and the residue taken up into $CH_2Cl_2$. The $CH_2Cl_2$ was washed with dilute aqueous HCl, water and brine. The solution was dried with $MgSO_4$, filtered and the solvent removed. The crude material was recrystalised from EtOAc (1.34 g, 61%), mp 131-132.7° C. $^1$H NMR (CDCl$_3$) δ 7.60 (1H, d, J=7.56 Hz), 7.26-7.07 (8H, m), 6.98 (1H, s), 6.38 (1H, d, J=15.93 Hz), 6.25 (1H, dt, J=5.1, 15.81 Hz), 5.38 (1H, d, J=8.1 Hz), 4.99 (1H, m), 4.75 (2H, d, J=5.1 Hz), 3.61 (3H, s), 3.23 (1H, dd, J=5.4, 14.4 Hz), 3.09 (4H, br s), 1.36 (9H, s), $^{13}$C NMR (CDCl$_3$) δ 172.5, 155.2, 136.0, 131.8, 128.3, 127.6, 126.2, 126.2, 121.5, 118.9, 118.7, 117.6, 109.7, 109.6, 109.4, 79.2, 61.2, 50.9, 47.9, 31.9, 28.1. ISMS: 464 (M+H),

[2-(1-Benzyl-1H-indol-3-yl)-1-formyl-ethyl]-carbamic acid tert-butyl ester (9)

A suspension of LiAlH$_4$ (143 mg, 3.76 mmol) in THF (5 mL) was added over 10 min to a solution of [2-(1-benzyl-2-methyl-2,3-dihydro-1H-indol-3-yl)-1-(methoxy-methyl-carbamoyl)-ethyl]-carbamic acid tert-butyl ester (2 g, 4.32 mmol) in THF (35 mL) at −20° C. The reduction was complete in 15 min (silica gel, 50% EtOAc/petroleum ether, Rf 0.76). Saturated sodium potassium tartrate (10 mL) was added, and the solvent removed. Water was added and the residue extracted with $Et_2O$. The $Et_2O$ was washed with brine, dried and filtered. Removal of the solvent gave the title compound (1.204 g, 93%). $^1$H NMR (CDCl$_3$) δ $^{13}$C NMR (CDCl$_3$) δ 200.3, 155.5, 137.3, 136.6, 128.7, 128.1, 127.6, 127.0, 126.7, 122.1, 119.5, 119.0, 109.8, 109.1, 79.9, 60.2, 49.9, 28.3, 25.2,

(R){1-Flormyl-2-[1-(3-phenyl-allyl)-1H-indol-3-yl]-ethyl}-carbamic acid tert-butyl ester(10)

A suspension of LiAlH$_4$ (181 mg, 4.75 mmol) in THF (10 mL) was added over 10 min to a solution of {1-(methoxy-methyl-carbamoyl)-2-[1-(3-phenyl-allyl)-1H-indol-3-yl]-ethyl}-carbamic acid tert-butyl ester (2 g, 4.32 mmol) in THF (45 mL) at −20 ° C. The reduction was complete in 15 min (silica gel, 50% EtOAc/petroleum ether, Rf 0.75). Saturated sodium potassium tartrate (10 mL) was added, and the solvent removed. Water was added and the residue extracted with $Et_2O$. The $Et_2O$ was washed with brine, dried and filtered. Removal of the solvent gave the title compound. $^{13}$C NMR (CDCl$_3$) δ 200.1, 155.3, 132.2, 128.3, 127.7, 126.2, 124.4, 121.8, 119.2, 118.8, 109.5, 108.7, 79.7, 60.0, 47.9, 28.0, 24.9.

(R)-5-(1-Benzyl-1H-indol-3-yl)-4-tert-butoxycarbonylamino-pent-2-enoic acid methyl ester(11)

Methyl (triphenylphosphoranylidene)acetate (1.06 g, 3.185 mmol) and [2-(1-Benzyl-1H-indol-3-yl)-1-formyl-ethyl]-carbarnic acid tert-butyl ester (1.204 g, 3.185 mmol) in THF (16 mL) were stirred overnight under argon. The solvent was removed, $Et_2O$ added and the solution filtered. The filtrate was concentrated and the residue subject to column chromatography (silica gel, 25% EtOAc/petroleum ether, Rf 0.77 50% EtOAc/petroleum ether) to afford the title compound (1.034 g, 75%). $^1$H NMR (CDCl$_3$) δ 7.59 (1H, d, J=7.68 Hz), 7.27-6.98 (10H, m), 6.94 (1H, s), 5.86 (1H, d, J=15.9 Hz), 5.24 (2H, s), 4.69 (1H, br s), 3.68 (3H, s), 3.04 (2H, br s), 1.39 (9H, s). $^{13}$C NMR (CDCl$_3$) δ 166.6, 155.1, 148.7, 137.4, 136.6, 128.7, 128.2, 127.5, 126.9, 126.7, 125.6, 121.9, 120.4, 119.4, 119.0, 109.7, 79.7, 51.8, 51.6, 49.9, 30.5,28.3. ISMS: 435 (M+H).

(R)-4-tert-Butoxycarbonylamino-5-[1-(3-phenyl-allyl)-1H-indol-3-yl]-pent-2-enoic acid methyl ester (12)

Methyl (triphenylphosphoranylidene)acetate (1.16 g, 3.465 mmol) and {1-formyl-2-[1-(3-phenyl-allyl)-1H-indol-3-yl]-ethyl}-carbamic acid tert-butyl ester (1.4 g, 3.465 mmol) in THF (19 mL) were stirred overnight under argon. The solvent was removed, $Et_2O$ added and the solution filtered. The filtrate was concentrated and the residue subject to column chromatography (silica gel, 25% EtOAc/petroleum ether) to afford the title compound (1.238 g, 78%), mp 119.3-120.6° C. $^1$H NMR (CDCl$_3$) δ 7.59 (1H, d, J=7.71

Hz), 7.36-7.01 (9H, m), 6.97 (1H, s), 6.45 (1H, d, J=6.45 Hz), 6.29 (1H, dt, J=5.58 15.93 Hz), 5.88 (1H, d, J=15.93 Hz), 4.82 (2H, d, J=5.4 Hz), 4.69 (1H, br s), 3.65 (3H, s), 3.04 (2H, br s), 1.38 (9H, s), $^{13}$C NMR (CDCl$_3$) δ 166.6, 155.1, 148.7, 136.4, 136.1, 132.3, 128.5, 128.2, 127.8, 126.4, 124.7, 121.8, 120.4, 119.3, 119.0, 109.6, 109.5, 79.7, 51.7, 51.5, 48.2, 30.4, 28.2. ISMS: 461 (M+H).

(R)-4-Amino-5-(1-benzyl-1H-indol-3-yl)-pent-2-enoic acid methyl ester (13)

5-(1-Benzyl-1H-indol-3-yl)-4-tert-butoxycarbonylamino-pent-2-enoic acid methyl ester (500 mg, 1.152 mmol) was treated with TFA (2.5 mL) in CH$_2$Cl$_2$ (25 mL). The reaction was complete in 1 h. The solvent and TFA were removed. Trituration with Et$_2$O afforded the trifluoroacetic acid salt (469 mg, 91%). The free amine was isolated as a viscous gum and characterised. $^1$H NMR (CDCl$_3$) δ 7.61 (1H, d, J=7.2Hz), 7.20-7.02 (9H, m), 6.99 (1H, s), 5.97 (1H, dd, J=1.43, 15.71 Hz), 5.28 (2H, s), 3.73 (3H, s), 3.88 (1H, m), 3.06 (1H, dd, J=4.71, 14.27 Hz), 2.82 (1H, dd, J=8.22, 14.27 Hz), 1.52 (2H, br s). $^{13}$C NMR (CDCl$_3$) δ 166.9, 152.2, 137.4, 136.7, 128.7, 128.0, 127.5, 126.9, 126.7, 121.9, 119.5, 119.2, 118.9, 110.8, 109.7, 52.9, 51.4, 49.8, 33.1. ISMS: 335 (M+H).

(R)-4-Amino-5-[1-(3-phenyl-allyl)-1H-indol-3-yl]-pent-2-enoic acid methyl ester (14)

4-tert-Butoxycarbonylamino-5-[1-(3-phenyl-allyl)-1H-indol-3-yl]-pent-2-enoic acid methyl ester (500 mg, 1.087 mmol) was treated with TFA (2.5 mL) in CH$_2$Cl$_2$ (25 mL). The reaction was complete in 1 h. The solvent and TFA were removed. Trituration with Et$_2$O afforded the trifluoroacetic acid salt (257 mg, 50%). The free amine was isolated as a viscous gum and characterised. $^1$H NMR (CDCl$_3$) δ 7.61 (1H, d, 7.68 Hz), 7.38-7.02 (10H, m), 5.99 (1H, dd, J=1.47, 15.72 Hz), 4.85 (2H, d, J=4.47 Hz), 3.71 (3H, s), 3.88 (1H, m), 3.07 (1H, dd, J=5.1, 14.19 Hz), 2.81 (1H, dd, J=8.28, 14.19 Hz), 1.6 (2H, br s), $^{13}$C NMR (CDCl$_3$) δ 166.8. 152.1, 136.3, 135.9, 132.1, 128.3, 127.9, 127.6, 126.2, 124.6, 121.6, 119.3, 118.9, 118.9, 110.5, 109.5, 52.7, 51.3, 47.9, 32.9. ISMS: 361 (M+H).

(R)-5-(1-Benzyl-1H-indol-3-yl)-4-(7-phenyl-heptanoylamino)-pent-2-enoic acid methyl ester (15)

A solution of 7-phenylheptanoic acid (92 mg, 0.447 mmol), BOP (217 mg, 0.491 mmol) and DIPEA (69 mg, 93 μL, 0.535 mmol) in THF (2.5 mL) was stirred for 10 min. To this was added a solution of the trifluoroacetic acid salt of 4-amino-5-(1-benzyl-1H-indol-3-yl)-pent-2-enoic acid methyl ester (200 mg, 0.446 mmol) and DIPEA (173 mg, 233 μL, 1.34 mmol) in THF (2.5 mL). The mixture was stirred overnight at room temperature. The solvent was removed and the crude material subject to column chromatography (50% EtOAc/petroleum ether, Rf 0.66) to afford the title compound (197 mg, 85%). $^1$H NMR (CDCl$_3$) δ 7.59 (1H, d, J=7.26 Hz), 6.94-7.28 (15H, m), 5.81 (1H, d, J=15.81 Hz), 5.48 (1H, d, J=8.34 Hz), 3.59 (2H, s), 5.05 (1H, m), 3.12 (1H, dd, J=6.42, 14.49 Hz), 3.04 (1H, dd, J=5.85, 14.49 Hz), 2.57 (2H, t, J=7.64 Hz), 2.07 (2H, t, J=7.67 Hz), 1.9-1.2 (8H, m). $^{13}$C NMR (CDCl$_3$) δ 172.5, 166.5, 148.1, 142.6, 137.3, 136.6, 128.7, 128.4, 128.3, 128.2, 127.6, 126.9, 126.7, 125.6, 122.1, 120.8, 119.6, 118.8, 109.9, 109.4. 51.6, 49.9, 50.2, 36.7, 35.8, 31.2, 29.9, 29.0, 28.9, 25.4. ISMS: 523 (M+H).

(R)-5-[1-(3-Phenyl-allyl)-1H-indol-3-yl]-4-(7-phenyl-heptanoylamino)-pent-2-enoic acid methyl ester (16)

A solution of 7-phenylheptanoic acid (87 mg, 0.422 mmol), BOP (205 mg, 0.464 mmol) and DIPEA (65.38 mg, 88 μL, 0.506 mmol) in THF (2.5 mL) was stirred for 10 min. To this was added a solution of the trifluoroacetic acid salt of 4-amino-5-[1-(3-phenyl-allyl)-1H-indol-3-yl]-pent-2-enoic acid methyl ester (200 mg, 0.422 mmol) and DIPEA (163 mg, 220 μL, 1.27 mmol) in THF (2.5 mL). The mixture was stirred overnight at room temperature. The solvent was removed and the crude material subject to column chromatography (50% EtOAc/petroleum ether, Rf 0.66) to afford the title compound (133 mg, 55%). $^1$H NMR (CDCl$_3$) δ 7.58 (1H, d, J=8.1 Hz), 7.36-7.09 (12H, m), 7.02-6.95 (2H, m), 6.45 (1H, d, J=15.78 Hz), 6.29 (1H, dt, J=5.63, 15.78 Hz), 5.82 (1H, d, J=15.69 Hz), 5.52 (1H, d, J=8.25 Hz), 5.01-5.09 (1H, m), 4.82 (2H, d, J=5.49 Hz), 3.66 (3H, s), 3.12 (1H, dd, J=6.35, 14.69 Hz), 3.04 (1H, dd, J=6.17, 14.69 Hz), 2.55 (2H, t, J=7.69 Hz), 2.07 (2H, t, J=7.64 Hz), 1.59-1.46 (4H, m), 1.25-1.23 (4H, m). $^{13}$C NMR (CDCl$_3$) δ 172.5, 166.6, 148.1, 142.7, 136.4, 136.1, 132.5, 128.6, 128.4, 128.2, 127.9, 126.5, 125.6, 124.6, 120.8, 122.0, 119.5, 118.8, 109.8, 109.2, 51.6, 50.2, 48.3, 36.7, 35.8, 31.2, 29.9, 29.0, 28.9, 25.4. ISMS: 549 (M+H).

(S)-5-(1-Benzyl-1H-indol-3-yl)-4-(7-phenyl-heptanoylamino)-pentanoic acid methyl ester (17)

5-(1-Benzyl-1H-indol-3-yl)-4-(7-phenyl-heptanoylamino)-pent-2-enoic acid methyl ester (67 mg, 0.128 mmol) in MeOH (40 mL) was hydrogenated at 15 psi for 15 min using 10% Pd/C. The solution was filtered and the solvent removed to afford the title compound (56 mg, 83%), mp 107.1-109.2° C. $^1$H NMR (CDCl$_3$) δ 1.21-1.34 (4H, m), 1.47-1.77 (5H, m), 1.87-1.98 (1H, m), 2.04 (2H, t, J=7.53 Hz), 2.26-2.44 (2H, m), 2.57 (2H, t, J=7.69 Hz), 2.91 (1H, dd, J=6.53, 14.63 Hz), 2.98 (1H, dd, J=5.52, 14.63 Hz), 3.62 (3H, s), 4.22-4.33 (1H, m), 5.26 (2H, s), 5.42 (1H, d, J=5.42), 6.96 (1H, s), 7.08-7.18 (7H, m), 7.24-7.28 (6H, m), 7.64 (1H, 7.26 Hz). $^{13}$C NMR (CDCl$_3$) δ 174.3, 172.8, 142.7, 137.5, 136.6, 128.7, 128.6, 128.4, 128.2, 127.6, 126.8, 126.8, 125.6, 121.9, 119.3, 119.2, 110.8, 109.7, 51.7, 49.9, 49.5, 36.9, 35.8, 31.2, 31.0, 30.6, 29.1, 29.1, 28.9, 25.5. ISMS: 525 (M+H).

(S)-4-(7-Phenyl-heptanoylamino)-5-[1-(3-phenyl-propyl)-1H-indol-3-yl]-pentanoic acid methyl ester (18)

5-[1-(3-Phenyl-allyl)-1H-indol-3-yl]-4-(7-phenyl-heptanoylamino)-pent-2-enoic acid methyl ester (118 mg, 0.215 mmol) in MeOH (60 mL) was hydrogenated at 15 psi for 15 minutes using 10% Pd/C. The solution was filtered and the solvent removed to afford the title compound (111 mg, 93%). ESMS 553 (M+H$^+$), mp 79.4-81° C. $^1$H NMR (CDCl$_3$) δ 7.62 (1H, d, J=7.74 Hz). 7.31-7.07 (13H, m), 6.93 (1H, s), 5.43 (1H, d, J=8.37 Hz), 4.32-4.22 (1H, m), 4.08 (2H, t, J=6.96 Hz), 3.62 (3H, s), 2.97 (1H, dd, J=5.37, 14.43 Hz), 2.91 (1H, dd, J=6.54, 14.43 Hz), 2.62 (2H, t, J=7.62 Hz), 2.57 (2 h, t, J=7.73 Hz), 2.41-2.10 (4H, m), 2.06 (2H, t, J=7.62 Hz), 1.97-1.26 (10H, m). $^{13}$C NMR (CDCl$_3$) δ 174.3, 172.9, 142.7, 140.9, 136.2, 132.1, 128.5, 128.4, 128.3, 128.2, 126.4, 126.1, 125.6, 121.6, 119.1, 119.0, 110.2, 109.4, 51.6, 49.5, 45.5, 36.9, 35.8, 32.9, 31.5, 31.2, 31.0, 30.6, 29.1, 28.9, 25.6. ISMS: 553 (M+H).

(S)-5-(1-Benzyl-1H-indol-3-yl)-4-(7-phenyl-heptanoylamino)-pentanoic acid (19)

To a solution of 5-(1-benzyl-1H-indol-3-yl)-4-(7-phenyl-heptanoylamino)-pentanoic acid methyl ester (48 mg, 0.092 mmol) in MeOH (0.5 mL) was added KOH (100 mg, 1.79 mmol) in water (0.5 mL). THF (1 mL) was added to homogenise the solution and the reaction was complete in 40 min. The solvents were removed and water added. Upon washing with $Et_2O$ the aqueous layer was acidified with aqueous HCl and the resultant precipitate filtered. Upon drying the solid was recrystallised from $THF/Et_2O$ to afford the title compound (30 mg, 64%), mp 130.4-131.9° C. $^{13}C$ NMR (DMSO-d6) δ 174.3, 171.8, 142.3, 138.4, 135.9, 128.4, 128.2, 128.2, 127.2, 127.1, 126.8, 125.5, 121.1, 118.9, 118.5, 111.3, 109.9, 48.9, 48.6, 35.5, 35.1, 30.9, 30.7, 30.5, 29.1, 28.5, 28.4, 25.2. ISMS: 511 (M+H).

(S)-4-(7-Phenyl-heptanoylamino)-5-[1-(3-phenyl-propyl)-1H-indol-3-yl]-pentanoic acid (20)

To a solution of 4-(7-phenyl-heptanoylamino)-5-[1-(3-phenyl-propyl)-1H-indol-3-yl]-pentanoic acid methyl ester (95 mg, 0.172 mmol) in MeOH (0.5 mL) was added KOH (100 mg, 1.79 mmol) in water (0.5 mL). THF (1 mL) was added to homogenise the solution and the reaction was complete in 40 minutes. The solvents were removed and water added. Upon washing with ether the aqueous layer was acidified with aqueous HCl and the resultant precipitate filtered. Upon drying the solid was recrystallised from $THF/Et_2O$ to afford the title compound (70 mg, 76%), mp 100-101.5° C. $^1H$ NMR (DMSO-$d_6$) δ 7.64-7.59 (2H, m), 7.35-7.08 (12H, m), 7.03-6.98 (1H, m), 4.10 (2H, t, J=6.59 Hz), 4.04 (1H, br s), 2.84 (1H, dd, J=6.65, 14.39 Hz), 2.78 (1H, dd, J=6.45, 14.39 Hz), 2.55-2.49 (4H, m), 2.34-2.12 (2H, m), 2.05-2.00 (4H, m), 1.86-1.75 (1H, m), 1.66-1.44 (5H, m), 1.21 (4H, m), $^{13}C$ NMR (DMSO-$d_6$) □ 174.4, 171.9, 142.3, 141.3, 135.9, 128.3, 128.2, 128.0, 126.5, 125.8, 125.5, 120.9, 118.9, 118.3, 117.9, 110.9, 109.5, 35.6, 35.1, 32.4, 31.5, 30.9, 30.7, 30.5, 29.2, 28.5, 28. 5, 25.3. ISMS: 539 (M+H).

Example 2 (See Scheme 2)

2-tert-Butoxycarbonylamino-3-(1H-imidazol-4-yl)-propionic acid benzyl ester (22)

2-tert-Butoxycarbonylamino-3-(1H-imidazol-4-yl)-propionic acid (25 g, 97.92 mmol), benzyl bromide (17.59 g, 12.2 mL, 0.103 mmol) and potassium carbonate (16.9 g, 0.122 mol) in DMF (250 mL) were stirred overnight under argon. The solvent was removed and the residue taken up into water and $CH_2Cl_2$. The organic layer was washed with water and brine, dried and filtered. The solvent was removed and the residue subject to column chromatography (silica gel, 75% EA/PE to afford 3-(1-benzyl-1H-imidazol-4-yl)-2-tert-butoxycarbonylamino-propionic acid benzyl ester (6.79 g, 16%) Rf 0.6, followed by 10% MeOH/EA to afford the title compound (15.832 g, 47%) Rf 0.1). ESMS 346 (M+H$^+$) Mpt 100.5-101.7° C. $^1H$ NMR (500 MHz, CDCl$_3$) δ 1.42 (9H, s), 3.02 (2H, m), 4.51 (1H, m), 5.19 (1H, d, J=12.1 Hz), 5.08 (1H, d, J=12.1 Hz), 5.81 (1H, m), 7.35 (5H, m), 7.47 (1H, s). $^{13}C$ NMR (CDCl$_3$) δ 28.22, 29.48, 53.67, 66.88, 79.88, 116.23, 126.63, 128.26, 128.45, 133.61, 135.19, 135.39, 155.59, 171.97.

2-tert-Butoxycarbonylamino-3-(1-trityl-1H-imidazol-4-yl)-propionic acid benzyl ester (23)

A solution of 2-tert-butoxycarbonylamino-3-(1H-imidazol-4-yl)-propionic acid benzyl ester (6.062 g, 17.57 mmol) and triethylamine (3.57 g, 4.90 mL, 35.14 mmol) in CHCl$_3$ (50 mL) was cooled to 0° C. under argon. Trityl chloride (4.9 g, 17.57 mmol) in CHCl$_3$ was added and after 20 minutes the solution became opaque. The solution was stirred at 0° C. overnight, warmed to room temperature, washed with water and brine, dried over MgSO$_4$ and filtered. The solvent was removed and the crude material was chromatographed (silica gel, 25% EA/PE, Rf 0.78 75% EA/PE) to afford the title compound as a viscous gum (7.58 g, 74%). ESMS 588 (M+H$^+$) $^1H$ NMR (500 MHz, CDCl$_3$) δ 1.42 (9H, s), 2.98 (1H, dd, J=4.65, 14.53 Hz), 3.05 (1H, dd, J=5.05, 14.53 Hz), 4.58 (1H, m), 5.02 (2H, d, J=2.55 Hz), 6.06 (1H, d, J=8.25 Hz), 6.47 (1H, s), 7.09 (6H, m), 7.26 (4H, m), 7.29 (10H, m), 7.36 (1H, s). $^{13}C$ NMR (CDCl$_3$) δ 28.11, 29.87, 53.61, 66.37, 74.95, 79.12, 119.30, 127.78, 128.16, 129.48, 135.29, 136.23, 138.48, 142.01, 155.34, 171.44.

2-tert-Butoxycarbonylamino-3-(1-trityl-1H-imidazol-4-yl)-propionic acid (24)

2-tert-Butoxycarbonylamino-3-(1-trityl-1H-imidazol-4-yl)-propionic acid benzyl ester (6 g, 10.22 mmol) in MeOH (20 mL) was added potassium hydroxide (1.14 g, 20.44 mmol) in water (10 mL). THF (25 mL) was added to homogenise the solution. The solution was stirred for 1 hour and the solvents removed. Water was added and extracted with $Et_2O$. The aqueous layer was acidified with dilute aqueous HCl and extracted with $Et_2O$. The $Et_2O$ was washed with water, brine, dried over MgSO$_4$ and filtered. The solvent was removed to give the title compound (4.792 g, 94%). ESMS 498 (M+H$^+$) Mpt 101.5-103.6° C. $^1H$ NMR (CDCl$_3$) δ 1.35 (9H, s), 3.25 (1H, dd, J=5.37, 14.9), 3.39 (1H, dd, J=4.83, 14.9), 4.46-4.52 (1H, m), 5.66, (1H, d, J=5.91), 6.83 (1H, s), 7.07-7.10 (3H, m), 7.26-7.30 (8H, m), 7.42-7.45 (4H, m), 8.13 (1H, s). $^{13}C$ NMR (CDCl$_3$) δ 28.26, 29.00, 53.07, 76.14, 78.98, 120.88, 128.21, 128.32, 129.63, 133.68, 137.22, 141.52, 154.90, 173.60.

[1-(Methoxy-methyl-carbamoyl)-2-(1-trityl-1H-imidazol-4-yl)-ethyl]-carbamic acid tert-butyl ester (25)

2-tert-Butoxycarbonylamino-3-(1-trityl-1H-imidazol-4-yl)-propionic acid (4.56 g, 9.18 mmol), DIPEA (3.55 g, 4.79 mL, 27.53 mmol), BOP (4.26 g, 9.63 mmol) and N,O-dimethylhydroxylamine hydrochloride (940 mg, 9.63 mmol) in DMF (100 mL) were stirred overnight. The DMF was removed and $CH_2Cl_2$ added. The solution was washed with dilute aqueous HCl (1M, 4X), water and brine. The solution was dried, filtered and the solvent removed. The product was chromatographed (silica gel, EA/PE, Rf 0.38 EA) to afford the title compound (4.475 g, 90.4%). ESMS 541 (M+H$^+$) $^1H$ NMR (500 MHz, CDCl$_3$) δ 1.39 (9H, s), 2.92 (1H, dd, J=6.13, 14.45), 2.98 (1H, dd, J=5.63, 14.45), 3.13 (3H, s), 3.73 (3H, s), 4.87 (1H, m), 5.61 (1H, d, J=6.95 Hz), 6.57 (1H, s), 7.11 (6H, m), 7.32 (9H, m), 7.46 (1H, s). $^{13}C$ NMR (CDCl$_3$) 28.19, 30.34, 31.02, 50.55, 61.49, 75.62, 79.34, 119.74, 127.98, 129.59, 135.19, 137.95, 141.77, 155.19, 171.77.

[1-Formyl-2-(1-trityl-1H-imidazol-4-yl)-ethyl]-carbamic acid tert-butyl ester (26)

A suspension of lithium aluminum hydride (263 mg, 6.92 mmol) in THF (20 mL) was added slowly to [1-(methoxy-methyl-carbamoyl)-2-(1-trityl-1H-imidazol-4-yl)-ethyl]-carbamic acid tert-butyl ester (3.4 g, 6.3 mmol) in THF (75 mL) at −20° C. The reaction was complete (silica gel, EA, Rf 0.48) in 15 minutes. Saturated sodium potassium tartrate (10 mL) was added, and the solvent removed. Water was added and the residue extracted with $Et_2O$. The $Et_2O$ was washed with brine, dried and filtered. Removal of the solvent gave the title compound (2.552 g, 84%). ESMS 482 (M+H$^+$) $^1$H NMR ( ) $^{13}$C NMR ( )

4-tert-Butoxycarbonylamino-5-(1-trityl-1H-imidazol-4-yl)-pent-2-enoic acid ethyl ester (27)

Ethyl (triphenylphosphoranylidene)acetate (1.52 g, 4.37 mmol) and [1-formyl-2-(1-trityl-1H-imidazol-4-yl)-ethyl]-carbamic acid tert-butyl ester (2.1 g, 4.38 mmol) in THF (35 mL) were stirred overnight under argon. The solvent was removed, $Et_2O$ added and the solution filtered. The filtrate was concentrated and the residue subject to column chromatography (silica gel, 25% EA/PE, Rf 0.65 50% EA/PE) to afford the title compound (1.6 g, 67%). ESMS 552 (M+H$^+$) Mpt . $^1$H NMR (300 MHz, CDCl$_3$) δ 1.28 (3H, t, J=7.5), 1.34 (9H, s), 3.01-3.05 (2H, m), 4.19 (2H, q, J=7.05), 4.47-4.57 (1H, m), 6.01 (1H, dd, J=1.5, 15.9), 6.46 (1H, d, J=9.3), 6.86 (1H, s), 6.89 (1H, dd, J=5.1, 15.9), 7.07-7.11 (5H, m), 7.21-7.3 (2H, m), 7.4-7.44 (8H, m), 8.11 (1H, s). $^{13}$C NMR (300 MHz, CDCl$_3$) δ 166.14, 155.87, 139.86, 135.20, 132.21, 129.49, 129.70, 129.01, 128.18, 122.33, 121.19, 79.74, 78.78, 60.76, 52.09, 30.12, 28.35, 14.32.

4-Amino-5-(1H-imidazol-4-yl)-pent-2-enoic acid ethyl ester (28)

A representative procedure is as follows. 4-tert-Butoxycarbonylamino-5-(1-trityl-1H-imidazol-4-yl)-pent-2-enoic acid ethyl ester (100 mg, 0.181 mmol) was stirred with TFA (5 mL) overnight under an atmosphere of argon. The TFA was removed and the residue triturated with $Et_2O$. The remaining solid was subject to preparative reverse phase HPLC (30% B to 100% B over 20 min) to yield after lyophilization a gum (20 mg, 53%). $^1$H NMR (300 MHz, d$_6$-DMSO) δ 1.19 (3H, t, J=7.02), 3.19 (2H, br s), 4.12 (2H, q, J=7.02), 4.33 (1H, m), 6.09 (1H, d, J=15.87), 6.76 (1H, dd, J=7.14, 15.87), 7.49 (1H, br s), 9.01 (1H, br s). $^{13}$C NMR (d$_6$-DMSO) δ 164.76, 141.83, 134.64, 127.39, 125.08, 118.09, 60.58, 50.03, 27.57, 14.06.

5-(1H-Imidazol-4-yl)-4-(7-phenyl-heptanoylamino)-pent-2-enoic acid ethyl ester (29)

A solution of 7-phenyl heptanoic acid (2.49 g, 12.08 mmol) in THF was treated with DIPEA (2.65 mL, 15.1 mmol) and BOP (5.6 g, 12.68 mmol). After 5 min a solution of 4-amino-5-(1H-imidazol-4-yl)-pent-2-enoic acid ethyl ester (1.26 g, 6.04 mmol) and DIPEA (3.15 mL, 18.12 mmol) in THF was added slowly and the reaction stirred for an hour. The solvent was removed and the residue taken up into EA. It was washed successively with water, $NaHCO_3$ and brine. The solution was dried, filtered and the solvent removed to yield crude product. This material was subject to column chromatography (silica, EA/PE to EA/MeOH) to give a brown gum (1.36 g, 88%). This in turn was subject to reverse phase HPLC (30% B to 100% B over 30 min) to yield the title compound as a white powder (468 mg, 30%). $^1$H NMR (d$_6$-Acetone) δ 1.23, 1.23-1.37, 1.47-1.61, 2.13, 2.17, 2.58 (2H, t, J=), 3.02 (1H, dd, J=10.47, 15.02), 3.29 (1H, dd, J=4.32, 15.02), 4.14 (2H, q, J=7.14), 5.98 (1H, dd, J=1.71, 15.66), 6.97 (1H, dd, J=5.08, 15.66), 7.14-7.28 (5H, m), 7.49 (1H, s), 8.15 (1H, d, J=8.67), 8.78 (1H, d, J=1.29). $^{13}$C NMR (d$_6$-Acetone) δ 173.01, 166.39, 148.23, 143.59, 134.30, 131.75, 129.22, 129.06, 126.40, 122.08, 117.94, 60.83, 50.59, 45.12, 36.46, 32.23, 29.77, 29.71, 26.29, 14.58.

5-[1-(3-Phenyl-allyl)-1H-imidazol-4-yl]-4-(7-phenyl-heptanoylamino)-pent-2-enoic acid ethyl ester (30)

The 5-(1H-Imidazol-4-yl)-4-(7-phenyl-heptanoylamino)-pent-2-enoic acid ethyl ester (100 mg, 0.25 mmol) in DMF (1 mL) was treated with NaH (10 mg, 60%, 0.25 mmol) at room-temperature. After 5 minutes cinnamyl bromide (50 mg, 0.25 mmol) was added, and the solution stirred overnight. Analytical HPLC showed the product was a 60:40 mixture of τ (required) and π (undesired) isomers respectively. The solution as taken up into water and acetonitrile and subject to reverse phase HPLC (30% B to 100% B over 25 min). The product, a mixture of both isomers, was obtained as an oil (88 mg, 68%), ESMS 514 (M+H$^+$). $^{13}$C NMR δ 174.72, 174.67, 174.22, 171.69, 170.52, 166.20, 145.85, 142.93, 138.31, 138.16, 137.81, 137.45, 134.89, 134.81, 133.37, 132.86, 131.49, 131.39, 129.26, 128.98, 128.52, 128.34, 127.04, 125.68, 122.23, 119.68, 119.61, 119.54, 118.93, 114.55, 63.08, 61.90, 60.91, 60.79, 57.59, 54.77, 52.59, 52.53, 51.49, 50.21, 37.04, 36.14, 35.99, 33.44, 31.44, 29.61, 29.18, 29.13, 29.03, 28.97, 25.67, 25.62, 25.46, 14.27, 14.05.

4-(7-Phenyl-heptanoylamino)-5-[1-(3-phenyl-propyl)-1H-imidazol-4-yl]-pentanoic acid ethyl ester (31)

A solution of 5-[1-(3-phenyl-allyl)-1H-imidazol-4-yl]-4-(7-phenyl-heptanoylamino)-pent-2-enoic acid ethyl ester (110 mg, 0.21 mmol) and Pd/C (50 mg) in ethanol (100 mL) was subject to hydrogenation (42 psi) for 2 hr. The solution was filtered and the solvent removed. The residue, ESMS 518 (M+H$^+$) was hydrolysed directly without characterisation.

4-(7-Phenyl-heptanoylamino)-5-[1-(3-phenyl-propyl)-1H-imidazol-4-yl]-pentanoic acid (32)

Hydrolysis of crude ethyl ester 80 mg (KOH/MeOH, THF, water) gave the crude acid 40 mg, 50%. The product was isolated by RP-HPLC giving 25 mg, 32% of the product as a colourless glass. $^1$H NMR (500 MHz, acetone-d$_6$) δ 8.79 (s, 1H), 7.51 (s, 1H), 7.30-7.11 (m, 10H), 4.33 (t, J=7 Hz, 2H), 4.21 (m, 1H), 3.04 (dd, J=14.9, 4.1 Hz, 1H), 2.86 (dd, J=14.9, 10.4 Hz, 1H), 2.66 (m, 2H), 2.55 (m, 2H), 2.44-2.31 (m, 2H), 2.29-2.21 (m, 2H), 2.16-2.05 (m, 2H), 1.91 (m, 1H), 1.74 (m, 1H), 1.59-1.51 (m, 2H), 1.51-1.42 (m, 2H), 1.31-1.16 (m, 4H). $^{13}$C NMR (CDCl$_3$) δ 174.7, 173.7, 143.6, 141.5, 134.7, 133.8, 129.3, 129.3, 129.2, 129.0, 127.0, 126.4, 119.9, 49.6, 49.5, 36.6, 36.5, 32.9, 32.5, 32.2, 31.2, 31.1, 30.8, 30.3, 29.8, 29.4, 26.3. ISMS 490 (M+H$^+$).

Example 3 (See Scheme 3)

2-tert-Butoxycarbonylamino-3-(3-phenyl-allyloxy)-propionic acid 3-phenyl-allyl ester (34)

To a stirred solution of Boc-L-serine (5.0 g, 24 mmol) in DMF (20 mL) was added sodium hydride (60% in oil, 1.95 g, 48 mmol) portionwise over 20 minutes, with ice cooling. The first equivalent produced a clear solution of monosodium salt, the second equivalent produced a colourless precipitate. The ice bath was removed and stirring was continued for 30 minutes. The solution was again cooled in ice and cinnamyl bromide (7.2 ml, 9.60 g, 48 mmol) was added dropwise over 10 minutes. The mixture was stirred at room temperature for 2 hours and the solvent was removed under reduced pressure. The residue was partitioned between water (200 mL) and ether (200 mL) and the organic extract was washed with water (2×200 mL), dried ($Na_2SO_4$), filtered and evaporated under reduced pressure to yield a slightly cloudy yellow oil. $^1$H NMR ($CDCl_3$) δ 7.60-7.10, (10H, m, ArH), 6.65 (1H, d, J=15.37 Hz, =CH), 6.55 (1H, d, J=15.92 Hz, =CH), 6.26 (1H, dt, J=15.37, 6.33 Hz, =CH), 6.18 (1H, ddd, J=15.92, 6.13, 5.91 Hz, =CH), 5.45 (1H, d, J=8.43 Hz, NH), 4.82 (2H, m, $CO_2CH_2$), 4.49 (1H, m, Hα), 4.14 (2H, m, $CH_2$), 3.95 (1H). brd, J=9.2 Hz, Hβ), 3.72 (1H, brd, J=9.2 Hz, Hβ), 1.45 (9H, s, Boc). ISMS: 438(M+H).

2-tert-Butoxycarbonylamino-3-(3-phenyl-allyloxy)-propionic acid (35)

To a stirred solution of the above crude ester (~24 mmol) in methanol (100 mL) was added a solution of sodium hydroxide (0.95 g, 24 mol) in water (5 mL). The mixture was stirred at room temperature for 2 hours and the solvent was removed under reduced pressure. The residue was partitioned between ether (200 mL) and sodium bicarbonate solution (5%, 200 mL) and the aqueous extract was washed with ether (2×200 mL), and then treated with solid citric acid (Caution-foaming) until pH 2 was obtained. The cooled solution was extracted with ether, (2×200 mL), dried ($Na_2SO_4$), filtered and evaporated under reduced pressure to yield a viscous colourless oil (4.33 g, 56% from Boc-(L)-serine). $^1$H NMR ($CDCl_3$) δ (7.50-7.20, 5H, m, ArH), 6.58 (1H, d, J=15.8 Hz, =CH), 6.22 (1H, dd, J=15.8, 6.1 Hz, =CH), 5.48 (1H, d, J=8.1 Hz, NH), 4.49 (1H, m, Hα), 4.18 (2H, d, J=6.1 Hz, $CH_2$), 3.96 (1H, brd, J=9.6 Hz, Hβ), 3.72 (1H, dd, J=9.6, 3.7 Hz, Hβ), 1.45 (9H, s, Boc).). $^{13}$C NMR ($CDCl_3$) δ 174.8, 155.7, 136.4, 133.1, 128.5, 127.8, 126.5, 125.0, 80.3, 72.1, 69.6, 53.7, 28.3. ISMS: 322(M+H).

2-tert-Butoxycarbonylamino-3-(3-phenyl-propoxy)-propionic acid (36)

The above acid (4.174 g, 13 mmol) was hydrogenated in a Parr apparatus in ethanol (70 mL) in the presence of palladium-on-carbon catalyst (10%, 100 mg at 42 psi for 40 minutes. The mixture was filtered through a plug of Celite™, and the solvent was removed under reduced pressure to yield the pure product in quantitative yield as a viscous colourless oil. $^1$H NMR ($CDCl_3$) δ 7.40-7.18 (5H, m, ArH), 5.42 (1H, d, J 8.20 Hz, NH), 4.49 (1H, m, Hα), 3.95 (1H, brd, J=9.5 Hz, Hβ), 3.72 (1H, dd, J=9.5, 4.1 Hz, Hβ), 3.50 (2H, t, J=6.3 Hz, $OCH_2$), 2.68 (2H, t, J=7.6 Hz, $OCH_2$), 1.92 (2H, tt, J=7.6, 6.3 Hz, $CH_2$), 1.49 (9H, s, Boc). ISMS: 324(M+H).

Example 4 (See Scheme 4)

(R)-[2-(4-Benzyloxy-phenyl)-1-(methoxy-methyl-carbamoyl)-ethyl]-carbamic acid tert-butyl ester (38)

DIPEA (28.2 ml, 20.9 g, 162 mmol) was added to a stirred solution of (R)-3-(4-benzyloxy-phenyl)-2-tert-butoxycarbonylamino-propionic acid (20.0 g, 53.9 mmol), BOP (25.00 g, 56.5 mmol) and MeONHMe.HCl (5.52 g, 56.6 mmol) in DMF (300 mL). After stirring 2 h the DMF was evaporated and the residue was dissolved in EtOAc and washed with water, 5% aqueous HCl, saturated aqueous $NaHCO_3$ and brine, then dried with $Na_2SO_4$ and evaporated to a cream solid. This was ground to a powder (22.39 g, 100%), mp 107.1-108.7° C. (lit. mp 107-108° C.) [W. J. Thompson et al, *Tetrahedron Lett*, 1990, 31, 6189]. $^1$H NMR ($CDCl_3$) δ 7.44-7.32 (5H, m), 7.09 (2H, d, J=8.5 Hz), 6.90 (2H, d, J=8.6 Hz), 5.15 (1H, br d, J=7.1 Hz, NH), 5.04 (2H, s, $OCH_2Ph$), 4.91 (1H, br s, Hα), 3.17 (3H, s, NMe), 3.65 (3H, s, OMe), 3.00 (1H, dd, J=6.1, 13.6 Hz, Hβ), 2.83 (1H, dd, J=6.2, 14.2 Hz, Hβ), 1.40 (9H, s, $CMe_3$). $^{13}$C NMR ($CDCl_3$) δ 172.3, 157.7, 155.2, 137.1, 130.4, 128.9, 128.5, 127.9, 127.4, 114.7, 79.6, 70.0, 61.5, 51.6, 38.0, 32.1, 28.3.

(R)-[1-(4-Benzyloxy-benzyl)-2-oxo-ethyl]-carbamic acid tert-butyl ester (39)

$LiAlH_4$ (916 mg, 24.1 mmol) was added cautiously and portionwise during 15 min to a stirred solution of (R)-[2-(4-Benzyloxy-phenyl)-1-(methoxy-methyl-carbamoyl)-ethyl]-carbamic acid tert-butyl ester (10.00 g, 24.1 mmol) in THF (150 mL) at 0° C. under an atmosphere of argon. The ice-bath was removed and the mixture was stirred for 1 h, then poured onto a mixture of ice and $KHSO_4$ (1M aqueous). When the ice had melted the product was extracted into EtOAc. The combined extracts were washed with brine then dried ($Na_2SO_4$) and evaporated to give the aldehyde as pale yellow crystals (8.51 g, 99%), mp 100.3-101.7° C. (lit. mp 98-99° C.).[W. J. Thompson et al, *Tetrahedron Lett.*, 1990, 31, 6819] $^1$H NMR ($CDCl_3$) δ 9.63 (1H, s, CHO), 7.45-7.33 (5H, m), 7.09 (2H, d, J=8.7 Hz), 6.92 (2H, d, J=8.6 Hz), 5.05 (2H, s, $OCH_2Ph$), 4.40 (1H, br s, Hα), 3.07 (2H, d, J=6.7 Hz, Hβ,β), 1.44 (9H, s, $CMe_3$). $^{13}$C NMR ($CDCl_3$) δ 199.6, 156.4, 144.4, 136.8, 130.4, 128.6, 128.5, 128.0, 127.9, 127.5, 115.1, 80.9, 70.0, 46.0, 34.6, 28.3.

(R)-5-(4-Benzyloxy-phenyl)-4-tert-butoxycarbonylamino-pent-2-enoic acid methyl ester (40)

A mixture of (R)-[1-(4-benzyloxy-benzyl)-2-oxo-ethyl]-carbamic acid tert-butyl ester (19.8 g, 0.056 mol) and $Ph_3P=CHCO_2Me$ (18.8 g, 0.056 mol) in dry THF (260 ml) was stirred at room temperature for 4 h. Removal of the solvent in vacuo afforded a gummy residue which was taken up into a mixture of EtOAc/petroleum ether (1:4) and chilled. Trituration of the gum produced a crystalline solid which was broken up and filtered through celite. The filter cake was washed with several small portions of chilled EtOAc/petroleum ether (1:4), and the combined filtrates evaporated to yield a yellow gum (22.5 g) which was purified by chromatography (silica gel, 4:1 petroleum ether/EtOAc) to yield 4 (9.7 g, 42%). $^1$H NMR ($CDCl_3$) δ 7.48-7.28 (5H, m, $OCH_2Ph$), 7.07 (2H, d, J=8.7 Hz, $CH_2PhO$), 6.88 (1H, d, J=15 Hz, CH=), 6.88 (2H, d, J=8.7 Hz, $CH_2PhO$), 5.83 (1H, d, J=15 Hz, CH=), 5.05 (2H, s, $OCH_2Ph$), 4.52 (br s, NH and H), 3.70 (3H, s, $CO_2CH_3$), 2.80 (2H, m, $H_{\beta,\beta}$), 1.40 (9H, s, $CMe_3$). $^{13}C$ NMR ($CDCl_3$) 28.5, 40.1, 51.8, 52.6, 70.2, 80.0, 1115.1, 120.8, 127.6, 128.1, 128.7, 130.6, 137.1, 148.2, 155.1, 157.9, 166.8.

4-Amino-5-(4-benzyloxy-phenyl)-pent-2-enoic acid methyl ester (41)

(R)-5-(4-Benzyloxy-phenyl)-4-tert-butoxycarbony-lamino-pent-2-enoic acid methyl ester (3.0 g, 0.0073 mol) was added to TFA (10 ml) at 0° C. with stirring. After 10 min, ice was added, and the mixture extracted into EtOAc. The extracts were washed with $K_2CO_3$ solution (20% w/v) and brine, dried with $MgSO_4$, and evaporated to afford 2.23 g (98%) of the title compound.

5-(4-Benzyloxy-phenyl)-4R-[2S-tert-butoxycarbony-lamino-3-(3-phenyl-propoxy)-propionylamino]-pent-2-enoic acid methyl ester (42)

(R)-5-(4-Benzyloxy-phenyl)-4-tert-butoxycarbony-lamino-pent-2-enoic acid methyl ester (40) (49 mg, 0.12 mmol) was added to TFA (300 μL) at 0° C. with stirring. After 30 minutes the mixture was cautiously quenched with $K_2CO_3$ solution (1 M, 10 mL) and the mixture extracted into dichloromethane (2 ml). The extract was dried with $Na_2SO_4$, filtered and added to a stirred solution of (36) (39 mg, 0.12 mmol) and HBTU (45 mg, 0.12 mmol) in a mixture of dichloromethane (2 mL), and DIPEA (80 μL). The mixture was stirred at room temperature for 2 hours and evaporated under reduced pressure. The residue was purified by column chromatography (0-20% ethyl acetate in dichloromethane) to give the pure product as a colourless gum (59 mg, 80%), ESMS 617 $(M+H)^+$.

4R-[2S-Amino-3-(3-phenyl-propoxy)-propionylamino]-5-(4-benzyloxy-phenyl)-pentanoic acid (43)

Compound (42) (59 mg, 0.096 mmol) was hydrogenated in methanol (30 mL) in the presence of palladium-on-carbon catalyst (10%, 50 mg) at 14 psi for 30 minutes. Mass Spectrometric analysis indicated the presence of product and debenzylated materials. Accordibgly the filtered reaction mixture was treated with potassium carbonate (13.8 mg, 0.1 mmol) and benzyl bromide (17 mg, 0.1 mmol) in DMF (1 mL) for 5 days at room temperature. The solvent was evaporated under reduced pressure and the residue was treated with sodium hydroxide (4M, 150 mL) in a mixture of THF (1 mL) and methanol (1 mL) at room temperature for 3 hours. The solvents were evaporated under reduced pressure and the residue was taken up in potassium carbonate solution (5%, 5 mL), washing with ether (2×10 mL). The aqueous phase was made acidic with hydrochloric acid (conc.) and extracted into ether (2×10 mL). The combined ether extracts were dried ($Na_2SO_4$), evaporated under reduced pressure and treated with a mixture of dichlotomethane (1 mL) and TFA (1 mL). The mixture was stirred for 2 hours at room temperature and the solvents were evaporated under reduced pressure. The product was purified by RP-HPLC (0-100% B 20 minutes) to yield the product as a colourless solid (3.2 mg). ESMS 515 $(N+H)^+$ Example 5 (See Scheme 5)

3-(3-Phenyl-propoxy)-propionic acid (45)

To a stirred solution of 3-phenyl-1-propanol (1.36 g, 10 mmol) in THF (50 mL) at room temperature was added sodium hydride dispersion in oil (60%, 400 mg) portonwise. The cloudy solution warmed sightly and was stirred at room temperature for 30 minutes, and cooled to 0° in an ice-salt bath. Methyl acrylate (1.1 equivalents) was added, the ice bath was removed and stirring was continued for 30 minutes. The mixture was then cautiously treated with water (10 mL) and stirring was continued at room temperature overnight. The solvents were removed under reduced pressure and the residue was partitioned between water (100 mL) and ether (100 mL). The aqueous portion was made acidic to <pH 1 with concentrated HCl, and extracted with ether(2×50 ml). The ether extract was dried (MgSO4), filtered and evaporated under educed pressure to yield the title compound as a mobile colourless oil (0.684 g, 33%). $^1H$ NMR ($CDCl_3$) δ 9.19 (br s, 1H), 7.4-7.0 (5H, m, ArH), 3.60 (2H, t, J 6.2 Hz, $OCH_2$), 3.36 (2H, t, J 6.2 Hz, $OCH_2$), 2.54 (4H, m, 2×$CH_2$), 1.79 (2H, m, $CH_2$). $^{13}C$ ($CDCl_3$) δ 177.4, 141.7, 128.4, 128.3, 125.7, 70.1, 65.7, 34.8, 31.4, 32.1, 31.0.

5-(4-Benzyloxy-phenyl)-4R-[3-(3-phenyl-propoxy)-propionylamino]-pent-2-enoic acid methyl ester (46)

(R)-5-(4-Benzyloxy-phenyl)-4-tert-butoxycarbony-lamino-pent-2-enoic acid methyl ester (40) (49 mg, 0.12 mmol) was added to TFA (300 μL) at 0° C. with stirring. After 30 minutes the mixture was cautiously quenched with $K_2CO_3$ solution (1 M, 10 mL) and the mixture extracted into dichloromethane (2 ml). The extract was dried with $Na_2SO_4$, filtered and added to a stirred solution of (45) (25 mg, 0.12 mmol) and HBTU (45 mg, 0.12 mmol) in a mixture of dichloromethane (2 mL), and DIPEA (80 μL) of the title compound. The mixture was stirred at room temperature for 2 hours and evaporated under reduced pressure. The residue was purified by column chromatography (40% petroleum ether in dichloromethane) to give the pure product as a colourless gum (52 mg, 87%), ESMS 502 $(M+H)^+$.

Example 6 (See Scheme 6)

Preparation of 7-phenylheptanoic acid (51) (see step (h) in Schemes 1 and 2)

Benzaldehyde (6.63 g, 0.062 mol, 6.35 ml) in dry THF (20 ml) was added dropwise to a stirred suspension of NaH (60% dispersion, 5.51 g, 0.138 mol) and (5-carboxyhexyl)-triphenylphosphonium bromide (30 g, 0.066 mol) in dry THF (260 ml). After stirring overnight, the solvent was evaporated to dryness, and the residue taken up into water (300 ml). The solution was made alkaline (pH 12-14) with NaOH solution (4 M) and extracted with EtOAc. The basic solution was then acidified (conc. HCl), extracted with $Et_2O$, and the combined extracts washed with brine and dried with $MgSO_4$. Removal of the solvent afforded 16.5 g of crude product which was purified by chromatography (silica, 1:5 EtOAc/petroleum ether, increasing to 1:1 EtOAc/petroleum ether toward completion) to give 10.81 g (85%) of E-/Z-7-phenylhept-6-ene-oic acid (~1:1 mixture) as a pale yellow oil. Hydrogenation of the unsaturated acid (10% Pd—C, EtOAc) afforded the saturated compound (51): $^1H$ NMR ($CDCl_3$) δ 11.57 (br s, 1H), 7.20 (m, 5H), 2.58 (t, J=7.7 Hz, 2H), 2.31 (t, J=7.5 Hz, 2H), 1.61 (m, 4H), 1.33 (m, 4H). $^{13}C$ NMR ($CDCl_3$), δ 180.8, 142.7, 128.5, 128.4, 125.7, 36.0, 34.2, 31.4, 29.0, 24.7.

Example 7 (See Scheme 7)

Synthesis of (3-Phenoxy-propyl)-phosphonic acid dimethyl ester (52).

Dimethylphosphite (5.0 g, 45 mmol) was cautiously added to a suspension of NaH (60% dispersion, 2.0 g, 50 mmol) in DMF (45 mL) at 0°. After 2 h, 3-phenoxy propylbromide (10.75 g, 50 mmol) was added, and the mixture stirred at rt for 48 h. The solvent was removed under reduced pressure, the residue dissolved in water (100 mL), extracted with $Et_2O$, and the combined extracts washed with water, brine and dried ($MgSO_4$). The solution was concentrated at reduced pressure to give 10.28 g of crude product. A portion of the crude material (5 g) was distilled to afford 52 (3.4 g, 63%) as a colourless oil. $^{13}C$ NMR ($CDCl_3$) δ 21.4 (d, J=141.8 Hz), 22.7 (d, J=4.5 Hz), 52.5 (d, J=6.8 Hz), 67.2 (d, J=15 Hz), 114.6, 121.0, 129.6, 158.8. ESMS 245 $(M+H)^+$.

Synthesis of (3-Phenoxy-propyl)-phosphonochloridate monomethyl ester (53).

$LiOH.H_2O$ (182 mg, 4.3 mmol) in water (2.5 mL) was added to 52 (500 mg, 2.0 mmol) in THF (4 mL) and the mixture refluxed for 48 h. The solution was diluted with water, washed with $Et_2O$, and acidified to pH 1 (conc. HCl). The solution was then saturated with solid NaCl, extracted with EtOAc, and the combined extracts dried ($MgSO_4$). Concentration of the solvent under reduced pressure gave 434 mg (92%) of the acid. A portion of this (57 mg, 0.25 mmol) was dissolved in $CH_2Cl_2$ (3 mL) and DMF (2 μL) was added followed by dropwise addition of oxalyl chloride (43 μL, 0.5 mmol) at 0°. After 10 min at 0°, the solution was warmed to rt for 2 h and concentrated to dryness to give 53 (~62 mg). This material was used immediately without further purification as described below.

Synthesis of (R)-[2-(4-Denzyloxy-phenyl)-1-hydroxymethyl-ethyl]-carbamic acid tert-butyl ester (54).

$LiAlH_4$ (107 mg, 2.8 mmol) was added portion-wise over 5 min to a chilled (ice) stirred solution of (39) (1.0 g, 2.8 mmol) in dry THF (25 mL) under argon. After 45 min, EtOAc (10 mL) was added and the biphasic solution poured onto a mixture of ice (40 g) and citric acid solution (10% w/v, 50 mL). The mixture was extracted with EtOAc, and the combined extracts washed with brine, dried ($MgSO_4$) and evaporated to afford 54 in quantitative yield as a pale orange solid. $^1H$ NMR ($CDCl_3$) δ 1.42 (s, 9H), 2.77 (m, 2H), 3.53 (dd, J=11, 6 Hz, 1H), 3.65 (dd, J=11, 4 Hz), 3.83 (m, 1H), 4.81 (m, 1H), 5.04 (s, 2H), 6.91 (d, J=8 Hz, 2H), 7.13 (d, J=8 Hz, 2H), 7.27-7.50 (m, 5H). ESMS 3.58 $(M+H)^+$.

Synthesis of (R)-7-Phenyl-heptanoic acid [2-(4-benzyloxy-phenyl)-1-hydroxymethyl-ethyl]-amide (55).

Compound 54 (1.0 g, 2.8 mmol) was added to TFA solution (4 mL) at 0° with stirring. After 5 min, the mixture was warmed to rt for 5 min, and then quenched with ice. The solution was extracted three times with a mixture of EtOAc: 1-butanol (2:1) and the combined extracts washed three times with water. Evaporation of the solvent under reduced pressure afforded 649 mg (90%/o) of the amine. Without further purification, a portion of this (453 mg, 1.7 mmol) was coupled to 7-phenylheptanoic acid (399 mg, 1.9 mmol) according to the procedure described in Example 3 above to give a crude product (804 mg) which was chromatographed (silica gel, 3:2 EtOAc:petroleum, increasing to 9:1 EtOAc: petroleum toward completion) to afford 55 (316 mg, 40%) as a pink wax. $^{13}C$ NMR ($CDCl_3$) δ 25.8, 29.1, 29.2, 31.4, 36.0, 36.3, 36.9, 53.1, 64.6, 70.2, 115.2, 125.8, 127.6, 128.1, 128.4, 128.5, 128.7, 130.0, 130.3, 137.1, 142.8, 157.8, 174.1. ESMS 446 $(M+H)^+$ Synthesis of (R)-(3-Phenoxy-propyl)-phosphonic acid 3-(4-benzyloxy-phenyl)-2-(7-phenyl-heptanoylamino)-propyl ester methyl ester (56a,b).

With ice-bath cooling, phosphonochloridate 53 (123 mg, 0.50 mmol) in dry THF (1.0 mL) was added dropwise to a solution of 55 (100 mg, 0.22 mmol) and $Et_3N$ (94 μL, 0.67 mmol) in dry THF (0.5 mL). After 10 min, the mixture was warmed to rt and stirred overnight. The $Et_3N.HCl$ precipitate was removed by filtration and the solvent evaporated under reduced pressure. The residue was dissolved in EtOAc, washed successively with $KHSO_4$ (5% w/v), saturated $NaHCO_3$, water, brine and dried (MgSO4). The solvent was removed in vacuo and the residue (209 mg) was purified on a C-18 reverse phase column to provide a diastereomeric mixture of 56a,b (82 mg, 56%) as an oil.

Synthesis of (R)-(3-Phenoxy-propyl)-phosphonic acid mono-[3-(4-benzyloxy-phenyl)-2-(7-phenyl-heptanoylamino)-propyl]ester (57).

A mixture of phosphonates 56a,b (34 mg, 0.052 mmol) dissolved in tert-butylamine (0.6 mL) was heated at 50° for 5 days. The mixture was then concentrated to dryness, and the residue treated with a solution of MeOH (5 mL) containing Amberlyst-15 cation exchange resin (250 mg). After 1 h stirring, the solution was decanted and the resin washed with several portions of MeOH. The combined decant and washings were then evaporated to dryness, and the residue purified on a C-18 reverse phase column to give 57 (17.8 mg, 53%) as a white solid.
$^1H$ NMR (500 MHz, $CDCl_3$) δ 1.14-1.35 (m, 4H), 1.45-1.63 (m, 4H), 1.87-2.01 (m, 2H), 2.01-2.18 (m, 4H), 2.55 (t, 2H, J=7.7 Hz), 2.77 (d, 2H, J=7.1 Hz), 3.87-4.05 (m) superimposed upon 3.97 (t, J=6 Hz); total area 4H, 4.25-4.34 (br s, 1H), 4.97 (s, 2H), 5.99-6.26 (br s, 1H), 6.86 (apparent triplet, 4H, J=8.6 Hz), 6.92 (t, 1H, J=7.3 H), 7.05-7.18 (m, 5H), 7.20-7.28 (m, 4H), 7.28-7.43 (m, 5H). $^{13}C$ NMR (125 MHz, $CDCl_3$) δ 22.5 (d, J=144.8 Hz), 22.6 (d, J=4.3 Hz), 25.5, 28.98, 29.01, 31.2, 35.9, 36.0, 36.6, 50.5 (d, J=5.0 Hz), 65.3 (d, J=6.7 Hz), 67.1 (d, J=16.8 Hz), 70.0, 114.5, 115.0, 120.9, 125.6, 127.4, 127.9, 128.2, 128.3, 128.5, 129.3, 129.5, 130.2, 137.0, 142.6, 157.7, 158.6, 173.5. ESMS 644 $(M+H)^+$

Example 8 (see Scheme 8)

3-Hydroxyphosphinoyl-propionic acid benzyl ester (58)

To HMDS (29 g, 180 mmol) was added $NH_4H_2PO_2$ (10 g, 120 mmol) and the mixture was heated to 100° under argon for 3 hours. To the cooled solution was added benzyl acrylate (3.9 g, 24 mmol) and the mixture was stirred overnight at room temperature. The mixture was quenched with hydrochloric acid (1M, 200 mL), and extracted into ethyl acetate (200 mL). The organic extract was evaporated and the residue refluxed with a mixture of HCl (1M, 2 mL) and THF (2 mL). Workup gave the phosphinic acid (0.98 g).

$^1$H NMR (CDCl3) δ 12.13(1H, bs), 7.27 (5H, m), 7.10 (1H, d, J=558 Hz), 5.05 (2H, s), 5.98 (2H, m), 1.99 (2H, m). $^{13}$C NMR (CDCl3) δ 171.8, 135.7, 128.7, 128.5, 128.4, 66.91, 26.25, 25.41, 24.23. ESMS 251 (M+Na$^+$), 229 (M+H$^+$)

3-[3-(4-Benzyoxy-phenyl)-2-tert-butoxycarbony-lamino-propoxyphosphinoyl]-propionic acid benzyl ester (59)

A mixture of (58) (580 mg, 2.5 mmol) and (54) (1.0 g, 2.8 mmol) in THF (5 mL) were treated succesively with DCC (1.05 g, 5.1 mmol) in THF (2.5 mL) and DMAP (30 mg, 0.25 mmol) in THF (2.5 mL). The mixture was stirred at room temperature for 72 hours. The mixture was filtered through Celite™, washed with a little THF, and extracted into ethyl acetate. The organic solution was w2ashed with potassium hydrogen sulfate, saturated bicarbonate solution, brine, dried and evaporated under reduced pressure. The crude product was triturated with chilled ether and filtered to yield 1.3 g, 92% of crude product that contained 5% starting alcohol by analytical HPLC. The material was used in the next step without further purification. ESMS 568 (M+H$^+$).

3-{[3-(4-Benzyloxy-phenyl)-2-tert-butoxycarbony-lamino-propoxy]-hydroxy-phosphoryl}-propionic acid benzyl ester (60)

To a stirred solution of (59) (1,3 g, 2.3 mmol) in dioxane (7 mL) was added sodium periodate (0.54 g, 2.5 mmol) and the mixture was stirred at room temperature for 16 hours. RP-HPLC (40-100% B over 10 minutes) yielded 1.3 g of an orange oil. $^1$H NMR (CDCl3) δ 7.5-7.2 (10H, m), 7.20 (2H, bd, J 8.5 Hz), 6.88 (2H, bd, J 8.5 Hz), 5.2-5.0 (2H, m), 5.11 (2H, s), 5.01 (2H, s), 4.1-3.8 (2H, m), 2.8-2.5 (4H, m), 2.2-2.0 (2H, m), 1.38 (9H, s). ESMS 584 (M+H$^+$).

(3-Hydroxy-propyl)-phosphonic acid mono-[3-(4-benzyloxy-phenyl)-2-tert-butoxycarbonylamino-propyl]ester (61)

To a stirred solution of (60) (566 mg, 0.97 mmol) in THF (10 mL) was added lithium borohydride (21.1 mg, 0.97 mmol) and the mixture was stirred at reflux for 1 hour. Additional lithium borohydride (25 mg) was added and reflux was continued for a total of 2 hours. HCl (1M) was added to the cooled mixture until -effervescence subsided and the mixture was extracted with ethyl acetate. The extract was washed with brine, dried and evaporated under reduced pressure to yield 433 mg of a viscous oil. Preparative RP-HPLC (isocratic 55% B) yielded 214.7 mg, 46% of (61) as a white solid. $^1$H NMR (300 MHz, CDCl$_3$) δ 7.41-7.27 (m, 5H), 7.09 (d, 2H), 6.88 (d, 2H), 5.25 (broad), 4.98 (s, 2H), 4.04-3.83 (m, 3H), 3.71-3.60 (m, 2H), 2.80-2.68 (m, 2H), 1.96-1.77 (m, 4H), 1.36 (s, 9H). $^{13}$C NMR (CDCl$_3$) δ 157.8, 155.9, 137.3, 130.6, 129.9, 128.7, 128.1, 127.7, 115.2, 79.9, 70.3, 65.8, 62.4 (d, J=14 Hz), 52.1, 36.7, 28.6, 25.7 (d, J$_{CP}$=4.5 Hz), 22.9 (d, J$_{CP}$=142.5 Hz). ISMS 480 (M+H$^+$)

(3-Hydroxy-propyl)-phosphonic acid mono-[3-(4-benzyloxy-phenyl)-2-(7-phenyl-heptanoylamino)-propyl]ester (62) (61)

(44.3 mg, 0.092 mmol) was treated with TFA (1 mL) at 0° for 3 minutes and the solvent was evaporated under reduced pressure. To a solution of BOP (40.9 mg, 0.092 mmol), phenylheptanoic acid (19 mg, 0.092 mmol), and DIPEA (18 μl) in DMF (1 mL) cooled to 0° was added a solution of the amine TFA salt prepared above in a mixture of DMF (0.2 mL) and DIPEA (35 μl). The mixture was stirred at room temperature overnight. The solvent was evaporated under reduced pressure and the crude residue (163 mg) was purified by Preparative RP-HPLC (isocratic 80% B) to yield pure (62) 24.8 mg, 52%. $^1$H NMR (500 MHz, CDCl$_3$) δ 7.40-7.19 (m, 7H), 7.16-7.06 (m, 5H), 6.86 (d, J=8.4 Hz, 2H), 6.42 (broad, 1H), 4.96 (s, 2H), 4.27 (m, 1H), 4.02-3.81 (m, 2H), 3.75-3.53 (m, 2H), 2.84-2.69 (m, 2H), 2.58-2.50 (m, 2H), 2.16-2.03 (m, 2H), 1.91-1.72 (m, 3H), 1.60-1.43 (m, 4H), 1.43-1.17 (m, 5H). $^{13}$C NMR (CDCl$_3$) δ 173.8, 157.6, 142.6, 137.0, 130.3, 129.5, 128.5, 128.3, 128.2, 127.9, 127.4, 125.6, 114.9, 70.0, 65.3, 62.2, 50.6, 36.6, 36.0, 35.9, 31.2, 29.0, 25.7, 25.6, 22.9 (d, J$_{CP}$=144 Hz). ISMS 568 (M+H$^+$), 1135 (2M+H$^+$).

Example 9 (See Scheme 9)

(S)-5-(4-Benzyloxy-phenyl)-4-(7-phenyl-heptanoy-lamino)-pentanoic acid (63).

(S)-5-(4-Benzyloxy-phenyl)-4-(7-phenyl-heptanoy-lamino)-pentanoic acid methyl ester (0.86 g, 1.7 mmol) and NaOH solution (4 M, 0.85 mL, 3.4 mmol) in MeOH-THF (1:1, 6 mL) was stirred at room temperature overnight. The solvent was removed, and the residue diluted with water. The solution was washed with Et$_2$O, acidified with 5% aqueous HCl, and extracted with EtOAc. The organic phase was then washed with brine, dried Na$_2$SO$_4$) and the solvent removed under reduced pressure to afford (63), 0.81 g (98%), m.p. 127.7-129.5° C. $^1$H NMR (DMSO-d$_6$) δ 1.13-1.23 (6H, m, 3×CH$_2$), 1.35-1.44 (2H, m, CH$_2$), 1.47-1.54 (2H, m, CH$_2$), 1.95-2.00 (2H, m, CH$_2$), 2.14-2.22 (2H, m, CH$_2$), 3.86 (1H, br s, H$_{58}$☐ 5.02 (2H, s, OCH$_2$Ph), 6.89 (2H, d, J=8.6 Hz), 7.08 (2H, d, J=8.5 Hz), 7.15-7.44 (10H, m, 10×Ar—H), 7.50 (1H, br d, J=8.6 Hz, NH), 12.01 (1H, br s, CO$_2$H). $^{13}$C NMR (DMSO-d$_6$) δ 25.3, 28.4, 28.5, 29.3, 30.5, 31.0, 35.2, 35.5, 49.3, 114.3, 125.6, 127.7, 127.8, 128.2, 128.4, 130.1, 131.1, 137.2, 142.3, 156.7, 171.7, 174.3.

(S)-7-Phenyl-heptanoic acid [1-(4-benzyloxy-benzyl)-3-carbamoyl-propyl]-amide (64).

DIPEA (0.12 mL, 0.68 mmol) was added dropwise to a stirred solution of (63) (300 mg, 0.62 mmol) and BOP (300 mg, 0.68 mmol) in DMF (4 mL). After 10 min, NH$_3$ solution (25%, 0.75 mL) was added, and the mixture stirred for 1 h. The solvent was removed under reduced pressure, and the crude residue diluted with water and extracted into warm EtOAc. The combined extracts were then washed with HCl solution (1 M), water, saturated NaHCO$_3$ solution, brine and dried over MgSO$_4$. Evaporation of the solvent in vacuo gave (64) (300 mg, quantitative) as a white powder, ESMS 487 (M+H)$^+$.

(S)-7-Phenyl-heptanoic acid [1-(4-benzyloxy-benzyl)-3-cyano-propyl]-amide (65)

To a stirred solution of (64) (171 mg, 0.35 mmol) in pyridine (9 mL) was added phosphoryl chloride (65 μl) at 0° under argon. After 10 minutes the mixture was brought to room temperature and stirring was continued for 1.5 hours. The solvent was evaporated under reduced pressure and the residue was dissolved in ethyl acetate (10 mL), dried, filtered and evaporated under reduced pressure to yield the crude product (101 mg) which was used without further purification.

(S)-7-Phenyl-heptanoic acid [1-(4-benzyloxy-benzyl)-3-(1H-tetrazol-5-yl)-propyl]-amide (66).

A mixture of (65) (74 mg, 0.16 mmol), NaN₃ (103 mg, 1.58 mmol) and Et₂NH.HCl (173 mg, 1.58 mmol) in toluene (1.5 mL) was heated at reflux for 48 h. The organic phase was decanted, and the remaining gum washed several times with $CH_2Cl_2$. The washings were filtered (Celite™), and the organic phases combined. Evaporation of the solvent under reduced pressure afforded a brown gum (180 mg) which was chromatographed on a C-18 reverse phase column to provide (66) (29 mg, 36%). $^1$H NMR (500 MHz, $d_4$-MeOH) δ 7.43-7.07 (m, 12H), 6.9 (d, 2H, J=8.6 Hz), 4.99 (s, 2H), 4.15-4.04 (m, 1H), 3.03-2.86 (m, 2H), 2.79 (dd, 1H, J=5.7, 13 Hz), 2.65 (dd, 1H, J=8.7, 13 Hz), 2.54 (t, 2H, J=7.6 Hz), 2.12-2.00 (m, 3H), 1.90-1.78 (m, 1H), 1.50-1.36 (m, 2H), 1.33-1.10 (m, 4H). $^{13}$C NMR (125 MHz, $d_4$-MeOH) δ 176.2, 158.9, 156.2, 143.9, 138.8, 131.9, 131.3, 129.5, 129.4, 129.3, 128.8, 128.5, 126.6, 115.8, 71.0, 51.5, 41.1, 37.2, 36.8, 33.5, 32.5, 30.0 (two superimposed), 27.0, 21.3. ESMS 512 (M+H)⁺.

Example 10 (See Scheme 10)

(S)-5-(4-Benzyloxy-phenyl)-4-(7-phenyl-heptanoylamino)-pentanoic acid methyl ester (67)

Compound 40 (3.0 g, 0.0073 mol) was added to TFA (10 ml) at 0° C. with stirring. After 10 min, ice was added, and the mixture extracted into EtOAc. The extracts were washed with $K_2CO_3$ solution (20% w/v) and brine, dried with MgSO₄, and evaporated to afford 2.23 g (98%) of the amine free base. The material was used immediately without futher purification. DIPEA (2.03 g, 2.74 ml, 0.0158 mol) was added in one portion to a stirred solution of 7-phenylhept-6-ene-oic acid (1:1 mixture of E- and Z-isomers, 1.6 g, 0.0079 mol) and BOP (3.48 g, 0.0079 mol) in dry DMF (5 ml). After 5 min, a solution of the amine free base (2.23 g, 0.00716 mol) in dry DMF (10 ml) was added, and the mixture stirred overnight. Water (50 ml) was added, and the mixture extracted with EtOAc. The extract was then washed with water, HCl (1M), saturated NaHCO₃, and dried with MgSO₄. The solution was then filtered, and the crude product hydrogenated (10% Pd/C). The catalyst was removed by filtration through Celite™, and the solvent evaporated to yield a residue which was chromatographed (silica gel, 3:2 Et₂O/petroleum ether) to afford 67 (1.98 g, 55%), mp 94.8-95.9° C. $^1$H NMR (CDCl₃) δ 1.31 (4H, m), 1.59 (5H, m), 1.84 (1H, m), 2.07 (2H, t, J=7 Hz), 2.33 (2H, m), 2.58 (2H, t, J=8 Hz), 2.68 (1H, dd, J=8, 15 Hz), 2.76 (1H, dd, J=8, 15 Hz), 3.63 (3H, s), 4.14 (1H, m), 5.01 (2H, s), 5.38 (1H, d, J=9Hz), 6.88 (2H, d, J=8Hz), 7.07 (2H, d, J=10 Hz), 7.11-7.48 (10H, m). $^{13}$C NMR (CDCl₃) δ 25.8, 29.0, 29.1, 29.2, 31.1, 31.4, 36.0, 37.0, 40.6, 50.2, 51.9, 70.1, 114.9, 125.8, 127.6, 128.0, 128.4, 128.5, 128.7, 130.0, 130.5, 137.2, 142.8, 157.7, 172.9, 174.4 ppm. ESMS 502 (M+H)⁺.

(S-5-(4-Benzyloxy-phenyl)-4-(7-phenyl-heptanoylamino)-pentanoic acid (68)

A mixture of 67 (0.86 g, 1.7 mmol) and NaOH (4M, 0.85 ml, 3.4 mmol) were stirred in MeOH-THF (1:1, 6 ml) at room temperature overnight. The solvents were evaporated and the residue was diluted with water. This was washed with Et₂O, acidified with 5% aqueous HCl, then extracted into Et₂O. The extract was washed with brine then dried (Na₂SO₄) and evaporated to a white solid (0.81 g, 98%). $^1$H NMR (DMSO-$d_6$) δ 1.13-1.23 (6H, m, 3×CH₂), 1.35-1.44 (2H, m, CH₂), 1.47-1.54 (2H, m, CH₂), 1.95-2.00 (2H, m, CH₂), 2.14-2.22 (2H, m, CH₂), 3.86 (1H, br s, H$_\alpha$) 5.02 (2H, s, OCH₂Ph), 6.89 (2H, d, J=8.6 Hz), 7.08 (2H, d, J=8.5 Hz), 7.15-7.44 (10H, m, 10×Ar—H), 7.50 (1H, br d, J=8.6 Hz, NH), 12.01 (1H, br s, CO₂H). $^{13}$C NMR (DMSO-$d_6$) δ 25.3, 28.4, 28.5, 29.3, 30.5, 31.0, 35.2, 35.5, 49.3, 114.3, 125.6, 127.7, 127.8, 128.2, 128.4, 130.1, 131.1, 137.2, 142.3, 156.7, 171.7, 174.3. ESMS 488 (M+H)⁺.

Example 11

(RS)-5-(4-Benzyloxy-phenyl)-4-tertbutoxycarbonylamino-pent-2-enoic acid ethyl ester (77) and (RS)-5-(4-Benzyloxy-phenyl)-4-tertbutoxycarbonylamino-pent-2-enoic acid methyl ester (RS-40)

DIPEA (28.2 ml, 20.9 g, 162 mmol) was added to a stirred solution of (RS)-3-(4-benzyloxy-phenyl)-2-tert-butoxycarbonylamino-propionic acid (20.0 g, 53.9 mmol), BOP (25.00 g, 56.5 mmol) and MeONHMe.HCl (5.52 g, 56.6 mmol) in DMF (300 mL). After stirring 2 hr, the DMF was evaporated and the residue was dissolved in EtOAc and washed with water, 5% aq. HCl, saturated aq. NaHCO₃ and brine, then dried with Na₂SO₄ and evaporated to afford (RS)-[2-(4-Benzyloxy-phenyl)-1-(methoxy-methyl-carbamoyl)-ethyl]-carbamic acid tert-butyl ester (22.39 g, 100%), mp 107.1-108.7° C. $^1$H NMR (CDCl₃) δ 0.40 (s, 9H), 2.83 (dd, J=6.2, 14.2 Hz, 1H), 3.00 (dd, J=6.1, 13.6 Hz, 1H), 3.17 (s, 3H), 3.65 (s, 3H), 4.91 (br s, 1H), 5.04 (s, 2H), 5.15 (br d, J=7.1 Hz, 1H), 6.90 (d, J=8.6 Hz, 2H), 7.09 (d, J=8.5 Hz, 2H), 7.32-7.44 (m, 5H). $^{13}$C NMR (CDCl₃) δ 172.3, 157.7, 155.2, 137.1, 130.4, 128.9, 128.5, 127.9, 127.4, 114.7, 79.6, 70.0, 61.5, 51.6, 38.0, 32.1, 28.3.

LiAlH₄ (916 mg, 24.1 mmol) was added cautiously and portionwise during 15 min to a stirred solution of (RS)-[2-(4-Benzyloxy-phenyl)-1-(methoxy-methyl-carbamoyl)-ethyl]-carbamic acid tert-butyl ester (10.00 g, 24.1 mmol) in THF (150 mL) at 0° C. under an atmosphere of argon. The ice-bath was removed and the mixture was stirred for 1 hr, then poured onto a mixture of ice and KHSO₄ (1 M aq.). When the ice had melted the product was extracted into EtOAc. The combined extracts were washed with brine then dried (Na₂SO₄) and evaporated to give (RS)-[1-(4-Benzyloxy-benzyl)-2-oxo-ethyl]-carbamic acid tert-butyl ester (8.51 g, 99%), mp 100.3-101.7° C. $^1$H NMR (CDCl₃) δ 1.44 (s, 9H), 3.07 (d, J=6.7 Hz, 2H), 4.40 (br s, 1H), 5.05 (s, 2H), 6.92 (d, J=8.6 Hz, 2H), 7.09 (d, J=8.7 Hz, 2H), 7.33-7.45 (m, 5H), 9.63 (s, 1H). $^{13}$C NMR (CDCl₃) δ 199.6, 156.4, 144.4, 136.8, 130.4, 128.6, 128.5, 128.0, 127.9, 127.5, 115.1, 80.9, 70.0, 46.0, 34.6, 28.3.

A solution of triethyl phosphonoacetate or methyl diethylphosphonoacetate (5.19 mmol) and (RS)-[1-(4-Benzyloxy-benzyl)-2-oxo-ethyl]-carbamic acid tert-butyl ester (1.843 g, 5.19 mmol) in DCM (5 mL) was added dropwise to a vigorously stirred mixture of 50% aq. NaOH (30 mL) and 50 mL DCM containing tetrabutylammonium iodide (1.0 g). After 3 hr, the layers were separated and the organic phase was washed with water (20 mL) and brine (10 mL) then dried (Na₂SO₄) and evaporated. The crude material was chromatographed (silica gel, 1:4 EtOAc/petroleum) to give either (RS)-5-(4-Benzyloxy-phenyl)-4-tertbutoxycarbonylamino-pent-2-enoic acid ethyl ester 77 or (RS)-5-(4-Benzyloxy-phenyl)-4-tertbutoxycarbonylamino-pent-2-enoic acid methyl ester RS-40 (~85% yield in each case). Compound 77: $^1$H nmr (CDCl$_3$) δ 1.28 (t, J=7.1 Hz, 3H), 1.40 (s, 9H), 2.84 (br d, J=6.2 Hz, 2H), 4.19 (q, J=7.1 Hz, 2H), 4.52 (br s, 2H), 5.05 (s, 2H), 5.86 (dd, J=1.5, 15.7 Hz, 1H), 6.91 (dd, J=4.8, 15.6 Hz, 1H), 6.92 (d, J=8.6 Hz, 2H), 7.09 (d J=8.7 Hz, 2H), 7.32-7.45 (m, 5H). $^{13}$C nmr (CDCl$_3$) δ 66.1, 157.7, 154.9, 147.7, 137.0, 130.4, 128.6, 127.9, 127.4, 121.0, 115.1, 114.9, 79.8, 70.0, 60.4, 52.4, 40.0, 28.3, 14.2. Compound RS-40: $^1$H NMR (CDCl$_3$) δ 1.40 (s, 9H), 2.80 (m, 2H), 3.70 (s, 3H), 4.52 (br s, 2H), 5.05 (s, 2H), 5.83 (d, J=15 Hz, 1H), 6.88 (d, J=8.7 Hz, 2H), 6.88 (d, J=15 Hz, 1H), 7.07 (d, J=8.7 Hz, 2H), 7.28-7.48 (m, 5H). $^{13}$C NMR (CDCl$_3$) δ 28.5, 40.1, 51.8, 52.6, 70.2, 80.0, 115.1, 120.8, 127.6, 128.1, 128.7, 130.6, 137.1, 148.2, 155.1, 157.9, 166.8.

Example 12

General Procedure A

BOP mediated coupling of pyridyl- or phenyl-alkanoic acids to 77 and (RS)41. Unless otherwise detailed below, arylalkanoic acids were prepared by minor modifications to the example detailed for 7-phenylheptanoic acid (51) above (Example 5)

7-(2-Methoxy-phenyl)-heptanoic acid (71d)

Prepared from 2-methoxybenzaldehyde and carboxyhexyl)triphenylphosphonium bromide. $^1$H NMR (CDCl$_3$) δ 1.42 (m, 4H), 1.70 (m, 4H), 2.41 (t, J=8 Hz, 2H), 2.64 (t, J=8 Hz, 2H), 3.84 (s, 3H), 6.80 (m, 3H), 7.24 (m, 1H). $^{13}$C NMR (CDCl$_3$) δ 24.7, 29.0 (2 peaks superimposed), 180.6, 159.7, 144.4, 129.3, 121.0, 114.3, 111.0, 55.2, 36.0, 34.2, 31.3.

7-(3-Acetylamino-phenyl)-heptanoic acid (71e)

A solution of m-nitrobenzaldehyde 69d (20 g, 0.13 mol), ethylene glycol (9.0 g, 0.15 mol) and p-TsOH (catalytic amount) in toluene (50 mL) was refluxed under a Dean-Stark trap for 12 hr. The solution was then cooled to room temperature, diluted with toluene (20 mL) and washed with NaOH solution (1 M, 20 mL), water, brine and then dried with MgSO$_4$. Evaporation of the solvent under reduced pressure gave 2-(3-Nitro-phenyl)-[1,3]dioxolane (24 g, 95%): $^1$H NMR (CDCl$_3$) δ 4.11 (d of mult, ethylenedioxy, 4H), 5.78 (s, 1H), 7.56 (t, J=8 Hz, 1H), 7.80 (d of mult, J=8 Hz), 8.22 (d of mult., 1H), 8.35 (m, 1H). $^{13}$C NMR (CDCl$_3$) δ 148.3, 140.5, 132.8, 129.5, 124.1, 121.7, 102.3, 65.6.

2-(3-Nitro-phenyl)-[1,3]dioxolane (17.8 g) was hydrogenated over 10% Pd—C (830 mg) in EtOAc (125 mL). Removal of the catalyst (Celite) and evaporation of the solvent in vacuo afforded 3-[1,3]dioxolan-2-yl-phenylalanine as a yellow oil (quantitative yield). $^1$H NMR (CDCl$_3$) δ 4.06 (d of mult., ethylenedioxy, 4H), 5.73 (s, 1H), 6.66 (m, 1H), 6.80 (m, 1H), 6.86 (m, 1H), 7.16 (t, J=8 Hz). $^{13}$C NMR (CDCl$_3$) δ 146.7, 139.1, 129.5, 116.7, 116.0, 112.9, 103.8, 65.3.

A solution of acetyl chloride (3.75 g, 0.048 mol, 3.4 mL) in CH$_2$Cl$_2$ (6.5 mL) was added dropwise over 15 min to an ice-bath chilled solution of 3-[1,3]dioxolan-2-yl-phenylamine (7.18 g, 0.043 mol) and pyridine (3.40 g, 0.043 mol, 3.5 mL) in CH$_2$Cl$_2$ (85 mL). The solution was then brought to room temperature, stirred for 1 hr, and poured onto ice-water (60 mL). The phases were separated, and the organic layer washed with water, saturated NaHCO$_3$, brine and dried with MgSO$_4$. Removal of the solvent in vacuo afforded N-(3-[1,3]dioxolan-2-yl-phenyl)-acetamide (8.01 g, 90%). $^1$H NMR (CDCl$_3$) δ 2.08 (s, 3H), 4.03 (d of mult., ethylenedioxy), 5.71 (s, 1H), 7.17 (d, J=8 Hz, 1H), 7.26 (t, J=8 Hz, 1H), 7.53 (d, J=8 Hz, 1H), 7.62 (s, 1H), 8.32 (br s, 1H). $^{13}$C NMR (CDCl$_3$) δ 168.9, 138.8, 138.3, 129.1, 122.3, 120.8, 118.1, 103.5, 65.4, 24.4.

A mixture of N-(3-[1,3]Dioxolan-2-yl-phenyl)-acetamide (7.8 g, 0.037 mol) and pyridinium-p-toluenesulfonate (2.8 g, 0.011 mol) in acetone-water (4:1, 400 mL) was refluxed for 1 hr. The solution was then cooled to room temperature, and the bulk of the solvent (~90%) removed under reduced pressure. The remaining solution was then extracted with EtOAc, and the combined extracts washed with saturated NaHCO$_3$, brine, and dried with MgSO$_4$. Evaporation of the solvent gave N-(3-Formyl-phenyl)-acetamide (5.98 g, 98%) as an orange oil. $^1$H NMR (CDCl$_3$) δ 2.22 (s, 3H), 7.46 (t, J=8 Hz, 1H), 7.59 (d, J=8 Hz, 1H), 7.89 (d, J=8 Hz, 1H), 8.07 (s, 1H), 8.69 (br s, 1H), 9.94 (s, 1H). $^{13}$C NMR (CDCl$_3$) δ 193.9, 171.0, 140.8, 138.5, 131.2, 127.5, 127.1, 122.0, 26.0.

Prepared from N-(3-Formyl-phenyl)-acetamide (5.93 g, 36.3 mmol) and (6-carboxyhexyl)triphenylphosphonium bromide (17.45 g, 38.2 mmol) to give 7.98 g crude product, which, after esterification with MeOH/H$_2$SO$_4$ and chromatography (silica gel, 4:1 EtOAc:petroleum), afforded the corresponding methyl ester (2.86 g, 29%). Subsequent hydrogenation and hydrolysis of the purified methyl ester gave the title compound 71e (2.36 g, 86% yield from two steps) as an orange solid: $^1$H NMR (Acetone-d6) δ 1.36 (m, 4H), 1.62 (m, 4H), 2.06 (s, 3H), 2.28 (t, J=7 Hz, 2H), 2.57 (t, J=7 Hz, 2H), 6.88 (d, J=8 Hz, 1H), 7.17 (t, J=8 Hz, 1H), 7.46 (d, 1H) overlapped with 7.48 (s, 1H), 9.08 (br s, 1H). $^{13}$C NMR (Acetone-d6) δ 174.8, 168.9, 144.1, 140.5, 129.4, 124.2, 120.0, 117.4, 36.0, 34.2, 32.1, 25.6, 24.4 (two signals obscured).

7-(3-Amino-phenyl)-heptanoic acid (72)

m-nitro benzaldehyde (5.0 g, 33.1 mmol) in dry THF (20 mL) was added in one portion to a stirred suspension of NaH (60% dispersion, 2.92 g, 73.0 mmol) and (6-carboxyhexyl)-triphenylphosphonium bromide (15.9 g, 34.8 mmol) in dry THF (60 mL). After 24 hr, the resultant precipitated mass was dissolved in NaOH solution (1M, 100 mL) and washed with EtOAc. The alkaline solution was then acidified with conc. HCl, extracted with EtOAc, and the extracts washed with brine and dried with MgSO$_4$. Removal of the solvent in vacuo afforded a crude residue (10.6 g). To facilitate chromatographic purification, the crude material was esterified with EtOH/H$_2$SO$_4$, and then chromatographed (silica gel, 30:70 EtOAc-petroleum) to afford the corresponding ethyl ester of (5.14 g, 56%) as a mixture of E- and Z-isomers (ca. 1:1). Re-hydrolysis of this material (4.93 g, 17.8 mmol) according to general procedure B gave (4.4 g, quantitative). This material was hydrogenated over Pd—C (10%, 220 mg) in EtOAc (225 mL), and the crude product taken into Et$_2$O and neutralised with conc. HCl (~1.8 mL) to afford a tan precipitate. The precipitated solid was filtered, washed with acetone followed by ether, and collected to provide the hydrochloride salt 72 (4.43 g, 97%): $^1$H NMR (CDCl$_3$) δ 1.37 (mn, 4H), 1.65 (m, 4H), 2.35 (t, J=8 Hz, 2H), 2.52 (t, J=8 Hz), 6.53 (m, 2H), 6.60 (d of mult, 1H), 7.07 (m, 1H). $^{13}$C NMR (CDCl$_3$) δ 179.9, 146.1, 144.1, 129.3, 119.3, 115.7, 113.0, 36.0, 34.2, 31.2, 29.0 24.8. ESMS 222 (M+H)$^+$.

7-(3-Nitro-phenyl)-heptanoic acid (73)

Acetone (14 mL) in water (17 mL) was added with simultaneous addition of a separate solution of Oxone (5.96 g, 9.7 mmol) dissolved in EDTA solution (0.0004 M, 35 mL) to a solution of 72 (500 mg, 1.9 mmol), NaOH (170 mg, 4.2 mmol) and $NaHCO_3$ (1.63 g, 19 mmol) in water (30 mL) at 0-2° C. The Oxone solution was added at twice the rate of the acetone solution, and care was taken to ensure that the internal temperature was kept below 8°. After stirring overnight, $Na_2S_2O_5$ solution was added (10% w/v, 50 mL) and the mixture extracted with EtOAc. The extract was washed with brine, dried over $MgSO_4$ and the solvent removed in vacuo. Chromatography of the crude material (silica gel, 2:3 EtOAc:petroleum) afforded 73 (149 mg, 31%): $^1$H NMR ($CDCl_3$) δ 1.36 (mn, 4H), 1.63 (m, 4H), 2.33 (t, J=7 Hz, 2H), 2.69 (t, J=8 Hz, 2H), 7.44 (m, 2H), 8.02 (m, 2H). $^{13}$C NMR ($CDCl_3$) δ 180.2, 148.5, 144.7, 134.9, 129.3, 123.3, 121.1, 35.6, 34.1, 31.0, 28.93, 28.88, 24.7.

(E)-7-Pyridin-3-yl-hept-6-enoic acid (76)

(Ethyl-6-carboxyhexyl)triphenylphosphonium bromide (156 g, 0.32 mol) in dry THF (350 mL) was added dropwise to a suspension of NaH (60% dispersion, 12 g, 0.30 mol) in dry THF (350 mL). Additional THF (200 mL) was added, and the mixture stirred for 2.5 hr. 3-pyridinecarboxaldehyde (30.8 g, 27.1 ml, 0.29 mol, Aldrich) in dry THF (60 mL) was added dropwise, and the solution stirred overnight. The resultant blood-red suspension was filtered (Celite) and the filtrate poured onto water (1 L) and extracted with $Et_2O$. The extract was washed with water, brine, dried with $MgSO_4$, and most of the solvent (~90%) removed in vacuo. The remaining residue was chilled overnight (freezer) and the precipitated solids removed by filtration. The filter cake was rinsed with a small volume of chilled $Et_2O$, and the combined filtrates evaporated to provide a crude product (62 g). Distillation of the crude product gave 75 (33.2 g, 49%) as a yellow oil, (b.p.$_{0.2}$ 134-138° C.). ESMS 234 (M+H)$^+$.

Compound 75 (5.0 g, 21 mmol) was hydrolysed according to general procedure B to afford the title compound 76 (3.56 g, 83%): $^1$H NMR ($CDCl_3$) δ 1.56 (m, 2H), 1.71 (m, 2H), 2.35 (m, 4H), 5.85 (dt, 1H, J=7, 12 Hz), 6.38 (m, 1H), 7.34 (m, 1H), 7.66 (m, 1H), 8.48 (m, 1H), 8.57 (s, 1H), 11.42 (br s, 1H). $^{13}$C NMR ($CDCl_3$) δ 177.4, 148.4, 146.1, 136.9, 135.7, 133.9, 125.1, 123.6, 34.3, 29.2, 28.4, 24.6.

Synthesis of (RS)-5-(4-Benzyloxy-phenyl)-4-(7-phenyl-heptanoylamino)-pentanoic acid methyl ester (compound 78)

(RS)-5-(4-Benzyloxy-phenyl)-4-tertbutoxycarbonylamino-pent-2-enoic acid methyl ester (RS)-40 (3.0 g, 0.0073 mol) was added to TFA (10 mL) at 0° C. with stirring. After 10 min, ice was added, and the mixture extracted into EtOAc. The extracts were washed with $K_2CO_3$ solution (20% w/v) and brine, dried with $MgSO_4$, and evaporated to afford 2.23 g (98%) of crude product (RS)-41. The crude material was dissolved in dry DMF (10 mL) and added dropwise to a solution of DIPEA (2.03 g, 2.74 mL, 0.0158 mol), 7-phenylhept-6-ene-oic acid 70b (1:1 mixture of E- and Z-isomers, 1.6 g, 0.0079 mol) and BOP (3.48 g, 0.0079 mol) in dry DMF (5 mL). After stirring overnight, the mixture was diluted with water (50 mL) and extracted with EtOAc. The organic phase was then washed with water, HCl (1 M), saturated $NaHCO_3$, and dried with $MgSO_4$. The solution was then filtered, and the crude mixture hydrogenated (10% Pd/C). The catalyst was removed by filtration through celite, and the solvent evaporated. The crude material was chromatographed (silica gel, 3:2 $Et_2O$/petroleum ether) to afford 78 (1.98 g, 55%), mp 94.8-95.9° C. $^1$H NMR ($CDCl_3$) δ 1.31 (4H, m), 1.59 (5H, m), 1.84 (1H, m), 2.07 (2H, t, J=7 Hz), 2.33 (2H, m), 2.58 (2H, t, J=8 Hz), 2.68 (1H, dd, J=8, 15 Hz), 2.76 (1H, dd, J=8, 15 Hz), 3.63 (3H, s), 4.14 (1H, m), 5.01 (2H, s), 5.38 (1H, d, J=9 Hz), 6.88 (2H, d, J=8 Hz), 7.07 (2H, d, J=10 Hz), 7.11-7.48 (10H, m). $^{13}$C NMR ($CDCl_3$) δ 174.4, 172.9, 157.7, 142.8, 137.2, 130.5, 130.0, 128.7, 128.5, 128.4, 128.0, 127.6, 125.8, 114.9, 70.1, 51.9, 50.2, 40.6, 37.0, 36.0, 31.4, 31.1, 29.2, 29.1, 29.0, 25.8. ESMS 502 (M+H)$^+$.

Also obtained in this fashion are compounds 7-84.

(RS)-5-(4-Benzyloxy-phenyl)-4-(6-phenyl-hexanoylamino)-pentanoic acid ethyl ester (79)

From 6-phenylhexanoic acid 71a and (RS)-5-(4-Benzyloxy-phenyl)-4-tertbutoxycarbonylamino-pent-2-enoic acid ethyl ester 77 (83% yield): $^1$H nmr ($CDCl_3$) δ 1.26 (t, J=7.2 Hz, 3H), 1.28-1.90 (m, 9H), 2.11 (t, J=7.4 Hz, 2H), 2.29-2.38 (m, 2H), 2.60 (t, J=7.6 Hz, 2H), 2.71-2.77 (m, 2H), 4.12 (q, J=7.1 Hz, 2H), 5.03 (s, 2H), 5.55 (br d, J=8.7 Hz, 1H), 6.91 (d, J=8.6 Hz, 2H), 7.10 (d, J=8.6 Hz, 2H), 7.16-7.44 (m, 10H). $^{13}$C nmr ($CDCl_3$) δ 173.8, 172.8, 157.5, 142.4, 136.9, 130.3, 129.9, 128.5, 128.3, 128.2, 127.8, 127.4, 125.6, 114.7, 69.9, 60.5, 50.1, 40.3, 36.7, 35.6, 31.1, 31.0, 28.7, 28.6, 25.5, 14.1.

(RS)-5-(4-Benzyloxy-phenyl)-4-(8-phenyl-octanoylamino)-pentanoic acid ethyl ester (80)

From 8-phenyloctanoic acid 71c and (RS)-5-(4-Benzyloxy-phenyl)-4-tertbutoxycarbonylamino-pent-2-enoic acid ethyl ester 77 (96% yield): $^1$H nmr ($CDCl_3$) δ 1.20 (t, J=7.1 Hz, 3H), 1.27-1.55 (m, 10H), 2.06 (t, J=7.4 Hz, 2H), 2.52 (t, J=7.4 Hz, 2H), 2.74-2.79 (m, 2H), 4.10 (q, J=7.0 Hz, 2H), 4.84-4.88 (m, 1H), (4.94, s, 2H), 5.80 (br d, J=15.8 Hz, 1H), 6.00 (d J=8.2 Hz, 1H), 6.82-7.36 (m, 15H). $^{13}$C nmr ($CDCl_3$) δ 172.5, 165.9, 157.5, 147.2, 142.5, 136.7, 130.1, 128.6, 128.3, 128.1, 128.0, 127.7, 127.2, 121.0, 114.7, 69.7, 60.2, 50.6, 39.3, 36.3, 35.7, 31.2, 29.0, 28.9, 28.1, 25.4, 14.0.

(RS)-5-(4-Benzyloxy-phenyl)-4-[7-(2-methoxy-phenyl)-heptanoylamino]-pentanoic acid methyl ester (81)

Isolated as a white solid from 7-(2-Methoxy-phenyl)-heptanoic acid 70d and (RS)-5-(4-Benzyloxy-phenyl)-4-tertbutoxycarbonylamino-pent-2-enoic acid methyl ester RS-40 (65% yield): chromatographed on silica gel using 30:70 EtOAc:petroleum; $^1$H NMR ($CDCl_3$) δ 1.30 (m, 4H), 1.60 (m, 5H), 1.84 (m, 1H), 2.07 (t, J=8 Hz, 2H), 2.28, (dd, J=12 and 7 Hz, 1H), 2.38 (dd, J=12 and 7 Hz, 1H), 2.57 (dd, J=8 Hz, 2H), 2.67 (dd, J=15 and 7 Hz, 1H), 2.75 (dd, J=15 and 7 Hz, 1H), 3.62 (s, 3H), 3.78 (s, 3H), 4.11 (m, 1H), 4.99 (s, 2H), 5.28 (d, J=9 Hz, 1H), 6.82 (t, J=7 Hz, 1H); 6.87 (d, J=7 Hz, 2H), 7.06 (d, J=9 Hz, 2H), 7.11 (m, 1H), 7.36 (m, 3H).

(RS)-4-[7-(3-Acetylamino-phenyl)-heptanoylamino]-5-(4-benzyloxy-phenyl)-pentanoic acid methyl ester (82)

Obtained from 7-(3-Acetylamino-phenyl)-heptanoic acid 71e and (RS)-5-(4-Benzyloxy-phenyl)-4-tertbutoxycarbonylamino-pent-2-enoic acid methyl ester RS-40 (33% yield): chromatographed on silica gel using 35:75 acetone:petroleum; $^1$H NMR (CDCl$_3$) δ 1.25 (m, 4H), 1.55 (m, 5H), 1.83 (m, 1H), 2.07 (t, J=7.5 Hz, 2H), 2.13, (s, 3H), 2.33 (m, 2H), 2.55 (t, J=7.4 Hz, 2H), 2.68 (dd, J=15 and 7 Hz, 1H) and 2.75 (dd, J=15 and 7 Hz, 1H), 3.63 (s, 3H), 4.13 (m, 1H), 5.00 (s, 2H), 5.56 (d, J=9 Hz, 1H), 6.88 (m, 3H); 7.06 (d, J=9 Hz, 2H), 7.19 (t, J=8 Hz, 1H), 7.34 (m, 7H), 7.64 (br s, 1H). ESMS 559 (M+H)$^+$.

(RS) 5-(4-Benzyloxy-phenyl)-4-[7-(3-nitro-phenyl)-heptanoylamino]-pentanoic acid methyl ester (83)

Isolated as a pale yellow solid from 7-(3-Nitro-phenyl)-heptanoic acid and 73 and (RS)-5-(4-Benzyloxy-phenyl)-4-tert-butoxycarbonylamino-pentanoic acid methyl ester RS-40 (55% yield): chromatographed on silica gel using 0.5% MeOH in CH$_2$Cl$_2$; $^1$H NMR (CDCl$_3$) δ 1.30 (m, 4H), 1.63 (m, 5H), 1.85 (m, 1H), 2.07 (t, J=8 Hz), 2.32 (m, 2H), 2.67 (t, J=8 Hz, 2H) superimposed upon 2.71 (m, 2H), 3.62 (s, 3H), 4.13 (m, 1H), 5.00 (s, 3H), 5.31 (broadened d, J=9 Hz, 1H), 6.87 (d, J=9 Hz), 7.05 (d, J=9 Hz), 7.35 (m, 6H), 7.46 (m, 1H), 8.0 (m, 2H). ESMS 547 (M+H)$^+$.

(RS)-5-(4-Benzyloxy-phenyl)-4-(7-pyridin-3-yl-heptanoylamino)-pentanoic acid methyl ester (84)

Isolated as a gum from (E)-7-Pyridin-3-yl-hept-6-enoic acid 76 (137 mg, 0.67 mmol) and (RS)-5-(4-Benzyloxy-phenyl)-4-tertbutoxycarbonylamino-pent-2-enoic acid methyl ester RS-40 (250 mg, 0.61 mmol) to afford the title compound (79.4 mg, 26%) as a gum: chromatographed on silica using 70:30 EtOAc:petroleum. $^1$H nmr (CDCl$_3$) δ 1.30 (m, 4H), 1.49-1.82 (m, 5H), 1.82-1.95 (m, 1H), 2.08 (t, J=8 Hz, 2H), 2.34 (m, 2H), 2.59 (t, J=8 Hz), 2.69 (dd, J=7, 14 Hz, 1H), 2.77 (dd, J=7, 14 Hz, 1H), 3.65 (s, 3H), 4.15 (m, 1H), 5.03 (s, 2H), 5.36 (br d, J=9 Hz, 1H), 6.90 (d, J=9 Hz, 2H), 7.9 (d, J=9 Hz, 2H), 7.17-7.52 (m, 7H), 8.42 (br s, 2H). ESMS 503 (M+H)$^+$.

Example 13

General Procedure B; Hydrolysis of Esters

Synthesis of (RS)-5-(4-Benzyloxy-phenyl)-4-(7-phenyl-heptanoylamino)-pentanoic acid (85)

A mixture of (RS)-5-(4-Benzyloxy-phenyl)-4-(7-phenyl-heptanoylamino)-pentanoic acid methyl ester 78 (0.86 g, 1.7 mmol) and NaOH solution (4 M, 0.85 mL, 3.4 mmol) in MeOH-THF (1:1, 6 mL) was stirred at room temperature overnight. The solvent was removed, and the residue diluted with water. The solution was washed with Et$_2$O, acidified with 5% aqueous HCl, and extracted with EtOAc. The organic phase was then washed with brine, dried (Na$_2$SO$_4$) and the solvent removed under reduced pressure to afford 85 (0.81 g, 98%), m.p. 127.7-129.5° C. $^1$H NMR (DMSO-d$_6$) δ 1.13-1.23 (m, 6H), 1.35-1.44 (m, 2H), 1.47-1.54 (m, 2H), 1.95-2.00 (m, 2H), 2.14-2.22 (m, 2H), 3.86 (br s, 1H), 5.02 (s, 2H), 6.89 (d, J=8.6 Hz, 2H), 7.08 (d, J=8.5 Hz, 2H), 7.15-7.44 (m, 10H), 7.50 (br d, J=8.6 Hz, 1H), 12.01 (br s, 1H). $^{13}$C NM (DMSO-d$_6$) δ 174.3, 171.7, 156.7, 142.3, 137.2, 131.1, 130.1, 128.4, 128.2, 127.8, 127.7, 125.6, 114.3, 49.3, 35.5, 35.2, 31.0, 30.5, 29.3, 28.7, 28.4, 25.3. ESMS 488 (M+H)$^+$.

Also obtained in this fashion are compounds 86-91.

(RS)-5-(4-Benzyloxy-phenyl)-4-(6-phenyl-hexanoylamino)-pentanoic acid (86)

Prepared from (RS)-5-(4-Benzyloxy-phenyl)-4-(6-phenyl-hexanoylamino)-pentanoic acid ethyl ester 79 and LiOH.H$_2$O in THF/H$_2$O (87% yield), isolated as a white solid: $^1$H nmr (d$_6$-DMSO) δ 1.24-2.67 (m, 17H), 3.94 (br s, 1H), 5.11 (s, 2H), 6.98 (d, J=7.1 Hz, 2H), 7.16 (d, J=7.6 Hz, 2H), 7.23-7.48 (m, 10H), 7.65 (br d, J=8.3 Hz, 1H), 12.07 (br s, 1H). $^{13}$C nmr (d$_6$-DMSO) 174.3, 171.6, 156.7, 142.3, 137.2, 131.0, 130.1, 128.4, 128.2, 127.7, 127.6, 125.6, 114.3, 69.1, 49.3, 35.4, 35.1, 30.8, 30.5, 30.2, 29.2, 28.1, 25.1.

(RS)-5-(4-Benzyloxy-phenyl)-4-(8-phenyl-octanoylamino)-pentanoic acid (87)

Prepared from 80 and LiOH.H$_2$O in THF/H$_2$O (97% yield) isolated as a pale yellow oil: $^1$H nmr (d$_6$-DMSO) δ 1.24-2.60 (m, 20H), 3.87 (br s, 1H), 5.03 (s, 2H), 6.89 (d, J=8.5 Hz, 2H), 7.08 (d, J=8.4 Hz, 2H), 7.14-7.44 (m, 10H), 7.59 (br d, J=8.6 Hz, 1H), 12.06 (br s, 1H). $^{13}$C nmr (d$_6$-DMSO) δ 174.3, 171.7, 156.7, 142.3, 137.2, 131.1, 130.1, 128.4, 128.2, 127.8, 127.6, 125.6, 114.3, 69.1, 49.3, 35.5, 35.2, 33.6, 31.0, 30.5, 29.3, 28.6, 28.5, 25.3, 24.5.

(RS)-5-(4-Benzyloxy-phenyl)-4-[7-(2-methoxy-phenyl)-heptanoylamino]-pentanoic acid (88)

Prepared from (RS)-5-(4-Benzyloxy-phenyl)-4-[7-(2-methoxy-phenyl)-heptanoylamino]-pentanoic acid methyl ester 81 ESMS 518 (M+H)$^+$.

(RS)-4-[7-(3-Acetylamino-phenyl)-heptanoylamino]-5-(4-benzyloxy-phenyl)-pentanoic acid (89)

Prepared from (RS)-4-[7-(3-Acetylamino-phenyl)-heptanoylamino]-5-(4-benzyloxy-phenyl)-pentanoic acid methyl ester 82 (quantitative yield) isolated as an opaque gum: $^1$H NMR (500 MHz, d$_4$-MeOH) δ 1.12-1.33 (m, 4H), 1.40-1.50 (m, 2H), 1.52-1.70 (m, 3H), 1.82-1.91 (m, 1H), 2.04-2.11 (m, 2H) superimposed upon 2.09 (s, 3H), 2.23-2.36 (m, 2H), 2.54 (t, J=7.6 Hz, 2H), 2.62 (dd, J=8.5, 13.8 Hz, 1H), 2.75 (dd, J=5.7, 13.8 Hz, 1H), 4.01-4.11 (m, 1H), 4.98 (s, 2H), 6.87 (d, J=8.5 Hz, 2H), 6.89 (d, J=7.8 Hz, 1H), 7.10 (d, J=8.5 Hz, 2H), 7.16 (t, J=7.8 Hz, 1H), 7.24-7.42 (m, 7H). $^{13}$C NMR (125 MHz, d$_4$-MeOH) δ 175.9, 171.6, 144.7, 138.8, 132.1, 131.3, 129.6, 129.5, 128.8, 128.5, 125.4, 121.2, 118.6, 115.8, 71.0, 51.6, 41.2, 37.2, 36.8, 32.3, 31.9, 31.0, 29.9, 26.9, 24.2, 23.8. ESMS 545 (M+H)$^+$.

(RS)-5-(4-Benzyloxy-phenyl)-4-[7-(3-nitro-phenyl)-heptanoylamino]-pentanoic acid (90)

Prepared from (RS)-5-(4-Benzyloxy-phenyl)-4-[7-(3-nitro-phenyl)-heptanoylamino]-pentanoic acid methyl ester 83 (94% yield) isolated as a hygroscopic white solid: $^1$H NMR (500 MHz, d$_4$-MeOH) δ 1.11-1.23 (m, 2H), 1.23-1.33 (m, 2H), 1.40-1.50 (m, 2H), 1.53-1.70 (m, 3H), 1.82-1.91 (m, 1H), 2.02-2.12 (m, 2H), 2.24-2.36 (m, 2H), 2.61 (dd, J=8.6, 13.8 Hz, 1H), 2.67 (t, J=7.7 Hz, 2H), 2.75 (dd, J=5.7, 13.8 Hz, 1H), 4.01-4.12 (m, 1H), 4.98 (s, 2H), 6.86 (d, J=8.6 Hz, 2H), 7.10 (d, J=8.6 Hz, 2H), 7.26 (t, J=7.2 Hz, 1H), 7.32 (t, J=7.2 Hz, 2H), 7.36 (m, 2H), 7.44 (t, J=7.8 Hz, 1H), 7.54 (d, J=7.8 Hz, 1H), 7.96-8.03 (m, 2H). $^{13}$C NMR (125 MHz, d$_4$-MeOH) δ 177.1, 175.9, 158.8, 149.7, 146.3, 138.8, 136.0, 132.2, 131.3, 130.4, 129.5, 128.8, 128.5, 124.0, 121.8, 115.7, 71.0, 51.5, 41.2, 37.1, 36.3, 32.1, 31.8, 31.0, 29.9, 29.8, 26.9. ESMS 533 (M+H)+.

(RS)-5-(4-Benzyloxy-phenyl)-4-(7-pyridin-3-yl-heptanoylamino)-pentanoic acid (91)

Prepared from (RS)-5-(4-Benzyloxy-phenyl)-4-(7-pyridin-3-yl-heptanoylamino)-pentanoic acid methyl ester 84 (95% yield) isolated as a white solid. ESMS 489 (M+H)+.

Example 14

(RS)-5-(4-Hydroxy-phenyl)-4-(7-phenyl-heptanoylamino)-pentanoic acid methyl ester (92)

(RS)-5-(4-Benzyloxy-phenyl)-4-(7-phenyl-heptanoylamino)-pentanoic acid methyl ester 78 (872 mg, 1.74 mmol) was hydrogenated over 10% Pd—C in THF (20 mL) containing HCl solution (1 M, 2.5 mL). The solution was filtered (Celite™) and approximately two thirds of the solvent removed under reduced pressure. The solution was diluted with water and extracted into EtOAc. The combined extracts were washed with water, brine and dried with $MgSO_4$. Evaporation of the solvent in vacuo afforded the title compound (702 mg, 98%). ESMS 412 (M+H)+.

Example 15

General Procedure C; Etherification of Phenols with Picolyl Chloride.

Synthesis of (RS)-4-(7-Phenyl-heptanoylamino)-5-[4-(pyridin-2-ylmethoxy)-phenyl]-pentanoic acid methyl ester (93)

(RS)-5-(4-Hydroxy-phenyl)-4-(7-phenyl-heptanoylamino)-pentanoic acid methyl ester 92 (889 mg, 2.16 mmol), 2-picolylchloride hydrochloride (570 mg, 3.47 mmol) and finely powdered anhydrous $K_2CO_3$ (1.45 g, 10.5 mmol) was stirred in dry DMF (7 mL) for 48 hr. The mixture was poured onto water (40 mL) and extracted into EtOAc. The extract was successively washed with HCl solution (1 M, 30 mL), saturated $NaHCO_3$ solution, brine, and then dried with $MgSO_4$. Concentration of the solvent in vacuo afforded 93 (747 mg, 69 %): $^1$H NMR (CDCl$_3$) δ 1.15-1.40 (m, 4H); 1.40-1.70 (m, 5H); 1.73-1.85 (m, 1H); 2.08 (t, J=7.6 Hz, 2H); 2.34 (m, 2H); 2.58 (t, J=7.6 Hz, 2H); 2.69 (dd, J=15, 6.9 Hz, 1H); 2.77 (dd, J=15, 6.2 Hz, 1H); 3.64 (s, 3H); 4.06-4.21 (m, 1H); 5.17 (s, 2H); 5.37 (d, J=9.3 Hz, 1H); 6.91 (d, J=8.4 Hz, 2H); 7.10 (d, J=8.4 Hz, 2H); 7.12-7.31 (m, 6H); 7.51 (d, J=7.5 Hz, 1H); 7.71 (dt, J=7.5, 1.6 Hz, 1H); 8.60 (m, J=6.0 Hz, 1H). $^{13}$C NMR (CDCl$_3$) δ 174.4, 173.0, 157.5, 157.3, 149.4, 142.8, 137.0, 130.3, 125.8, 122.8, 121.5, 130.6, 128.5, 128.4, 115.0, 70.8, 51.9, 50.2, 40.6, 37.0, 36.0, 31.4, 31.1, 29.2, 29.1, 29.0, 25.8. ESMS 503 (M+H)+.

Also obtained in this fashion are compounds 94-95.

(RS)-4-(7-Phenyl-heptanoylamino)-5-[4-(pyridin-3-ylmethoxy)-phenyl]-pentanoic acid methyl ester (94)

Prepared from (RS)-5-(4-Hydroxy-phenyl)-4-(7-phenyl-heptanoylamino)-pentanoic acid methyl ester 92 (502 mg, 1.22 mmol) and 3-picolylchloride hydrochloride (300 mg, 1.83 mmol) to afford 94 (422 mg, 69%). $^{13}$C NMR (CDCl$_3$) δ 174.4, 173.0, 157.3, 149.5, 149.1, 142.8, 135.5, 132.8, 130.6, 128.5, 128.4, 125.8, 123.7, 114.9, 67.7, 51.9, 50.3, 40.6, 37.0, 36.0, 31.4, 31.1, 29.2, 29.1, 29.0, 25.8. ESMS 503 (M+H)+.

(RS)-4-(7-Phenyl-heptanoylamino)-5-[4-(pyridin-2-ylmethoxy)-phenyl]-pentanoic acid (95)

(RS)-4-(7-Phenyl-heptanoylamino)-5-[4-(pyridin-2-ylmethoxy)-phenyl]-pentanoic acid methyl ester 93 (707 mg, 1.41 mmol) was hydrolysed according to general procedure B to yield the title compound 95 (608 mg, 89%) as a white solid: $^1$H NMR (500 MHz, d$_4$-MeOH) 1.12-1.31 (m, 4H), 1.40-1.50 (m, 2H), 1.50-1.69 (m, 3H), 1.81-1.91 (m, 1H), 2.01-2.12 (m, 2H), 2.23-2.36 (m, 2H), 2.54 (t, J=7.6 Hz, 2H); 2:62 (dd, J=8.5, 13 Hz, 1H), 2.75 (dd, J=5.8, 13 Hz, 1H), 4.00-4.11 (m, 1H), 5.09 (s, 2H), 6.89 (d, J=8.5 Hz, 2H), 7.06-7.25 (m, 7H), 7.29-7.37 (m, 1H), 7.55 (d, J=7.8 Hz, 1H), 7.77-7.87 (m, 1H), 8.45-8.56 (m, 1H). $^{13}$C NMR (125 MHz, d$_4$-MeOH) δ 177.1, 175.9, 158.4, 149.7, 143.9, 139.0, 132.6, 131.4, 129.4, 129.2, 126.6, 124.4, 123.3, 115.7, 71.2, 51.5, 41.2, 37.2, 36.8, 32.5, 31.9, 30.9, 30.01, 29.97, 27.0. ESMS 489 (M+H)+.

(RS)-4-(7-Phenyl-heptanoylamino)-5-[4-(pyridin-3-ylmethoxy)-phenyl]-pentanoic acid (96)

(RS)-4-(7-Phenyl-heptanoylamino)-5-[4-(pyridin-3-ylmethoxy)-phenyl]-pentanoic acid methyl ester 94 (360 mg, 0.72 mmol) was hydrolyzed according to general procedure B to yield 96 (299 mg, 85%) as a white solid: $^1$H NMR (500 MHz, d$_4$-MeOH) δ 1.11-1.34 (m, 4H), 1.39-1.51 (m, 2H), 1.51-1.70 (m, 3H), 1.80-1.92 (m, 1H), 2.02-2.12 (m, 2H), 2.23-2.37 (m, 2H), 2.54 (t, J=7.7 Hz, 2H), 2.63 (dd, J=8.5, 14.0 Hz, 1H), 2.75 (dd, J=5.8, 14.0 Hz, 1H), 3.99-4.13 (m, 1H), 4.86 (s, 2H), 6.90 (d, J=8.6 Hz, 2H), 7.05-7.29 (m, 7H), 7.43 (dd, J=5.0, 7.8 Hz, 1H), 7.88 (d, J=7.8 Hz, 1H), 8.43-8.51 (m, 1H), 8.58 (br s, 1H). $^{13}$C NMR (125 MHz, d$_4$-MeOH) δ 177.1, 175.9, 158.4, 149.4, 149.2, 143.9, 137.5, 135.4, 132.6, 131.4, 129.4, 129.3, 126.6, 125.2, 115.7, 68.3, 51.5, 41.2, 37.2, 36.8, 32.5, 31.8, 30.9, 30.0, 29.9, 27.0. ESMS 489 (M+H)+.

Example 16 (See Scheme 13)

4-Oxo-6-phenyl-hex-5-enoic acid ethyl ester (98)

Benzaldehyde 69a (5.40 g, 50 mmol) and ethyl levulinate 97 (7.21 g, 50 mmol) were dissolved in benzene (25 mL) then glacial acetic acid (6 mL) and piperidine (2 mL) were added. The solution was stirred and refluxed under a Dean-Stark trap under argon for 5 hr. The solution was cooled and diluted with ether and washed twice with 2M HCl, 5% NaHCO$_3$ brine and evaporated to give an oil 11.0 g, 95%. $^1$H NMR (300 MHz, CDCl$_3$) δ 1.27, 3H, t(J 7.1); 2.69, 2H, t(J 6.7); 3.02, 2H, t(J 6.7); 4.16, 2H, q(J 7.1); 6.77, 1H, d(J 16.2); 7.37-7.43, 3H, m; 7.51-7.60, 2H, m; 7.60, 1H, d(J 16.4). $^{13}$C NMR (CDCl$_3$) 14.2, 28.2, 35.2, 60.7, 125.8, 128.3, 128.9, 130.5, 134.4, 142.9, 172.9, 198.1.

4-Oxo-6-phenyl-hexanoic acid (99)

A solution of 98 (5.0 g, 21 mmol) in ethanol (50 mL) was hydrogenated over 10% Pd—C at 30 psi and room temperature for 4 hr. The catalyst was filtered off and a soluton of NaOH (1 g) in water (10 mL) was added. The solution was stirred for 1 hr then diluted with water and washed with ether. The aqueous solution was acidified with HCl and extracted with ether. The ether extracts were washed with brine, dried over MgSO$_4$ and evaporated to give an oil 4.1 g, 94%.

4-Hydroxyimino-6-phenyl-hexanoic acid (100)

The ketone 99 (3.0 g, 13.6 mmol) and hydroxylamine hydrochloride (1.98 g, 27 mmol) were dissolved in methanol (20 mL) then sodium methoxide (2.9 g) was added. The solution was stirred and refluxed for 2 hr then cooled. Ether was added and the organic layer was washed twice with 2M HCl, brine and dried over MgSO$_4$. Removal of solvent gave the oximes 100 (2.7 g 90%) as a mixture of E:Z isomers in the ratio 1.5:1.

(RS)-4-Amino-6-phenyl-hexanoic acid (101)

A solution of the oximes 100 (2.7 g 12.2 mmol) in ethanol (40 mL) was hydrogenated over 10% Pd—C at 40 psi and 50° C. for 3 days. The catalyst was filtered off and the solvent was evaporated. The residue was partitioned between ether and 0.1 M HCl and the aqueous layer was lyophilized giving 101 as a white powder (130 mg, 5%).

(RS)-6-Phenyl-4-(7-phenyl-heptanoylamino)-hexanoic acid (102)

Phenylheptanoic acid (105 mg 0.51 mmol) and BOP (250 mg, 0.56 mmol) were dissolved in dry DMF 2 mL then DIPEA 200 µL was added. After mixing for 3 min the solution was added to (RS)-4-amino-6-phenyl-hexanoic acid (101) (105 mg, 0.51 mmol) and the solution was stirred at room temperature for 1 hr. Ether was added and the solution was washed twice with 1 M HCl and brine then dried over MgSO$_4$. Removal of solvent gave a white solid 200 mg, which was recrystallised from EtOAc-hexane. $^1$H NMR (300 MHz, CDCl$_3$) δ 7.30-7.22 (m, 4H), 7.21-7.11 (m, 6H), 6.17 (br, 1H, NH), 4.02 (m, 1H), 2.70-2.53 (m, 4H), 2.38 (m, 2H), 2.22 (m, 2H), 2.00-1.52 (m, 8H), 1.44-1.27 (m, 4H).

Example 17

(4R)-Methoxycarbonylamino-6-(4-phenoxy-phenyl)-hex-5-enoic acid ethyl ester (104)

4-Phenoxy-benzyltriphenylphosphonium chloride (500 mg, 1.04 mmol) was dissolved in dry THF (15 mL) then cooled to −15° C. under argon. A solution of sodium hexamethyldisilazide in THF (1.0 M, 1 mL) was added then after 20 min a solution of the aldehyde 103 [Wei, and Knaus, *J. Org. Chem.* 1993, 58(6): 1586-8] (210 mg, 0.96 mmol) in THF (5 mL) was added. The solution was warmed to room temperature and stirred overnight. The solvent was evaporated and the residue was partitioned between ether and 2M HCl. The ether layer was washed with NaHCO$_3$, brine, dried over MgSO$_4$ and evaporated. The residue was purified by flash chromatography giving a colourless oil 192 mg, 52%.

(4R)-Amino-6-(4-phenoxy-phenyl)-hexanoic acid (105)

A solution NaOH (50 mg) in water (3 mL) was added to a solution of 104 (191 mg, 0.50 mmol) in ethanol (12 mL). After stirring at room temperature for 2 hr the solution was diluted with ether and washed with 2M HCl. The organic layer was washed with brine and dried over MgSO$_4$ and evaporated to dryness. The residue was dissolved in ethanol (20 mL) and hydrogenated over 10% Pd—C for 1 hr. The catalyst was filtered off and the solvent was evaporated and the residue was dried under high vacuum. The residue was dissolved in dry DCM (5 mL) then trimethylsilyl iodide (100 µL) was added. The solution was stirred at room temperature for 2 hr then water (1 mL) was added. After stirring for a further 5 min the mixture was evaporated to dryness. The crude amino acid was used immediately for the preparation of 106 and 107 without purification.

6-(4Phenoxy-phenyl)-4R-(7-phenyl-heptanoylamino)-hexanoic acid (106)

Prepared according to General Method A from phenylheptanoic acid (51) (105 mg 0.51 mmol) (4R)-amino-6-(4-phenoxy-phenyl)-hexanoic acid (105) (150 mg 0.50 mmol). as an oil. ESMS 488 (M+H)$^+$.

6-(4-Phenoxy-phenyl)-4R-(7-pyridin-3-yl-heptanoylamino)-hexanoic acid (107)

Prepared according to General Method A from (E)-7-Pyridin-3-yl-hept-6-enoic acid (76) and (4R)-amino-6-(4-phenoxy-phenyl)-hexanoic acid (105) as an oil. $^1$H NMR (300 MHz, CDCl$_3$) δ 8.81 (s, 1H), 8.60 (m, 1H), 8.12 (d, J=7.9 Hz, 1H), 7.74 (dd, J=7.8, 5.5 Hz, 1H), 7.35-7.27 (m, 2H), 7.15-7.03 (m, 3H), 7.00-6.86 (m, 4H), 6.10 (d, J=8.9 Hz, 1H), 4.01 (m, 1H), 2.81 (m, 2H), 2.61 (m, 2H), 2.47-2.29 (m, 2H), 2.28-2.05 (m, 2H), 2.01-1.51 (m, 8H), 1.48-1.24 (m, 4H). ESMS 489 (M+H)$^+$.

Example 8

Assay for Inhibition of Human Non-Pancreatic sPLA2 (type IIa)

A mixed nucelle colorimetric assay utilising a microtitreplate reader was used as described by Reynolds, L. J.; Hughes, L. L.; Dennis, E. A. "Analysis of human synovial fluid phospholipase A$_2$ on short chain phosphatidylcholine-mixed micelles: Development of a spectrophotometric assay suitable for a microplate reader". *Anal Biochem.* 1992, 204, 190-197.

Reagents were obtained commercially in the sPhospholipase A$_2$ Assay Kit, Cayman Chemical Company MI USA. Buffer (25 mM Tris HCl at pH 7.5, 1 mg/mL BSA, 0.3 mM Triton X-100, 100 mM KCl, 10 mM CaCl$_2$), substrate (diheptanoyl thio-phosphatidyl choline), DTNB (5,5'-dithiobis(2-nitrobenzoic acid)) and a 96 well plate were all provided. Recombinant hIIa-PLA$_2$ was provided by the Garvan Institute for Medical Research. The enzyme was found to be homogenous by LCMS and a MS reconstruct yielded a molecular weight of 13,905 g/mole as expected. Standard inhibitor solutions were prepared from anhydrous DMSO. All samples were run in triplicate including the blank and control samples. Data was collected on a Molecular Devices Spectramax 250 Microplate Spectrophotometer using Softmax Pro Microplate Analysis Software v2.21. Diphenylheptanoyl Thio-PC is processed by s-PLA$_2$ and the free thiol produced is detected with DTNB (Ellman's Reagent). 5-Thio-2-nitrobenzoic acid is detected spectrophotometrically at 414 nM. IC$_{50}$'s were determined by assaying inhibitors at a range of concentrations. Inhibitor concentration was plotted as a function of the inverse of the initial velocity (Dixon plot) and extrapolation to the X axis yielded the IC$_{50}$.

An example of the utility of the data obtained from the above assay is shown in Table 2 and FIG. 1. Representative $IC_{50}$ data and the corresponding Dixon plots for compounds (62) and (68) are given.

TABLE 2

Inhibition of human secretary $PLA_2$ $IC_{50}$. Data for selected compounds

| Compound | chirality | $R^C$ | $R^A$ | $R^B$ | t | D | E | F | $IC_{50}$ |
|---|---|---|---|---|---|---|---|---|---|
| 68 | S | — | H | H | 6 | CH | — | — | 30 nM |
| 85 | RS | — | H | H | 6 | CH | — | — | 58 nM |
| 86 | RS | — | H | H | 5 | CH | — | — | 383 nM |
| 87 | RS | — | H | H | 7 | CH | — | — | 435 nM |
| 88 | RS | — | H | OMe | 6 | CH | — | — | 7.4 μM |
| 89 | RS | — | NHCOMe | H | 6 | CH | — | — | 8.1 μM |
| 90 | RS | — | $NO_2$ | H | 6 | CH | — | — | 1.07 μM |
| 91 | RS | — | H | H | 6 | N | — | — | 1.52 μM |
| 95 | RS | — | H | H | 6 | CH | N | CH | 428 nM |
| 96 | RS | — | H | H | 6 | CH | CH | N | 454 nM |
| 19 | S | $CH_2Ph$ | H | H | 6 | CH | — | — | 5.7 μM |
| 20 | S | $(CH_2)_3Ph$ | H | H | 6 | CH | — | — | 2.9 μM |
| 32 | S | $(CH_2)_3Ph$ | H | H | 6 | CH | — | — | 2.5 μM |
| 66 | S | — | H | H | 6 | CH | — | — | 356 nM |
| 57 | R | Ph | H | H | 6 | CH | — | — | 656 nM |
| 62 | R | H | H | H | 6 | CH | — | — | 24 nM |
| 102 | RS | — | H | H | 6 | CH | — | — | 1.5 μM |
| 106 | R | — | H | H | 6 | CH | | | 99 nM |
| 107 | R | — | H | H | 6 | N | | | 1.7 μM |
| 111 | S | — | H | H | 6 | CH | N | CH | 214 nM |
| 112 | S | — | H | H | 6 | CH | CH | N | 247 nM |

What is claimed is:

1. A compound of Formula (I):

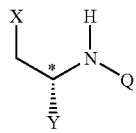

wherein
X is selected from the group consisting of:
CRR'$CO_2H$, CRR'-tetrazolyl, CRR'$SO_3H$, CRR'P(O)(OH)$_2$, CRR'P(O)(OH)(OR''), CHRCH$_2$CO$_2$H, CHRCH$_2$-tetrazolyl, CHRCH$_2$SO$_3$H, CHRCH$_2$P(O)(OH)$_2$, CHRCH$_2$P(O)(OH)(OR''), OP(O)(OH)R', NRSO$_3$H, NRP(O)(OH)$_2$, and NRP(O)(OH)(OR'')
wherein R, R' and R" are independently selected from the group consisting of hydrogen, optionally substituted alkyl, optionally substituted alkenyl, optionally substituted alkynyl, optionally substituted acyl, optionally substituted arylalkyl, optionally substituted cycloalkylalkyl and optionally substituted heterocyclylalkyl, except that R" is not hydrogen;
Q is a group of formula (a)

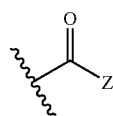

Y is a group of formula
(i) —(CH$_2$)$_m$-aa-(CH$_2$)$_n$—B;
and Z is a group of formula:
(iii) —(CH$_2$)$_p$-A-(CH$_2$)$_q$-A'-(CH$_2$)$_r$—B
wherein
m is 0 or 1, n, p, q and r are independently selected from 0 to 15;

aa is an amino acid side chain residue, provided that the amino acid is not cysteine or homocysteine;
A and A' are independently selected from the group consisting of O, NH, NR, NHC(O), NRC(O), CH$_2$, CHR, CHNH$_2$, C(O), C(O)O, C(O)NH, OC(O), and CH=CH, wherein R is selected from optionally substituted alkyl, optionally substituted alkenyl, optionally substituted alkynyl, optionally substituted aryl, optionally substituted cycloalkyl, optionally substituted heterocyclyl, optionally substituted arylalkyl, optionally substituted cycloalkylalkyl and optionally substituted heterocyclylalkyl; and B is selected from the group consisting of, hydrogen, halogen, optionally substituted alkyl, optionally substituted alkenyl, optionally substituted alkynyl, optionally substituted aryl, optionally substituted heterocyclyl, optionally substituted cycloalkyl, optionally substituted aryloxy, optionally substituted heterocyclyloxy; optionally substituted cycloalkoxy, and CO$_2$H;

wherein m, n, p, q, r, aa, A, A' and B are such that the longest continuous chain of atoms in a group of formula (i) or (iii) is from 5 to 15 atoms long; and provided that the optional substituents are not mercapto, alkylthio, benzylthio or acylthio;

wherein the compound of formula (I) has an $IC_{50}$ activity for inhibition of human non-pancreatic $sPLA_2$ at a concentration of 50 μm or less, or salt or thereof.

2. A compound according to claim 1 wherein X is selected from the group consisting of CH$_2$CO$_2$H, CHRCO$_2$H, CH$_2$-tetrazolyl, CHR-tetrazolyl, CH$_2$SO$_3$H, CHRSO$_3$H, CH$_2$P(O)(OH)$_2$, CH$_2$P(O)(OH)(OR''), CHRP(O)(OH)$_2$, CHRP(O)(OH)(OR''), CH$_2$CH$_2$CO$_2$H, CHRCH$_2$CO$_2$H, CH$_2$CH$_2$-tetrazolyl, CHRCH$_2$-tetrazolyl, CHCH$_2$SO$_3$H, CHRCH$_2$SO$_3$H, CH$_2$CH$_2$P(O)(OH)$_2$, CH$_2$CH$_2$P(O)(OH)$_2$ CHRCH$_2$P(O)(OH)$_2$, CH$_2$CH$_2$P(O)(OH)(OR''), CHRCH$_2$P(O)(OH)(OR''), and OP(O)(OH)R'.

3. A compound according to claim 1 wherein R, R' and R" are independently selected from hydrogen, alkyl, arylalkyl, cycloalkylalkyl and heterocyclylalkyl, wherein each of alkyl, arylalkyl, cycloalkylalkyl and heterocyclylalkyl may be substituted or unsubstituted except that R" is not hydrogen.

4. A compound according to claim 3 wherein R, R' and R" are independently selected from hydrogen, $C_{1-15}$ alkyl, $C_{4-7}$ cycloalkylalkyl benzyl, phenylethyl, phenylpropyl, phenylbutyl, phenylpentyl, phenylhexyl, pyridylmethyl, pyridylethyl, pyridylpropyl, pyridylbutyl, pyridylpentyl and pyridylhexyl wherein each of $C_{1-15}$ alkyl, $C_{4-7}$ cycloalkylalkyl, benzyl, phenylethyl, phenylpropyl, phenylbutyl, phenylpentyl, phenylhexyl, pyridylmethyl, pyridylethyl, pyridylpropyl, pyridylbutyl, pyridylpentyl and pyridylhexyl may be substituted or unsubstituted except that R" is not hydrogen.

5. A compound according to claim 1 wherein X is selected from the group consisting of $CRR'CO_2H$, $CRR'$-tetrazolyl, $CRR'SO_3H$, $CRR'P(O)(OH)_2$ and $CRR'P(O)(OH)(OR")$.

6. A compound according to claim 3 wherein at least one of R and R' is hydrogen.

7. A compound according to claim 1 wherein aa is a side chain residue from the group of amino acids consisting of Histidine, Tryptophan, Serine, Tyrosine, Threonine, Glutamic acid, Aspartic acid, Lysine, Arginine, Alanine, Ornithine, Phenylalanine, Glutamine, asparagine, β-alanine and their homo derivatives.

8. A compound according to claim 1 wherein B is selected from the group consisting of optionally substituted $C_{4-7}$ cycloalkyl, optionally substituted phenyl and optionally substituted 5- or 6-membered heterocyclyl.

9. A compound according to claim 1 wherein A and A' are independently CH=CH or $CH_2$.

10. A compound according to claim 9 wherein Z is an alkyl chain of 6 to 11 carbon atoms in length or an alkenyl chain, having one or two double bonds, of 6 to 11 carbon atoms in length.

11. A compound according to claim 1 wherein one of A or A' is O while the other is $CH_2$ or CH=CH.

12. A compound according to claim 9 wherein Z is a $C_5$-$C_7$ alkyl chain or a $C_5$-$C_7$ alkenyl (having one or two double bonds) chain terminated by an optionally substituted phenyl group, 5-6-membered heterocyclyl ring or 5-6-membered cycloalkyl ring.

13. A compound according to claim 1 having Formula (IA):

(IA)

wherein X is $CRR'CO_2H$ or $CHRCH_2CO_2H$.

14. A compound according to claim 13 wherein X is $CH_2CO_2H$ or $CH_2CH_2CO_2H$.

15. A compound according to claim 13 wherein the B moiety of Y is an optionally substituted phenyl group, an optionally substituted $C_{4-7}$ cycloalkyl group or an optionally substituted 5-6-membered heterocycle.

16. A compound according to claim 15 wherein B is an optionally substituted phenyl group or an optionally substituted pyridyl group.

17. A compound selected from the group consisting of (102)

(106)

(86) $R^A = R^B = H$, t = 5, D = CH
(87) $R^A = R^B = H$, t = 7, D = CH
(85) $R^A = R^B = H$, t = 6, D = CH
(88) $R^A = H$, $R^B = OMe$, t = 6, D = CH
(89) $R^A = NHCOMe$, $R^B = H$, t = 6, D = CH
(90) $R^A = H$, $R^B = NO_2$, t = 6, D = CH
(91) $R^A = R^B = H$, t = 6, D = N

(95) E = N, F = CH
(96) E = CH, F = N.

18. An enantiomeric mixture comprising a compound according to claim 1.

19. A compound according to claim 1 wherein m+n is between 5 and 16.

20. A compound according to claim 7 wherein m+n is between 5 and 16.

21. A compound according to claim 1 or 13 wherein Y is:
a) $(CH_2)_m$-aa-$(CH_2)_n$—B, wherein m is 0 and n is 1, 2 or 3; or wherein m is 1 and n is 0, 1, 2 or 3;
aa is an amino acid side chain residue from an amino acid selected from the group consisting of arginine, glutamic acid, serine, asparagine, glutamine, threonine, aspartic acid, histidine, lysine, tyrosine, tryptophan, alanine, β-alanine, ornithine and phenylalanine; and
B is a phenyl group, a 5-6 membered heterocyclyl group or a $C_5$-$C_6$ cycloalkyl group each of which may be substituted or unsubstituted.

22. A compound according to claim 7 wherein aa is a side chain residue selected from the group of amino acids consisting of histidine, tryptophan, serine, tyrosine, threonine, glutamic acid, aspartic acid, alanine, β-alanine, ornithine, phenylalanine, glutamine and their homo derivatives.

23. A compound according to claim 7 wherein aa is a side chain residue from tyrosine.

24. A compound according to claim 13 wherein Y is:
a) $(CH_2)_m$-aa-$(CH_2)_n$—B, wherein m is 0 and n is 1, 2 or 3; or m is 1 and n is 0, 1, 2 or 3;
aa is an amino acid side chain residue from an amino acid selected from the group consisting of arginine, glutamic acid, serine, asparagine, glutamine, threonine, aspartic acid, histidine, lysine, tyrosine, tryptophan, alanine, β-alanine, ornithine and phenylalanine; and
B is a phenyl group, a 5-6 membered heterocyclyl group or a $C_5$-$C_6$ cycloalkyl group each of which may be substituted or unsubstituted
and wherein Z is a $C_5$-$C_7$ alkyl chain or a $C_5$-$C_7$ alkenyl chain having one or two double bonds, terminated by an optionally substituted phenyl group, 5-6 membered heterocyclyl ring or 5-6-membered cycloalkyl ring.

25. A compound according to claim 21 wherein aa is an amino acid side chain residue from an amino acid selected from the group consisting of glutamic acid, serine, asparagine, glutamine, threonine, aspartic acid, histidine, tyrosine, tryptophan, alanine, β-alanine, ornithine and phenylalanine.

26. A compound according to claim 24 wherein aa is an amino acid side chain residue from an amino acid selected from the group consisting of glutamic acid, serine, asparagine, glutamine, threonine, aspartic acid, histidine, tyrosine, tryptophan, alanine, β-alanine, ornithine and phenylalanine.

27. The compound of formula:

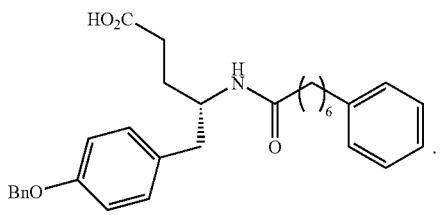

68

28. A compound of Formuia (I):

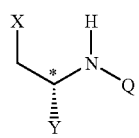

wherein
X is selected from the group consisting of:
CRR'$CO_2$H, CRR'-tetrazolyl, CRR'$SO_3$H, CRR'P(O)(OH)$_2$, CRR'P(O)(OH)(OR''), CHR$CH_2CO_2$H, CHR$CH_2$-tetrazolyl, CHR$CH_2SO_3$H, CHR$CH_2$P(O)(OH)$_2$, CHR$CH_2$P(O)(OH)(OR''), OP(O)(OH)R', NR$SO_3$H, NRP(O)(OH)$_2$, and NRP(O)(OH)(OR'')
wherein R, R' and R'' are independently selected from the group consisting of hydrogen, optionally substituted alkyl, optionally substituted alkenyl, optionally substituted alkynyl, optionally substituted acyl, optionally substituted arylalkyl, optionally substituted cycloalkylalkyl and optionally substituted heterocyclylalkyl, except that R'' is not hydrogen;
Q is a group of formula (a)

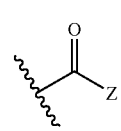

(a)

Y is a group of formula
(i) —$(CH_2)_m$-aa-$(CH_2)_n$—B;
and Z is a group of formula:
(iii) —$(CH_2)_p$-A-$(CH_2)_q$-A'-$(CH_2)_r$—B
wherein
m is 0 or 1, n, p, q and r are independently selected from 0 to 15;
aa is an amino acid side chain residue, provided that the amino acid is not cysteine or homocysteine;
A and A' are independently selected from the group consisting of O, NH, NR, NHC(O), NRC(O), $CH_2$, CHR, $CHNH_2$, C(O), C(O)O, C(O)NH, OC(O), and CH═CH, wherein R is selected from optionally substituted alkyl, optionally substituted alkenyl, optionally substituted alkynyl, optionally substituted aryl, optionally substituted cycloalkyl, optionally substituted heterocyclyl, optionally substituted arylalkyl, optionally substituted cycloalkylalkyl and optionally substituted heterocyclylalkyl; and
B is selected from the group consisting of, hydrogen, halogen, optionally substituted alkyl, optionally substituted alkenyl, optionally substituted alkynyl optionally substituted aryl, optionally substituted heterocyclyl, optionally substituted cycloalkyl, optionally substituted aryloxy, optionally substituted heterocyclyloxy; optionally substituted cycloalkoxy, and $CO_2$H;
wherein m, n, p, q, r, aa, A, A' and B are such that the longest continuous chain of atoms in a group of formula (i) or (iii) is from 5 to 15 atoms long; and provided that the optional substituents are not mercapto, alkylthio, benzylthio or acylthio; wherein the compound of formula (I) has an $IC_{50}$ activity for inhibition of human non-pancreatic sPLA$_2$ at a concentration of 50 μm or less,
or salt or prodrug thereof.

29. A composition comprising a compound according to claim 1, together with a pharmaceutically acceptable diluent, carrier or excipient.

30. A method for the treatment of an inflammatory disease in a subject in need thereof comprising the administration of a treatment effective amount of a compound according to claim 1 to said subject.

* * * * *